US008887954B2

(12) United States Patent
Carpenter et al.

(10) Patent No.: US 8,887,954 B2
(45) Date of Patent: Nov. 18, 2014

(54) COMPACT SPRAY DEVICE

(71) Applicant: S.C. Johnson & Son, Inc., Racine, WI (US)

(72) Inventors: M. Scott Carpenter, Racine, WI (US); Paul E. Furner, Racine, WI (US); Thomas P. Gasper, Germantown, WI (US); Chris A. Kubicek, East Troy, WI (US); Leon M. Lemon, Mendon, UT (US); Brent D. Madsen, Providence, UT (US); Kenneth W. Michaels, Spring Grove, IL (US); Cory J. Nelson, Racine, WI (US); Michael E. Short, Racine, WI (US); Gene Sipinski, Elgin, IL (US); Nathan R. Westphal, Union Grove, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 4 days.

(21) Appl. No.: 13/647,272

(22) Filed: Oct. 8, 2012

(65) Prior Publication Data
US 2013/0026181 A1    Jan. 31, 2013

Related U.S. Application Data

(63) Continuation of application No. 13/235,192, filed on Sep. 16, 2011, now Pat. No. 8,342,363, which is a (Continued)

(51) Int. Cl.
*B67D 1/00*    (2006.01)
*G04C 1/12*    (2006.01)
(Continued)

(52) U.S. Cl.
CPC ............. *B65D 83/267* (2013.01); *B05B 12/12* (2013.01); *B65D 83/262* (2013.01); *B05B 11/3053* (2013.01); *B05B 12/02* (2013.01); *A61L 9/14* (2013.01); *B05B 12/122* (2013.01)
USPC .............. 222/52; 222/644; 222/646; 222/647; 222/649; 222/504; 239/70; 239/337

(58) Field of Classification Search
USPC ......... 222/638, 639, 642, 643, 644, 645, 646, 222/647, 648, 649, 402.13, 402.15, 504, 222/333, 61, 52, 62, 64, 162, 132, 135, 222/137; 239/69, 70, 333, 337
See application file for complete search history.

(56) References Cited

U.S. PATENT DOCUMENTS

D48,809 S    4/1916   Baldwin
D84,253 S    5/1931   McFadden
(Continued)

FOREIGN PATENT DOCUMENTS

AR       056799 A4    11/2006
AU       591829        9/1989
(Continued)

OTHER PUBLICATIONS

Web Page "AirWick Fresh Matic" @ http://www.gnpd.com/sinatra/gnpd&lang=uk/images/zoom&id=342358&pic__num=0&xOFF . . . dated Mar. 7, 2005 (1 page).

(Continued)

*Primary Examiner* — Kevin P Shaver
*Assistant Examiner* — Stephanie E Williams

(57) ABSTRACT

An automatic discharge device includes a housing retaining two containers therein. An actuator arm is attached to the housing and movable between first and second positions. A drive unit is provided for automatically moving the actuator arm into one of the first and second positions in response to a signal from at least one of a timer, a sensor, and a manual switch. The movement of the actuator arm actuates a valve stem of one of the two containers in one of the first and second positions. The actuator arm is adapted to spray fluid disposed in an interior of the two containers.

12 Claims, 34 Drawing Sheets

Related U.S. Application Data continuation of application No. 11/725,402, filed on Mar. 19, 2007, now Pat. No. 8,061,562, which is a continuation-in-part of application No. 11/247,793, filed on Oct. 11, 2005, now Pat. No. 7,837,065.

(60) Provisional application No. 60/617,950, filed on Oct. 12, 2004.

(51) Int. Cl.
  *A01G 27/00* (2006.01)
  *B05B 12/12* (2006.01)
  *B65D 83/26* (2006.01)
  *B05B 12/02* (2006.01)
  *A61L 9/14* (2006.01)
  *B05B 11/00* (2006.01)

(56) References Cited

U.S. PATENT DOCUMENTS

| | | |
|---|---|---|
| D103,209 S | 2/1937 | Beiser |
| D128,935 S | 8/1941 | Derham et al. |
| 2,550,825 A | 5/1951 | Kolodie |
| 2,613,108 A | 10/1952 | Krause |
| D180,916 S | 9/1957 | Perlman |
| 2,928,573 A | 3/1960 | Edelstein |
| 2,971,382 A | 2/1961 | Harris |
| 3,018,056 A | 1/1962 | Montgomery |
| 3,127,060 A | 3/1964 | Vosbikian et al. |
| 3,138,331 A | 6/1964 | Kutik |
| 3,165,238 A | 1/1965 | Willey |
| 3,185,356 A | 5/1965 | Venus, Jr. |
| 3,187,948 A | 6/1965 | Hunt |
| 3,187,949 A | 6/1965 | Mangel |
| 3,199,732 A | 8/1965 | Strachan |
| 3,228,609 A | 1/1966 | Edelstein et al. |
| 3,240,389 A | 3/1966 | Genua |
| 3,289,886 A | 12/1966 | Goldsholl et al. |
| 3,305,134 A | 2/1967 | Carmichael et al. |
| 3,326,418 A | 6/1967 | Kropp |
| 3,368,717 A | 2/1968 | Weber |
| 3,369,697 A | 2/1968 | Glucksman et al. |
| 3,388,834 A | 6/1968 | Hart |
| 3,398,864 A | 8/1968 | Kolodziej |
| 3,419,189 A | 12/1968 | Iketani |
| 3,472,457 A | 10/1969 | McAvoy |
| 3,477,613 A | 11/1969 | Mangel |
| 3,497,108 A | 2/1970 | Mason |
| 3,498,504 A | 3/1970 | Wilkins |
| 3,542,248 A | 11/1970 | Mangel |
| 3,543,122 A | 11/1970 | Klebanoff et al. |
| 3,584,766 A | 6/1971 | Hart |
| 3,587,332 A | 6/1971 | Bell |
| 3,589,563 A | 6/1971 | Carragan et al. |
| 3,610,471 A | 10/1971 | Werner |
| 3,615,041 A | 10/1971 | Bischoff |
| 3,617,214 A | 11/1971 | Dolac |
| 3,627,176 A | 12/1971 | Sailors |
| 3,643,836 A | 2/1972 | Hunt |
| 3,658,209 A | 4/1972 | Freeman et al. |
| 3,664,548 A | 5/1972 | Broderick |
| 3,666,144 A | 5/1972 | Winder |
| 3,677,441 A | 7/1972 | Nixon, Jr. et al. |
| 3,726,437 A | 4/1973 | Siegel |
| 3,732,509 A | 5/1973 | Florant et al. |
| 3,739,944 A | 6/1973 | Rogerson |
| 3,758,002 A | 9/1973 | Doyle et al. |
| 3,779,425 A | 12/1973 | Werner |
| 3,784,061 A | 1/1974 | Hogan |
| 3,817,429 A | 6/1974 | Smrt |
| 3,837,532 A | 9/1974 | Sahatjian et al. |
| 3,841,525 A | 10/1974 | Siegel |
| 3,856,443 A | 12/1974 | Salvi |
| 3,865,275 A | 2/1975 | De Nunzio |
| 3,870,274 A | 3/1975 | Broe |
| 3,929,259 A | 12/1975 | Fegley et al. |
| 3,952,916 A | 4/1976 | Phillips |
| 3,968,905 A | 7/1976 | Pelton |
| 3,974,941 A | 8/1976 | Mettler |
| 3,980,205 A | 9/1976 | Smart |
| RE29,117 E | 1/1977 | Sahajian et al. |
| D243,017 S | 1/1977 | Fossella |
| 4,004,550 A | 1/1977 | White et al. |
| 4,006,844 A | 2/1977 | Corris |
| 4,011,927 A | 3/1977 | Smith |
| 4,063,664 A | 12/1977 | Meetze, Jr. |
| 4,068,575 A | 1/1978 | Difley et al. |
| 4,068,780 A | 1/1978 | Fegley |
| 4,077,542 A | 3/1978 | Petterson |
| 4,184,612 A | 1/1980 | Freyre |
| 4,235,373 A | 11/1980 | Clark |
| 4,238,055 A | 12/1980 | Staar |
| 4,396,152 A | 8/1983 | Abplanalp |
| 4,483,466 A | 11/1984 | Gutierrez |
| 4,544,086 A | 10/1985 | Hill et al. |
| 4,572,410 A | 2/1986 | Brunet |
| 4,666,638 A | 5/1987 | Baker et al. |
| 4,671,435 A | 6/1987 | Stout et al. |
| 4,690,312 A | 9/1987 | Crapser et al. |
| 4,695,435 A | 9/1987 | Spector |
| 4,742,583 A | 5/1988 | Yoshida et al. |
| 4,798,935 A | 1/1989 | Pezaris |
| 4,801,093 A | 1/1989 | Brunet et al. |
| 4,816,951 A | 3/1989 | Zago |
| 4,830,791 A | 5/1989 | Muderlak et al. |
| 4,852,802 A | 8/1989 | Iggulden et al. |
| 4,877,989 A | 10/1989 | Drews et al. |
| D309,943 S | 8/1990 | Jones et al. |
| 4,967,935 A | 11/1990 | Celest |
| 4,989,755 A | 2/1991 | Shiau |
| 5,014,881 A | 5/1991 | Andris |
| 5,014,884 A | 5/1991 | Wunsch |
| 5,018,963 A | 5/1991 | Diedrich |
| 5,025,516 A | 6/1991 | Wilson |
| 5,025,962 A | 6/1991 | Renfro |
| 5,038,972 A | 8/1991 | Muderlak et al. |
| 5,055,822 A | 10/1991 | Campbell et al. |
| D323,554 S | 1/1992 | Hoyt et al. |
| 5,105,133 A | 4/1992 | Yang |
| 5,134,961 A | 8/1992 | Giles et al. |
| D329,170 S | 9/1992 | Hoffer |
| 5,175,791 A | 12/1992 | Muderlak et al. |
| 5,198,157 A | 3/1993 | Bechet |
| 5,221,025 A | 6/1993 | Privas |
| 5,230,837 A | 7/1993 | Babasade |
| 5,243,326 A | 9/1993 | Disabato |
| 5,249,718 A | 10/1993 | Muderlak |
| 5,269,445 A | 12/1993 | Tobler |
| D350,192 S | 8/1994 | Patel et al. |
| 5,337,926 A | 8/1994 | Drobish et al. |
| 5,337,929 A | 8/1994 | van der Heijden |
| 5,342,584 A | 8/1994 | Fritz et al. |
| 5,353,744 A | 10/1994 | Custer |
| 5,358,147 A | 10/1994 | Adams et al. |
| D352,236 S | 11/1994 | Althaus |
| 5,383,580 A | 1/1995 | Winder |
| RE34,847 E | 2/1995 | Muderlak et al. |
| 5,392,768 A | 2/1995 | Johansson et al. |
| 5,394,866 A | 3/1995 | Ritson et al. |
| 5,397,028 A | 3/1995 | Jesadanont |
| 5,434,386 A | 7/1995 | Glenn et al. |
| 5,445,324 A | 8/1995 | Berry et al. |
| 5,449,117 A | 9/1995 | Muderlak et al. |
| 5,450,336 A | 9/1995 | Rubsamen et al. |
| 5,487,502 A | 1/1996 | Liao |
| 5,489,047 A | 2/1996 | Winder |
| 5,497,764 A | 3/1996 | Ritson et al. |
| 5,499,016 A | 3/1996 | Pantus |
| 5,503,303 A | 4/1996 | LaWare et al. |
| 5,520,166 A | 5/1996 | Ritson et al. |
| 5,522,378 A | 6/1996 | Ritson et al. |
| 5,531,344 A | 7/1996 | Winner |
| 5,542,605 A | 8/1996 | Campau |
| 5,591,409 A | 1/1997 | Watkins |

(56) References Cited

U.S. PATENT DOCUMENTS

| | | | |
|---|---|---|---|
| 5,622,162 A | 4/1997 | Johansson et al. |
| D380,257 S | 6/1997 | Ganor |
| D380,258 S | 6/1997 | Muller et al. |
| D380,821 S | 7/1997 | Chen |
| 5,647,388 A | 7/1997 | Butler, Jr. et al. |
| 5,657,910 A | 8/1997 | Keyser |
| 5,673,825 A | 10/1997 | Chen |
| 5,676,283 A | 10/1997 | Wang |
| D386,564 S | 11/1997 | Mycroft |
| 5,685,456 A | 11/1997 | Goldstein |
| 5,695,091 A | 12/1997 | Winings et al. |
| 5,699,243 A | 12/1997 | Eckel et al. |
| 5,702,036 A | 12/1997 | Ferrara |
| 5,735,918 A | 4/1998 | Barradas |
| 5,743,251 A | 4/1998 | Howell et al. |
| 5,743,252 A | 4/1998 | Rubsamen et al. |
| 5,755,218 A | 5/1998 | Johansson et al. |
| D395,494 S | 6/1998 | Becker |
| 5,772,074 A | 6/1998 | Dial et al. |
| 5,787,947 A | 8/1998 | Hertsgaard |
| 5,791,524 A | 8/1998 | Demarest |
| 5,806,697 A | 9/1998 | Harbutt et al. |
| 5,810,265 A | 9/1998 | Cornelius et al. |
| 5,811,766 A | 9/1998 | Fabrikant et al. |
| 5,823,390 A | 10/1998 | Muderlak et al. |
| 5,826,570 A | 10/1998 | Goodman et al. |
| 5,853,129 A | 12/1998 | Spitz |
| 5,862,844 A | 1/1999 | Perrin |
| 5,884,808 A | 3/1999 | Muderlak et al. |
| 5,908,140 A | 6/1999 | Muderlak |
| 5,922,247 A | 7/1999 | Shoham et al. |
| 5,924,597 A | 7/1999 | Lynn |
| 5,924,606 A | 7/1999 | Huizing |
| 5,938,076 A | 8/1999 | Ganzeboom |
| 5,946,209 A | 8/1999 | Eckel et al. |
| 5,962,930 A | 10/1999 | Cluff et al. |
| 5,964,403 A | 10/1999 | Miller et al. |
| 6,000,658 A | 12/1999 | McCall, Jr. |
| 6,006,957 A | 12/1999 | Kunesh |
| 6,026,987 A | 2/2000 | Burnett et al. |
| 6,029,659 A | 2/2000 | O'Connor |
| 6,036,108 A | 3/2000 | Chen |
| 6,039,212 A | 3/2000 | Singh |
| D425,190 S | 5/2000 | Morikawa |
| D426,293 S | 6/2000 | Tounsi et al. |
| 6,092,912 A | 7/2000 | Nelson |
| D432,637 S | 10/2000 | Mertens |
| D433,113 S | 10/2000 | Cole |
| D433,193 S | 10/2000 | Gaw et al. |
| D434,482 S | 11/2000 | Cole |
| 6,142,339 A | 11/2000 | Blacker et al. |
| 6,145,712 A | 11/2000 | Benoist |
| 6,151,529 A | 11/2000 | Batko |
| D435,098 S | 12/2000 | Kemmis et al. |
| 6,158,486 A | 12/2000 | Olson et al. |
| D436,398 S | 1/2001 | Steiner |
| 6,182,904 B1 | 2/2001 | Ulczynski et al. |
| D439,320 S | 3/2001 | Lee |
| 6,196,218 B1 | 3/2001 | Voges |
| 6,206,238 B1 | 3/2001 | Ophardt |
| 6,216,925 B1 | 4/2001 | Garon |
| 6,220,293 B1 | 4/2001 | Rashidi |
| 6,237,461 B1 | 5/2001 | Poole |
| 6,237,812 B1 | 5/2001 | Fukada |
| 6,249,717 B1 | 6/2001 | Nicholson et al. |
| 6,254,065 B1 | 7/2001 | Ehrensperger et al. |
| 6,264,548 B1 | 7/2001 | Payne, Jr. et al. |
| 6,267,297 B1 | 7/2001 | Contadini et al. |
| 6,293,442 B1 | 9/2001 | Mollayan |
| D449,229 S | 10/2001 | Mohary et al. |
| 6,296,172 B1 | 10/2001 | Miller |
| 6,297,297 B1 | 10/2001 | Brookman et al. |
| 6,343,714 B1 | 2/2002 | Tichenor |
| 6,347,414 B2 | 2/2002 | Contadini et al. |
| 6,357,726 B1 | 3/2002 | Watkins |
| 6,361,752 B1 | 3/2002 | Demarest et al. |
| 6,371,450 B1 | 4/2002 | Davis et al. |
| 6,390,453 B1 | 5/2002 | Frederickson et al. |
| 6,394,153 B2 | 5/2002 | Skell et al. |
| 6,394,310 B1 | 5/2002 | Muderlak et al. |
| D458,359 S | 6/2002 | Blanchette |
| 6,409,093 B2 | 6/2002 | Ulczynski et al. |
| D460,544 S | 7/2002 | Garcia |
| 6,415,957 B1 | 7/2002 | Michaels et al. |
| 6,419,122 B1 | 7/2002 | Chown |
| 6,446,583 B2 | 9/2002 | Vieira |
| 6,454,127 B1 | 9/2002 | Suomela et al. |
| 6,454,185 B2 | 9/2002 | Fuchs |
| RE37,888 E | 10/2002 | Cretu-Petra |
| 6,461,325 B1 | 10/2002 | Delmotte et al. |
| 6,478,199 B1 | 11/2002 | Shanklin et al. |
| 6,499,900 B1 | 12/2002 | Brozell |
| D468,627 S | 1/2003 | Dampney |
| 6,510,561 B1 | 1/2003 | Hammond et al. |
| 6,516,796 B1 | 2/2003 | Cox et al. |
| 6,517,009 B2 | 2/2003 | Yahav |
| D471,970 S | 3/2003 | Gallagher et al. |
| 6,529,446 B1 | 3/2003 | de la Huerga |
| 6,533,141 B1 | 3/2003 | Petterson et al. |
| 6,540,155 B1 | 4/2003 | Yahav |
| 6,554,203 B2 | 4/2003 | Hess et al. |
| 6,567,613 B2 | 5/2003 | Rymer |
| D476,070 S | 6/2003 | Millán |
| 6,588,627 B2 | 7/2003 | Petterson et al. |
| RE38,207 E | 8/2003 | Benoist |
| D478,003 S | 8/2003 | Bodker et al. |
| D478,379 S | 8/2003 | Talenton et al. |
| 6,607,102 B1 | 8/2003 | Griese et al. |
| 6,610,254 B1 | 8/2003 | Furner et al. |
| D479,592 S | 9/2003 | Lammel et al. |
| 6,612,464 B2 | 9/2003 | Petterson et al. |
| 6,619,562 B2 | 9/2003 | Hamaguchi et al. |
| D480,300 S | 10/2003 | Lee |
| D480,638 S | 10/2003 | Lee |
| 6,644,507 B2 | 11/2003 | Borut et al. |
| D484,585 S | 12/2003 | Upson |
| 6,669,105 B2 | 12/2003 | Bryan et al. |
| 6,672,129 B1 | 1/2004 | Frederickson et al. |
| 6,688,492 B2 | 2/2004 | Jaworski et al. |
| 6,694,536 B1 | 2/2004 | Haygreen |
| 6,698,616 B2 | 3/2004 | Hidle et al. |
| 6,712,287 B1 | 3/2004 | Le Pesant et al. |
| D488,548 S | 4/2004 | Lablaine |
| D488,809 S | 4/2004 | Kamegi |
| 6,722,529 B2 | 4/2004 | Ceppaluni et al. |
| 6,739,479 B2 | 5/2004 | Contadini et al. |
| D491,798 S | 6/2004 | Buthier |
| 6,769,580 B2 | 8/2004 | Muderlak et al. |
| D496,719 S | 9/2004 | Song |
| 6,785,911 B1 | 9/2004 | Percher |
| 6,790,408 B2 | 9/2004 | Whitby et al. |
| 6,795,645 B2 | 9/2004 | Hygema et al. |
| 6,830,164 B2 | 12/2004 | Michaels et al. |
| 6,832,701 B2 | 12/2004 | Schiller |
| 6,834,847 B2 | 12/2004 | Bartsch et al. |
| 6,837,396 B2 | 1/2005 | Jaworski et al. |
| 6,843,465 B1 | 1/2005 | Scott |
| 6,877,636 B2 | 4/2005 | Speckhart et al. |
| 6,877,924 B1 | 4/2005 | Mears et al. |
| 6,889,872 B2 | 5/2005 | Herman et al. |
| 6,903,654 B2 | 6/2005 | Hansen et al. |
| D508,284 S | 8/2005 | Butler et al. |
| D508,558 S | 8/2005 | Wolpert et al. |
| 6,926,002 B2 | 8/2005 | Scarrott et al. |
| 6,926,172 B2 | 8/2005 | Jaworski et al. |
| 6,926,211 B2 | 8/2005 | Bryan et al. |
| D509,892 S | 9/2005 | McLeish |
| 6,938,796 B2 | 9/2005 | Blacker et al. |
| 6,948,192 B2 | 9/2005 | Hipponsteel |
| D510,423 S | 10/2005 | Caserta et al. |
| D511,452 S | 11/2005 | Dibnah et al. |
| 6,968,982 B1 | 11/2005 | Burns |
| D512,769 S | 12/2005 | Wefler |
| 6,971,560 B1 | 12/2005 | Healy et al. |

(56) References Cited

U.S. PATENT DOCUMENTS

| | | |
|---|---|---|
| 6,974,091 B2 | 12/2005 | McLisky |
| 6,978,914 B2 | 12/2005 | Furner et al. |
| 6,978,947 B2 | 12/2005 | Jin |
| 6,981,499 B2 | 1/2006 | Anderson et al. |
| 6,997,349 B2 | 2/2006 | Blacker et al. |
| 7,000,853 B2 | 2/2006 | Fugere |
| 7,011,795 B2 | 3/2006 | Thompson et al. |
| D519,623 S | 4/2006 | Wu |
| 7,021,499 B2 | 4/2006 | Hansen et al. |
| 7,032,782 B1 | 4/2006 | Ciavarella et al. |
| D521,621 S | 5/2006 | Slater |
| D535,004 S | 1/2007 | Furner et al. |
| D535,377 S | 1/2007 | Caserta et al. |
| D535,378 S | 1/2007 | Caserta et al. |
| 7,160,515 B2 | 1/2007 | Murdell et al. |
| 7,168,273 B2 | 1/2007 | Neergaard et al. |
| 7,182,227 B2 | 2/2007 | Poile et al. |
| D537,929 S | 3/2007 | Muderlak et al. |
| D538,915 S | 3/2007 | Anderson et al. |
| 7,195,139 B2 | 3/2007 | Jaworski et al. |
| D539,892 S | 4/2007 | Caserta et al. |
| D541,400 S | 4/2007 | Heijdenrijk |
| 7,201,294 B2 | 4/2007 | Carlucci et al. |
| 7,207,500 B2 | 4/2007 | Hudson et al. |
| D543,461 S | 5/2007 | Mongeon et al. |
| 7,215,084 B1 | 5/2007 | Sharrah et al. |
| 7,222,758 B1 | 5/2007 | Scheindel |
| 7,223,166 B1 | 5/2007 | Wiseman, Sr. et al. |
| 7,223,361 B2 | 5/2007 | Kvietok et al. |
| D544,085 S | 6/2007 | Schriner et al. |
| D546,434 S | 7/2007 | Barraclough |
| D548,317 S | 8/2007 | Newton et al. |
| D548,824 S | 8/2007 | Christianson |
| D549,572 S | 8/2007 | Althouse et al. |
| 7,265,673 B2 | 9/2007 | Teller |
| D555,472 S | 11/2007 | Gedanke |
| 7,296,765 B2 | 11/2007 | Rodrian |
| 7,299,953 B2 | 11/2007 | McLisky |
| 7,308,790 B1 | 12/2007 | Bennett |
| 7,320,418 B2 | 1/2008 | Sassoon |
| D561,884 S | 2/2008 | Furner et al. |
| D561,885 S | 2/2008 | Furner et al. |
| D561,886 S | 2/2008 | Furner et al. |
| 7,341,169 B2 | 3/2008 | Bayer |
| 7,344,123 B2 | 3/2008 | Pankhurst et al. |
| 7,365,810 B2 | 4/2008 | Gotoh et al. |
| 7,398,013 B2 | 7/2008 | He et al. |
| 7,407,065 B2 | 8/2008 | Hooks et al. |
| 7,437,930 B2 | 10/2008 | Lasserre et al. |
| 7,461,650 B1 | 12/2008 | Rand |
| 7,481,380 B2 | 1/2009 | Kvietok et al. |
| 7,497,354 B2 | 3/2009 | Decottignies et al. |
| 7,509,955 B2 | 3/2009 | Cole et al. |
| 7,538,473 B2 | 5/2009 | Blandino et al. |
| 7,540,433 B2 | 6/2009 | Fleming et al. |
| 7,584,907 B2 | 9/2009 | Contadini et al. |
| 7,597,099 B2 | 10/2009 | Jones et al. |
| 7,610,118 B2 | 10/2009 | Schramm et al. |
| 7,628,339 B2 | 12/2009 | Ivir et al. |
| 7,654,416 B2 | 2/2010 | Bruining et al. |
| 7,670,479 B2 | 3/2010 | Arett et al. |
| 7,686,191 B1 | 3/2010 | Burns |
| 7,687,744 B2 | 3/2010 | Walter et al. |
| 7,722,807 B2 | 5/2010 | Keller, Jr. et al. |
| 7,735,694 B2 | 6/2010 | Brown et al. |
| 7,739,479 B2 | 6/2010 | Bordes et al. |
| 7,762,714 B2 | 7/2010 | Freeman et al. |
| 7,837,065 B2 | 11/2010 | Furner et al. |
| 7,954,667 B2 | 6/2011 | Furner et al. |
| 7,981,367 B2 | 7/2011 | Kvietok et al. |
| 8,016,207 B2 | 9/2011 | Kvietok et al. |
| 2001/0020450 A1 | 9/2001 | Vieira |
| 2002/0020756 A1 | 2/2002 | Yahav |
| 2002/0074349 A1 | 6/2002 | Michaels |
| 2003/0079744 A1 | 5/2003 | Bonney et al. |
| 2003/0132254 A1 | 7/2003 | Giangreco |
| 2004/0011885 A1 | 1/2004 | McLisky |
| 2004/0028551 A1 | 2/2004 | Kvietok et al. |
| 2004/0033171 A1 | 2/2004 | Kvietok et al. |
| 2004/0035949 A1 | 2/2004 | Elkins et al. |
| 2004/0074935 A1 | 4/2004 | Chon |
| 2004/0155056 A1 | 8/2004 | Yahav |
| 2004/0219863 A1 | 11/2004 | Willacy |
| 2004/0265164 A1 | 12/2004 | Woo et al. |
| 2005/0004714 A1 | 1/2005 | Chen |
| 2005/0067439 A1 | 3/2005 | Furner |
| 2005/0201944 A1 | 9/2005 | Kvietok et al. |
| 2005/0224596 A1 | 10/2005 | Panopoulos |
| 2005/0234402 A1 | 10/2005 | Collins et al. |
| 2006/0011737 A1 | 1/2006 | Amenos et al. |
| 2006/0037532 A1 | 2/2006 | Eidson |
| 2006/0060615 A1 | 3/2006 | McLisky |
| 2006/0076366 A1 | 4/2006 | Furner et al. |
| 2006/0083632 A1 | 4/2006 | Hammond et al. |
| 2006/0137619 A1 | 6/2006 | Dodman et al. |
| 2006/0151546 A1 | 7/2006 | McLisky |
| 2006/0153733 A1 | 7/2006 | Sassoon |
| 2006/0175357 A1 | 8/2006 | Hammond |
| 2006/0191955 A1 | 8/2006 | McLisky |
| 2007/0036673 A1 | 2/2007 | Selander |
| 2007/0080172 A1 | 4/2007 | Tyrrell et al. |
| 2007/0138326 A1 | 6/2007 | Hu |
| 2007/0158359 A1 | 7/2007 | Rodrian |
| 2007/0172382 A1 | 7/2007 | Uchiyama et al. |
| 2007/0199952 A1 | 8/2007 | Carpenter et al. |
| 2008/0069725 A1 | 3/2008 | Kvietok et al. |
| 2008/0210772 A1 | 9/2008 | Pearce et al. |
| 2009/0185950 A1 | 7/2009 | Woo et al. |
| 2010/0163639 A1 | 7/2010 | Pankhurst et al. |
| 2010/0243674 A1 | 9/2010 | Furner et al. |
| 2011/0076185 A1 | 3/2011 | Hammond et al. |

FOREIGN PATENT DOCUMENTS

| | | |
|---|---|---|
| AU | 659805 | 4/1992 |
| AU | 4932300 | 11/2000 |
| AU | 752399 | 7/2001 |
| DE | 19803696 | 8/1999 |
| DE | 103 92 689 | 4/2005 |
| DE | 103 92 794 | 6/2005 |
| EP | 038 598 | 10/1981 |
| EP | 0274785 B1 | 8/1990 |
| EP | 401060 | 12/1990 |
| EP | 0641727 A2 | 8/1995 |
| EP | 676133 | 10/1995 |
| EP | 0719234 B1 | 7/1996 |
| EP | 757 006 | 2/1997 |
| EP | 0956868 B1 | 11/1999 |
| EP | 1076014 B2 | 2/2001 |
| EP | 1184083 | 3/2002 |
| EP | 1214105 B1 | 6/2002 |
| EP | 1316514 | 6/2003 |
| EP | 1370304 B1 | 12/2003 |
| EP | 1382399 | 1/2004 |
| EP | 1407790 | 4/2004 |
| EP | 1430958 | 6/2004 |
| EP | 1522506 | 4/2005 |
| EP | 1547505 B1 | 6/2005 |
| EP | RCD0004052380001 A1 | 9/2005 |
| EP | 1695720 | 8/2006 |
| EP | 1726315 | 11/2006 |
| EP | 1848649 B1 | 10/2007 |
| EP | 1848650 B1 | 10/2007 |
| FR | 2671294 | 1/1991 |
| GB | 1033025 A | 6/1966 |
| GB | 2094407 | 9/1982 |
| GB | 2248888 | 4/1992 |
| GB | 2305261 | 4/1997 |
| GB | 2375710 | 11/2002 |
| GB | 2392438 B | 3/2004 |
| GB | 2392439 B | 3/2004 |
| GB | 2392440 B | 3/2004 |
| JP | 62171766 | 7/1987 |
| JP | 3114467 | 5/1991 |

(56) References Cited

FOREIGN PATENT DOCUMENTS

| | | |
|---|---|---|
| JP | 3159652 | 7/1991 |
| JP | 06170286 | 6/1994 |
| JP | 10085313 | 4/1998 |
| JP | 200070797 | 3/2000 |
| JP | 2002-113398 | 4/2002 |
| JP | 2004-331517 | 11/2004 |
| JP | 2007-246528 | 9/2007 |
| KR | 10-0284158 B1 | 9/2000 |
| WO | WO 88/05758 | 8/1988 |
| WO | WO 91/15409 | 10/1991 |
| WO | WO 95/19304 | 7/1995 |
| WO | WO 95/29106 | 11/1995 |
| WO | 9603218 A1 | 2/1996 |
| WO | 9630726 A1 | 10/1996 |
| WO | 9846280 A2 | 10/1998 |
| WO | WO 99/34266 | 7/1999 |
| WO | WO 00/47335 | 8/2000 |
| WO | WO 00/64498 | 11/2000 |
| WO | WO 00/64802 | 11/2000 |
| WO | WO 00/75046 | 12/2000 |
| WO | WO 00/78467 | 12/2000 |
| WO | WO 01/07703 | 2/2001 |
| WO | WO 01/21226 | 3/2001 |
| WO | 0125730 A1 | 4/2001 |
| WO | WO 01/26448 | 4/2001 |
| WO | WO 01/66157 | 9/2001 |
| WO | WO 02/40177 | 5/2002 |
| WO | WO 02/40376 | 5/2002 |
| WO | WO 02/072161 | 9/2002 |
| WO | WO 02/079679 | 10/2002 |
| WO | WO 02/087976 | 11/2002 |
| WO | WO 02/094014 | 11/2002 |
| WO | WO 03/005873 | 1/2003 |
| WO | WO 03/037748 | 5/2003 |
| WO | WO 03/037750 | 5/2003 |
| WO | WO 03/042068 | 5/2003 |
| WO | WO 03/062094 | 7/2003 |
| WO | WO 03/062095 | 7/2003 |
| WO | WO 03/068412 | 8/2003 |
| WO | WO 03/068413 | 8/2003 |
| WO | 03086947 A1 | 10/2003 |
| WO | WO 03/086902 | 10/2003 |
| WO | WO 03/086947 | 10/2003 |
| WO | WO 03/099682 | 12/2003 |
| WO | WO 03/104109 | 12/2003 |
| WO | WO 2004/002542 | 1/2004 |
| WO | WO 2004/043502 | 5/2004 |
| WO | WO 2004/110507 | 6/2004 |
| WO | WO 2004/067963 | 8/2004 |
| WO | WO 2004/073875 | 9/2004 |
| WO | WO 2004/081303 | 9/2004 |
| WO | WO 2004/093927 | 11/2004 |
| WO | WO 2004/093928 | 11/2004 |
| WO | WO 2004/105816 | 12/2004 |
| WO | WO 2004/105817 | 12/2004 |
| WO | WO 2004/105818 | 12/2004 |
| WO | WO 2005/001212 | 1/2005 |
| WO | WO 2005/014060 | 2/2005 |
| WO | WO 2005/018691 | 3/2005 |
| WO | WO 2005/023679 | 3/2005 |
| WO | WO 2005/072059 | 8/2005 |
| WO | WO 2005/072522 | 8/2005 |
| WO | 2005113420 A2 | 12/2005 |
| WO | WO 2006/012248 | 2/2006 |
| WO | WO 2006/044416 | 4/2006 |
| WO | WO 2006/058433 | 6/2006 |
| WO | WO 2006/064187 | 6/2006 |
| WO | WO 2006/084317 | 8/2006 |
| WO | WO 2006/104993 | 10/2006 |
| WO | WO 2006/105652 | 10/2006 |
| WO | WO 2006/108043 | 10/2006 |
| WO | 2006114532 A1 | 11/2006 |
| WO | WO 2007/029044 | 3/2007 |
| WO | WO 2007/045828 | 4/2007 |
| WO | WO 2007/052016 | 5/2007 |
| WO | WO 2007/064188 | 6/2007 |
| WO | WO 2007/064189 | 6/2007 |
| WO | WO 2007/064197 | 6/2007 |
| WO | WO 2007/064199 | 6/2007 |
| WO | WO 2007/132140 | 11/2007 |
| WO | WO 2007/146332 | 12/2007 |
| WO | WO 2008/056131 | 5/2008 |
| WO | WO 2009/103738 | 8/2009 |
| WO | WO 2010/145038 | 12/2010 |

OTHER PUBLICATIONS

Web Page "AirWick FreshMatic" @ http://www.cleanware.co.nz/product_info.php?products_id=159 dated Mar. 7, 2005 (1 page).
Web Page http://www.cleanware.co.nz/images/client/AirWick2.jpg dated Mar. 7, 2005 (1 page).
Web Page "FreshMatic Refill Citrus" @ http://www.cleanware.co.nz/product_info.php?products_id=161 dated Mar. 7, 2005 (1 page).
Web Page "AirWick Frequently Asked Questions" @ http://www.airwick.co.uk/faqs_page/faqs.html dated Mar. 7, 2005 (6 pages).
Web Page "AirWick Personalize Your Atmosphere with the Fragrances You Love" @ http://www.airwick.co.uk/product_page/product.html dated Mar. 7, 2005 (5 pages).
Extended European Search Report for EP Appl. No. 07011131.5-2425 (based on PCT/US2005/036576) dated Aug. 27, 2007.
Extended European Search Report for EP Appl. No. 07011132.3-2425 (based on PCT/US2005/036576) dated Aug. 27, 2007.
PCT/US08/003317 International Search Report and Written Opinion dated Nov. 6, 2008.
Office Action dated Jul. 7, 2010, for U.S. Appl. No. 11/725,402, filed Mar. 19, 2007, inventors Carpenter et al.
PCT/US05/036576 International Preliminary Report on Patentability and Written Opinion of the International Searching Authority dated Apr. 1, 2007.
European Office Action for EP 08 726 782.9-1268 dated Jun. 8, 2010.
Office Action dated Sep. 29, 2010, for U.S. Appl. No. 12/796,473, dated Jun. 8, 2010, inventors Furner et al.
International Search Report and Written Opinion dated Oct. 12, 2009 for corresponding international application PCT/US2008/005889, 18 pages.
Office Action (Non-Final Rejection) dated Dec. 21, 2011; U.S. Appl. No. 13/235,192.
Office Action (Final Rejection) dated Jul. 6, 2012; U.S. Appl. No. 13/235,192.
Office Action (Non-Final Rejection) dated Aug. 12, 2009; U.S. Appl. No. 11/247,793.
Office Action (Non-Final Rejection) dated Jan. 20, 2010; U.S. Appl. No. 11/247,793.
Office Action (Requirement for Restriction/Election) dated Mar. 30, 2009; U.S. Appl. No. 11/247,793.
Office Action (Final Rejection) dated Jun. 9, 2011; U.S. Appl. No. 11/725,402.
Office Action (Non-Final Rejection) dated Dec. 23, 2010; U.S. Appl. No. 11/725,402.

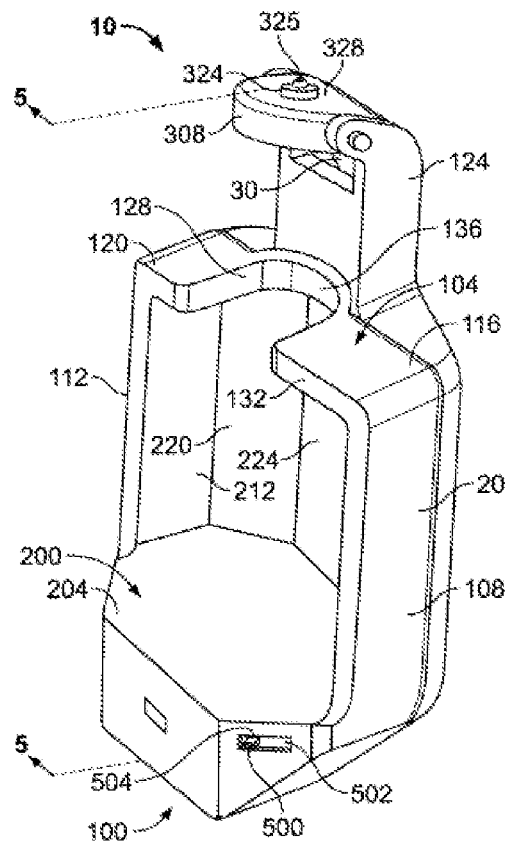
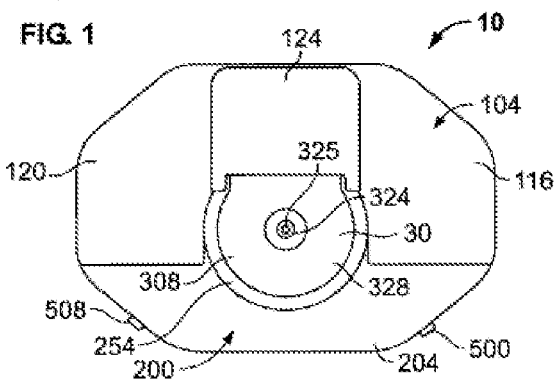

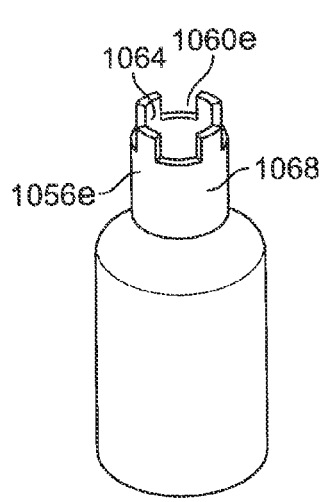 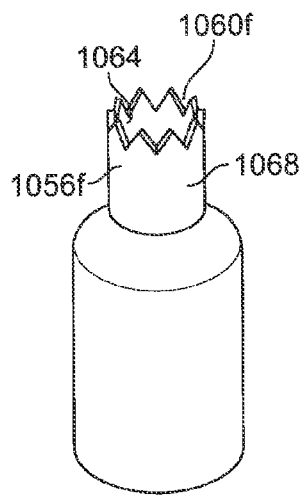 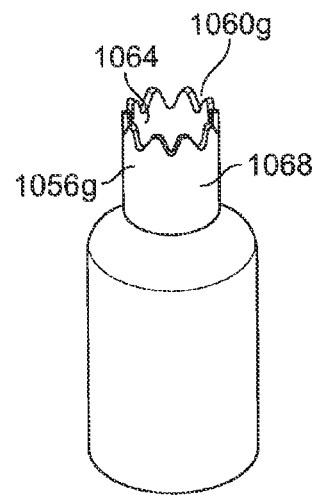
FIG. 40　　　　　　FIG. 41　　　　　　FIG. 42
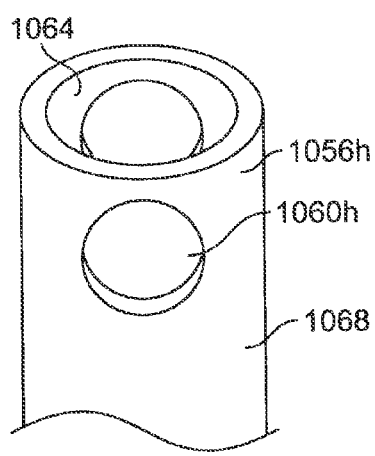 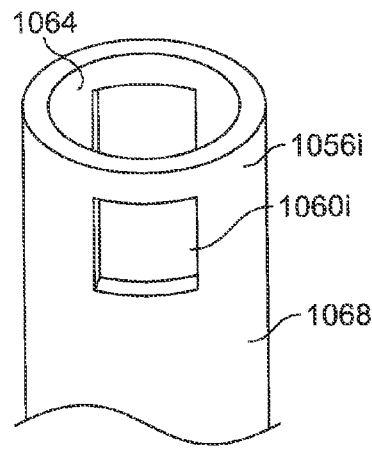
FIG. 43　　　　　　FIG. 44

COMPACT SPRAY DEVICE

CROSS REFERENCE TO RELATED APPLICATIONS

This application is a continuation application of U.S. patent application Ser. No. 13/235,192, filed Sep. 16, 2011, which is a continuation of U.S. patent application Ser. No. 11/725,402, filed Mar. 19, 2007, which claims the benefit of U.S. patent application Ser. No. 11/247,793, filed Oct. 11, 2005, and U.S. Provisional Application No. 60/617,950, filed Oct. 12, 2004.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present disclosure relates to discharging a fluid from a spray device, and more particularly, to a method and apparatus for discharging a liquid through a nozzle of an aerosol container.

2. Description of the Background

An automatic discharge device for an aerosol container containing a pressurized fluid within a housing typically includes an actuator mechanism for engaging a nozzle of the aerosol container. In a specific example, a motor displaces the actuator mechanism in response to input received from a sensor, wherein the displacement causes the actuator mechanism to engage the nozzle of the aerosol container and discharge the pressurized fluid therefrom.

Hill et al. U.S. Pat. No. 4,544,086 discloses an ornament that includes a valving mechanism for discharging a pressurized fluid from an aerosol can. The valving mechanism comprises an actuator bar that contacts and depresses a nozzle of the aerosol can to release the pressurized fluid therefrom. The released pressurized fluid acts upon a diaphragm within the valving mechanism to force hydraulic fluid from a first chamber into a second chamber, wherein the fluid entering the second chamber raises a piston. The rising piston forces the actuator bar to rise therewith and disengage from the nozzle, thereby terminating fluid discharge from the can. The pressurized fluid within the valving mechanism is thereafter controllably released to permit the piston to drop so that the actuator rod engages the nozzle again.

Lynn U.S. Pat. No. 5,924,597 discloses a fragrance dispensing apparatus for use in a multi-room building having an existing HVAC system ventilated by a forcing fan. The apparatus includes a plurality of fragrance containers, a plurality of solenoids, a plurality of programmable timers, and a single fan timer.

Mollayan U.S. Pat. No. 6,293,442 discloses a timed spray dispenser for distributing a liquid deodorizer from an aerosol can disposed within a housing of the dispenser. A lever arm is pivotably mounted on the housing and includes a first end that engages a spray valve of the can and a second end that engages an eccentric cam, wherein the eccentric cam is rotated by a timer controlled motor. As the eccentric cam is rotated, the cam pivots the lever arm, thereby causing the first end to depress the spray valve and discharge the contents of the can.

Chown U.S. Pat. No. 6,419,122 discloses an apparatus for dispensing a chemical from an aerosol container. The container is provided with a magnetic material and a solenoid coil extending around the container. Energization of the solenoid coil causes the container to move upwardly from a non-dispensing position to a dispensing position.

Borut et al. U.S. Pat. No. 6,644,507 discloses an automatic air freshener that utilizes an electric motor coupled to an actuator cam, wherein a lobe of the actuator cam engages an end of an aerosol canister. The cam causes the canister to slide upwardly through a frame toward a housing aperture, wherein a valve of the canister is depressed within the housing aperture to open the valve and dispense the contents of the canister therefrom.

SUMMARY OF THE INVENTION

According to one embodiment of the present invention, an automatic discharge device includes a housing retaining two containers therein. An actuator arm is attached to the housing and movable between first and second positions. A drive unit is provided for automatically moving the actuator arm into one of the first and second positions in response to a signal from at least one of a timer, a sensor, and a manual switch. The movement of the actuator arm actuates a valve stem of one of the two containers in one of the first and second positions. The actuator arm is adapted to spray fluid disposed in an interior of the two containers.

According to a different embodiment of the present invention, an automatic discharge device includes a housing having a recess adapted to retain a container therein. A combination of sensors is provided for detecting an environmental condition. An actuator arm is attached to the housing and movable between first and second positions. A drive unit is provided for automatically moving the actuator arm into one of the first and second positions in response to a signal from at least one of the combination of sensors, a timer, and a manual switch. The movement of the actuator arm actuates a valve stem of the container allowing a fluid disposed in an interior of the container to be dispensed and exited from the housing in an upward direction through an upper end of the housing.

BRIEF DESCRIPTION OF THE DRAWINGS

FIG. 1 is an isometric view of one type of dispenser wherein batteries and a fluid container are omitted therefrom;

FIG. 2 is a plan view of the dispenser of FIG. 1 with a fluid container inserted therein;

FIGS. 36-44 are enlarged isometric views of alternative valve stems that may be used in conjunction with the embodiments described herein.

DETAILED DESCRIPTION OF THE DRAWINGS

Figure 3:
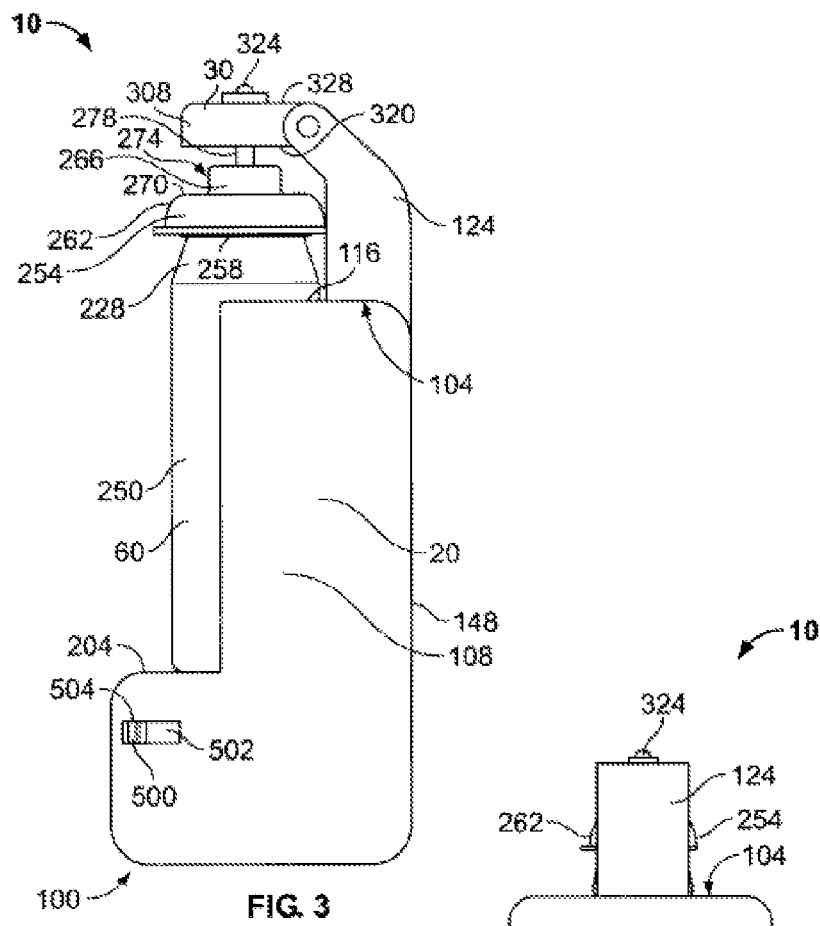
FIG. 3 is a side elevational view of the dispenser of FIG. 2.
Figure 4:
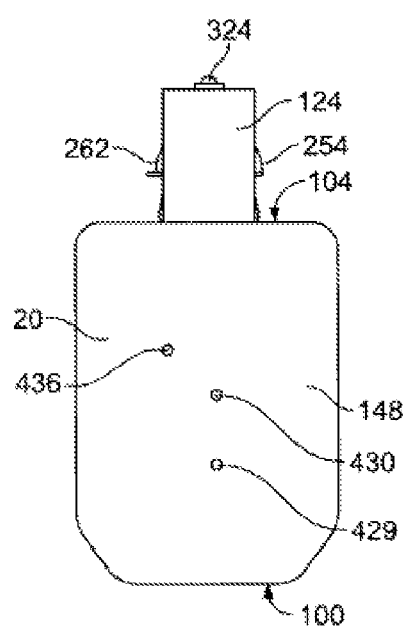
FIG. 4 is a rear elevational view of the dispenser of FIG. 2.

FIGS. 1-6 depict one embodiment of a dispenser 10. The dispenser 10 generally comprises a housing 20, an actuator arm 30, and a drive unit 40. A container 60 is disposed within the housing 20 of the dispenser 10. The dispenser 10 discharges fluid from the container 60 upon occurrence of a particular condition. The condition could be the manual activation of the device or the automatic activation of the device in response to an elapsed time interval or signal from a sensor. The fluid may be a fragrance or insecticide disposed within a carrier liquid, a deodorizing liquid, or the like. For example, the fluid may comprise OUST®, an air and carpet sanitizer for household, commercial, and institutional use, or GLADE®, a household deodorant, both sold by S. C. Johnson and Son, Inc., of Racine, Wis. The fluid may also comprise other actives, such as sanitizers, air fresheners, odor eliminators, mold or mildew inhibitors, insect repellents, and the like, or that have aromatherapeutic properties. The fluid alternatively comprises any fluid known to those skilled in the art that can be dispensed from a container. The dispenser 10 is therefore adapted to dispense any number of different fluid formulations.

The housing 20 of the embodiment depicted in FIGS. 1-6 comprises a base portion 100 and a top portion 104. First and second sidewalls 108, 112, respectively, extend between the base portion 100 and the top portion 104. Further, the top portion 104 includes first and second shoulders 116, 120, respectively, wherein the first shoulder 116 extends inwardly from the first sidewall 108 and the second shoulder 120 extends inwardly from the second sidewall 112. The present embodiment also includes an actuator arm cover 124 that extends upwardly from the top portion 104 to cover the actuator arm 30. In a preferred embodiment, the actuator arm cover 124 is contoured to have a shape similar to that of the actuator arm 30.

Figure 5:
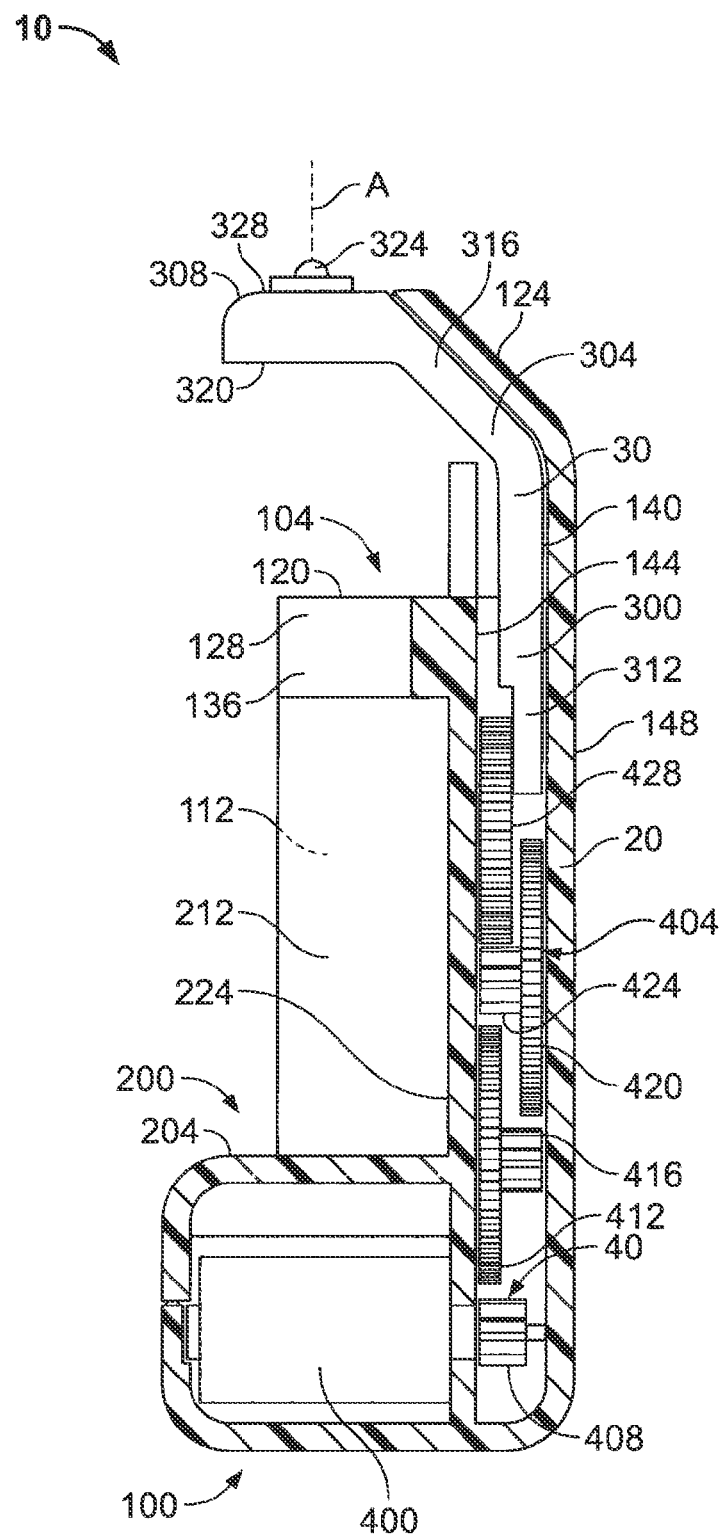
FIG. 5 is a cross-sectional view taken generally along the lines 5-5 of FIG. 1 depicting the dispenser.
Figure 6:
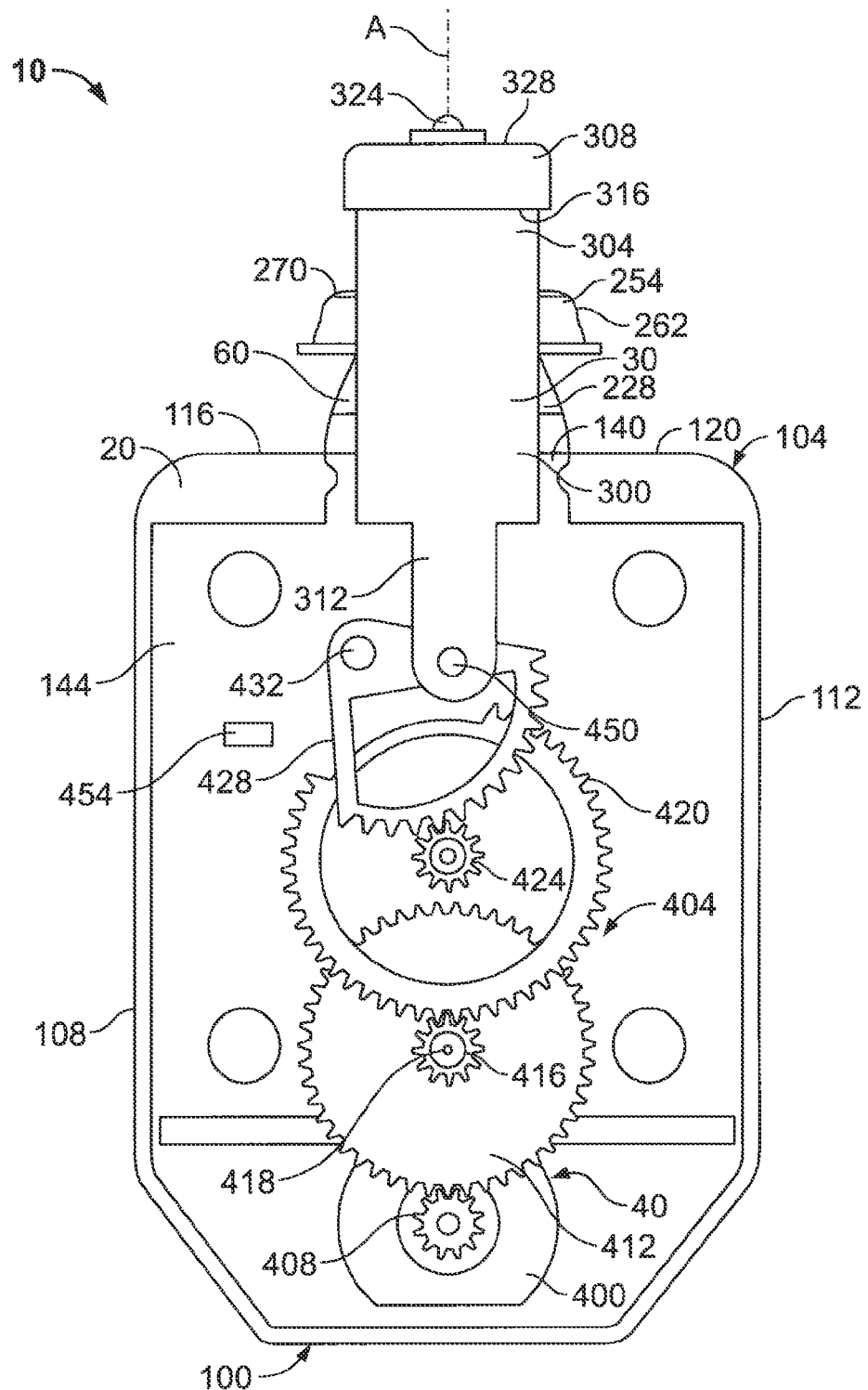
FIG. 6 is a view similar to that of FIG. 4, except that the rear panel of the dispenser is removed to show a drive unit and an actuator arm.

A slot 128 is disposed between the first and second shoulders 116, 120 of the top portion 104 as may be seen in FIG. 1. The slot 128 is substantially cylindrical and is open on a front side 132. An inner wall 136 defining the slot 128 is contoured to allow a portion of the container 60 to easily nest therein. FIGS. 5 and 6 show that the top portion 104 also includes a channel 140 adjacent the slot 128, wherein the channel 140 is disposed between an inner rear panel 144 and an outer rear panel 148 of the housing 20.

With particular reference to FIGS. 1-4, the container 60 is inserted through the front side 132 of the housing 20 and into a recess 200 defined in part by a bottom surface 204, side surfaces 208 and 212, angled surfaces 216 and 220, and a rear surface 224. Further, a neck 228 of the container 60 is inserted into the slot 128, which assists in the alignment and/or securing of the container 60. Two AA batteries 232 are also inserted into the housing 20 through the front side 132 thereof, similar to the embodiment of FIGS. 8 and 9 discussed below. The batteries 232 are secured by an interference fit between respective positive and negative terminals.

The container 60 may be an aerosol container or a pump-type sprayer container of any size and volume known to those skilled in the art. However, the container 60 is preferably an aerosol container comprising a body 250 with a mounting cup 254 crimped to a top end 258 thereof. The mounting cup 254 is generally cylindrical in shape and includes an outer wall 262 that extends circumferentially therearound. In some instances, the neck 228 of the container 60 is disposed below the mounting cup 254, wherein the neck 228 is angled inwardly with respect to the mounting cup 254 and the remaining area of the body 250. A pedestal 266 also extends upwardly from a central portion of a base 270 of the mounting cup 254. A valve assembly 274 within the container 60 includes a valve stem 278, wherein a distal end 282 of same extends through the pedestal 266. If desired, a button or other actuator (not shown) may also be assembled onto the distal end 282 of the valve stem 278. When the distal end 282 of the valve stem 278 is depressed the valve assembly 274 is opened and the contents of the container 60 are discharged through an orifice 286 of the valve stem 278. The contents of the container 60 may be discharged in a continuous or metered dose. Further, the discharging of the contents of the container 60 may be effected in any number of ways, e.g., a discharge comprising a partial metered dose, a discharge through a partial opening of the valve assembly 274, multiple consecutive discharges, etc.

With regard to FIGS. 5 and 6, the actuator arm 30 includes a main portion 300, an intermediate portion 304, and an overhang portion 308. A depending attachment portion 312 that includes a bore extends downwardly from the main portion 300. The attachment portion 312 is coupled to a section of the drive unit 40, as noted in greater detail hereinafter. The main portion 300 is disposed within the channel 140 and is substantially parallel with the outer rear panel 148 of the housing 20. The intermediate portion 304 of the actuator arm 30 extends laterally and upwardly from the main portion 300. An upper end 316 of the intermediate portion 304 is therefore farther from the outer rear panel 148 and the top portion 104 of the housing 20 than the main portion 300. The overhang portion 308 of the actuator arm 30 extends from the upper end 316 of the intermediate portion 304 toward the front side 132 of the housing 20. The overhang portion 308 is substantially transverse to the main portion 300. Further, at least a section of the overhang portion 308 is disposed above the slot 128.

Prior to opening the valve assembly 274 and releasing the contents of the container 60, the actuator arm 30 and overhang portion 308 are positioned in a pre-actuation position. Preferably, when the actuator arm 30 and the overhang portion 308 are disposed in the pre-actuation position, the distal end 282 of the valve stem 278 is spaced slightly from or just in contact with a lower side 320 of the overhang portion 308. Alternatively, at this point, the overhang portion 308 may partially depress the valve stem 278 a distance insufficient to open the valve assembly 274.

A dispensing bore 324 terminating at an orifice 325 is provided within the overhang member 308 that extends from an upper side 328 of the overhang portion 308 to the lower side 320 thereof and allows for fluid communication between the container 60 and the outside atmosphere. While the dispensing bore 324 could have any geometrical shape, FIGS. 1-6 depict that the dispensing bore 324 has a circular cylindrical shape. The dispensing bore 324 preferably has a diameter of about 20 mils. A longitudinal axis A of the dispensing bore 324 is preferably oriented in a direction normal to a plane of the base portion 100 of the housing 20. Thus, the contents of the container 60 are discharged upwardly through the dispensing bore 324 and into the atmosphere when the valve assembly 274 is opened. If desired, the dispensing bore 324 may instead be L-shaped or have any other nonlinear shape to direct the contents of the container 60 in a direction other than upwards. Still further, the cross-sectional shape and/or diameter of the dispensing bore 324, and/or the orifice 286 and/or the orifice 325 may be modified to obtain any desired spray pattern, or to alter the swirling and/or mechanical breakup of the discharged liquid, as should be evident to one of ordinary skill in the art.

The actuator arm 30 depresses the valve stem 278 through motion imparted thereto by the drive unit 40. The drive unit 40 includes a drive motor 400 in association with a reduction gear train 404 as may be seen in FIGS. 5 and 6. The drive motor 400 is mounted within the base portion 100 of the housing 20 beneath the bottom surface 204 of the recess 200.

The drive motor 400 includes a motor gear 408, otherwise referred to as a first pinion, which is directed toward the outer rear panel 148 of the housing 20. The motor gear 408 meshes with a drive gear 412, wherein the drive gear 412 includes a second pinion 416 that is rotatable about an axle 418. The second pinion 416 of the drive gear 412 meshes with an idler gear 420, wherein the idler gear 420 includes a third pinion 424 that is rotatable about an axle 426. The third pinion 424 of the idler gear 420 meshes with a lever gear 428. The drive, idler, and lever gears 412, 420, 428, respectively, are disposed between the inner rear panel 144 and the outer rear panel 148 of the housing 20. The axles 418 and 426 are molded extrusions extending from the inner rear panel 144, wherein distal ends thereof extend into holes 429 and 430, respectively, of the outer rear panel 148.

The lever gear 428 rotates about an axle 432 that extends from the inner rear panel 144 to a hole 436 of the outer rear panel 148. The lever gear 428 is further connected to the attachment portion 312 by a pin 450 at a point offset from the axle 432. When the lever gear 428 is rotated via the gear reduction train 404 and the drive motor 400 in a clockwise direction (as seen in FIG. 6), the actuator arm 30 is pulled downwardly toward a discharge position. Conversely, when the lever gear 428 is rotated in a counter-clockwise direction, the actuator arm 30 is pushed upwardly toward the pre-actuation position. A molded rib 454 projecting from the inner rear panel 144 interferes with the lever gear 428 when the actuator arm 30 has been pulled into the discharge position.

The actuator arm 30 is moved to the discharge position by pulling same downwardly to a particular point such that the valve stem 278 is depressed and the valve assembly 274 is opened, thereby allowing discharge of fluid through the valve assembly 274. The particular point is selected to coincide with a partial or full depression of the valve stem 278. Fully depressing the valve stem 278 releases either a full metered discharge or a continuous discharge of the container contents, while partially depressing the valve stem 278 results in a partial metered or partial continuous discharge of the container contents. Preferably, although not necessarily, the actuator arm 30 is held in the discharge position for a length of time (referred to hereinafter as a "spraying period"). The duration of the spraying period could range anywhere from a fraction of a second to one or more seconds. Indeed, if desired, the actuator arm 30 could be held in the discharge position until all of the container contents are exhausted. At the end of the spraying period, the drive motor 400 is deenergized and the spring-biased valve stem moves the actuator arm 30 to the pre-actuation position and terminates further spraying. The movement of the actuator arm 30 back to the pre-actuation position is aided by a bounce effect created by deenergizing the drive motor 400 after the lever gear 428 is in forced contact with the molded rib 454. If desired, the actuator arm 30 may be moved to and from the discharge position multiple times in response to the occurrence of a single condition to provide for multiple sequential discharges. Multiple sequential discharges may be beneficial when a single discharge from a continuously discharging container with a long spraying period is not desired, or when a single discharge from a metered container is insufficient.

The drive unit 40 of the dispenser 10 preferably utilizes a high torque rated motor with higher rpm speed relative to prior art dispensers. In some instances, the drive motor 400 is 5 to 10 times faster than motors used in prior art dispensers. A more energy efficient system is obtained by running the drive motor 400 faster during the depression of the valve stem 278. This increase in efficiency is an unexpected result and is counterintuitive to the teachings of the prior art. Further, by placing a substantial portion of the drive unit 40 between the inner and outer rear panels 144, 148, the size of the dispenser 10 relative to prior art dispensers is significantly reduced. Still further, low-weight materials can be used (for example, the gears and motor pinion may be made of flexible urethane or thermoplastic), so that a low-weight dispenser 10 is obtained. The reduced size and weight permits the dispenser 10 to be placed almost anywhere in a home or business. Still further, the disclosed positioning of the drive unit 40 also has the advantage of making a dispenser 10 that is quieter relative to prior art dispensers. Also, the use of a flexible material or materials for the gears further reduces the noise coming from the drive unit 40.

FIG. 1 shows that the dispenser 10 includes a switch 500. The switch 500 has an off position 502 as seen in FIG. 1 and an on position 504 (to the left as seen in FIG. 1). When the switch 500 is moved to the on position, the dispenser 10 operates in an automatic timed mode of operation as noted in greater detail below in connection with FIG. 7. Depression of a further pushbutton switch 508 (FIG. 2) causes a manual spraying operation to be undertaken. The manual spraying option allows the user to override and/or supplement the automatic operation of the dispenser 10 when so desired.

Figure 7:
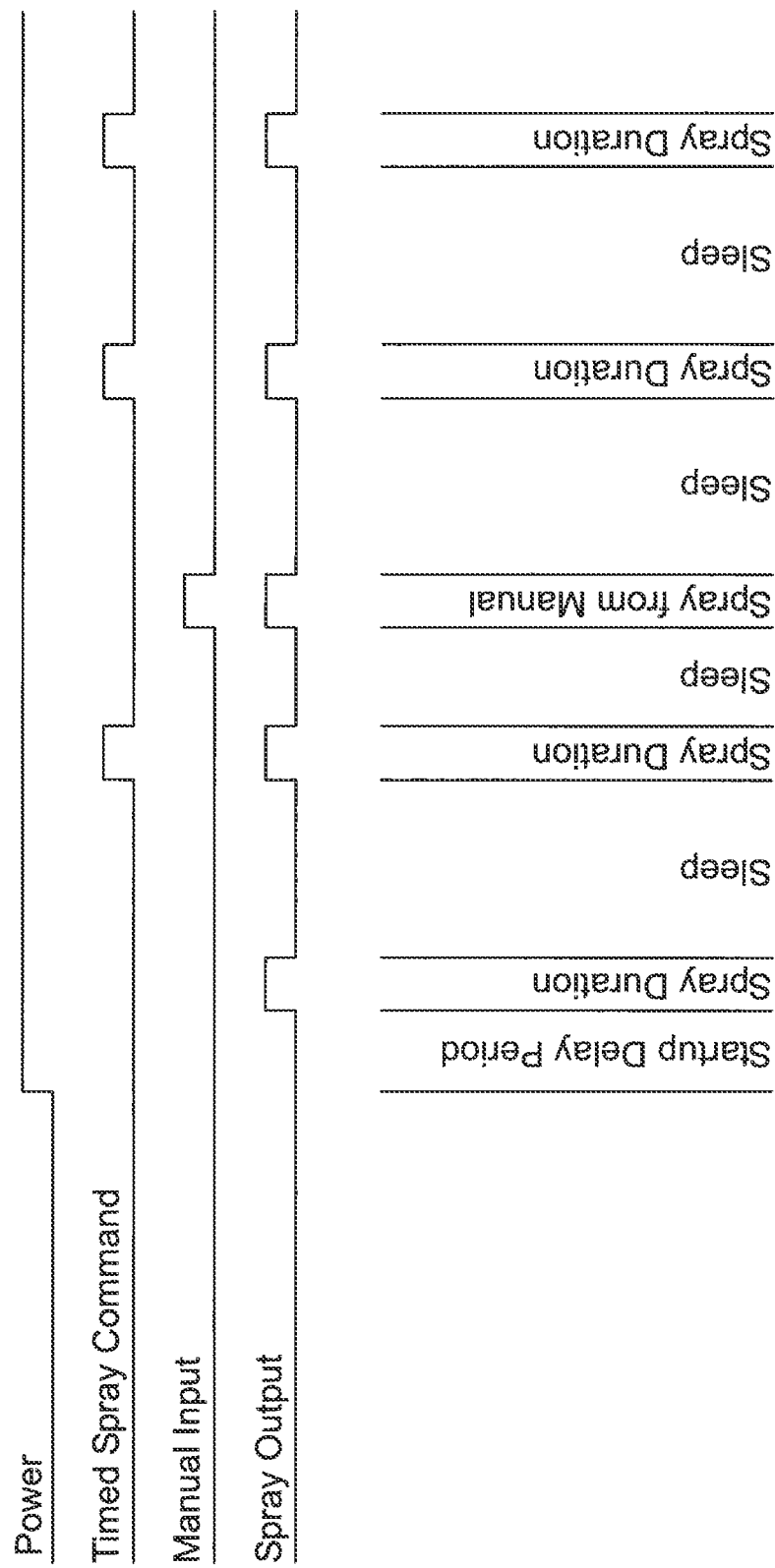
FIG. 7 is a timing diagram illustrating the operation of the dispenser of FIGS. 1-6 according to a first operational sequence.

FIG. 7 depicts a timing diagram of the present embodiment that illustrates operation of the dispenser 10 during use. Initially, the dispenser 10 is energized by moving the switch 500 to the on position whereupon the dispenser 10 enters a startup delay period. Upon completion of the startup delay period, the drive unit 40 is directed to discharge fluid from the dispenser 10 during a first spraying period. The startup delay period is preferably three seconds long. Upon completion of the first spraying period, the dispenser 10 enters a first sleep period that lasts a predetermined time interval, such as about four hours. Upon expiration of the first sleep period the drive unit 40 is actuated to discharge fluid during a second spraying period. Automatic operation thereafter continues with alternating sleep and spraying periods. At any time during a sleep period, the user can manually actuate the dispenser 10 for a selectable or fixed period of time by depressing the pushbutton switch 508. Upon termination of the manual spraying operation, the dispenser 10 initiates a further complete sleep period. Thereafter, a spraying operation is undertaken.

Figure 8:
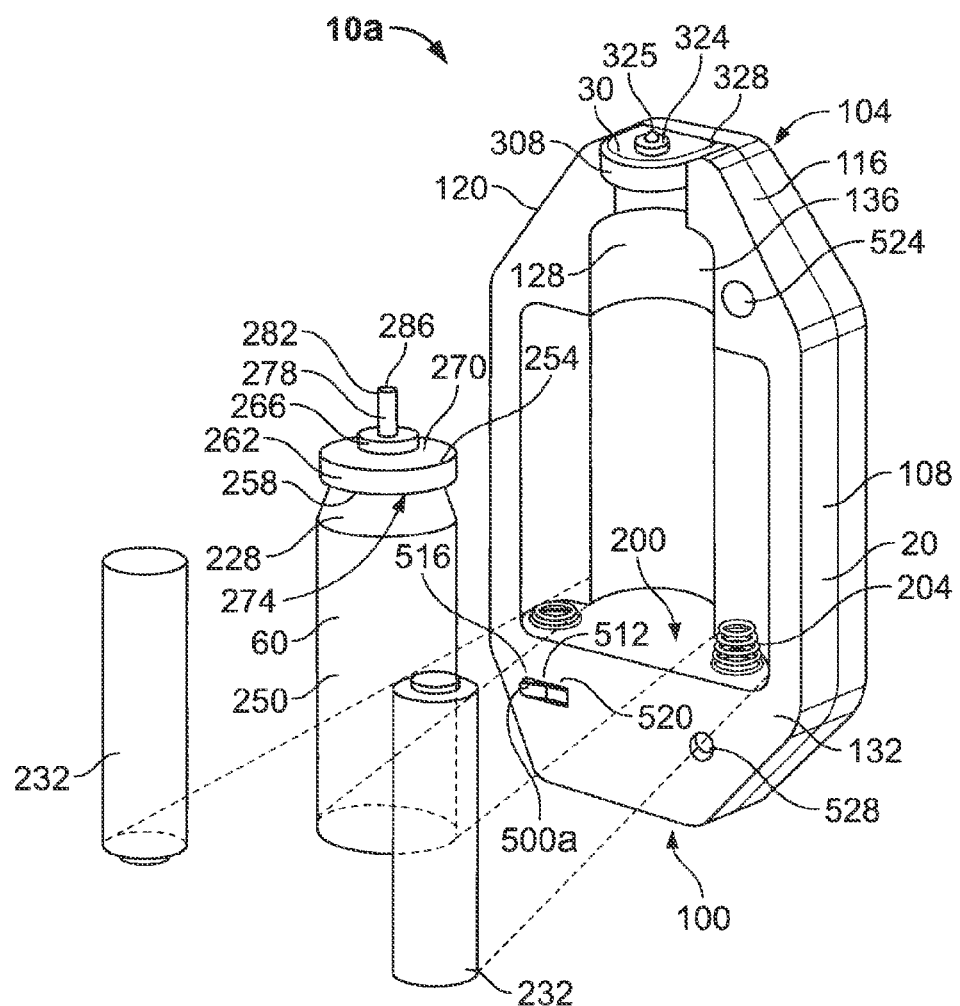
FIG. 8 is an exploded isometric view of another dispenser, an aerosol container, and two batteries.
Figure 9:
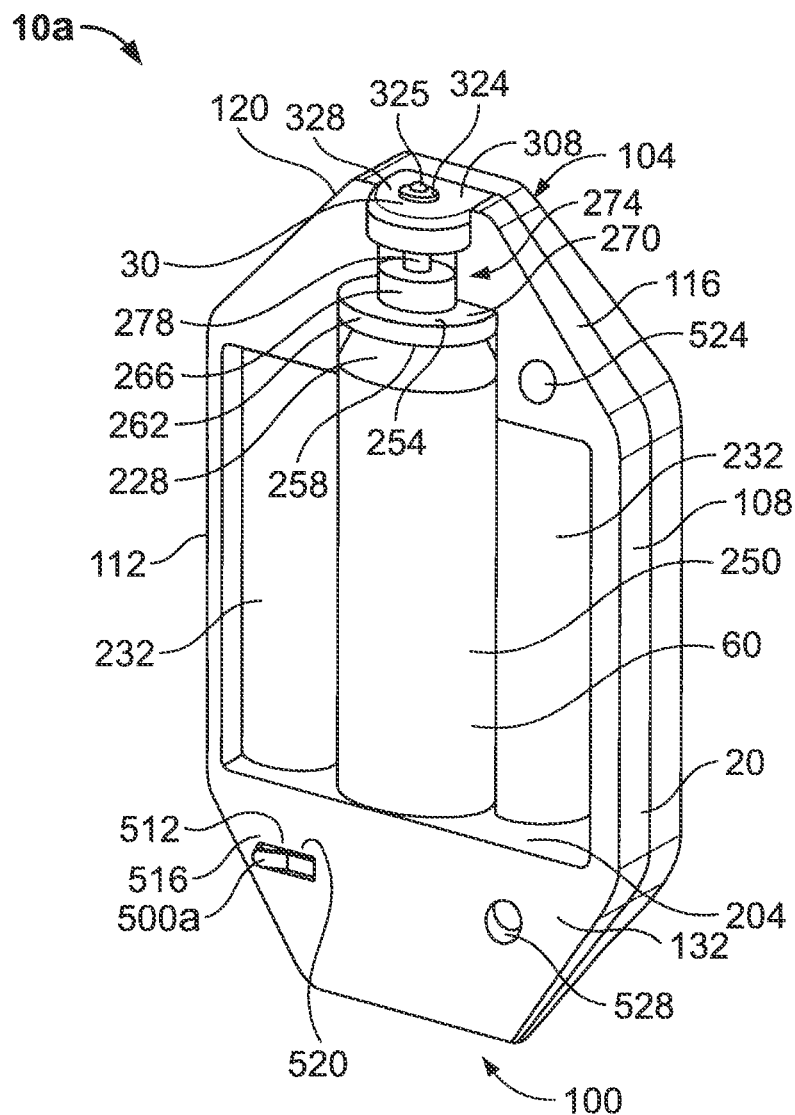
FIG. 9 is an isometric view illustrating the aerosol container and the two batteries placed into the dispenser of FIG. 8.

FIGS. 8 and 9 show another embodiment of a dispenser 10a. A switch 500a is preferably a toggle switch movable to one of three stable positions. When the switch 500a is in a center position 512 the dispenser 10a is deenergized. When the switch 500a is moved to a first on position 516, power is supplied to electrical components of the dispenser 10a and the dispenser 10a operates in a timed mode of operation, as described in connection with FIG. 7 hereinabove. Movement of the switch 500a to a second on position 520 energizes the electrical components of the dispenser 10a and causes the dispenser 10a to operate in a combined timed and sensing mode of operation responsive to the output of a sensor 524, as noted in greater detail hereinafter. A further switch 528 of the push-button type is also provided for manual activation of the drive unit 400, wherein the switch 528 may be depressed by the user to cause a spraying operation at any time, except when the dispenser 10a is off The switch 528 allows the user to manually override the automated activation of the dispenser 10a.

In the present embodiment, the sensor 524 is a photocell motion sensor. However, other commercially available motion detectors may be utilized with the present embodiment, e.g., a passive infrared or pyroelectric motion sensor, an infrared reflective motion sensor, an ultrasonic motion sensor, or a radar or microwave radio motion sensor. The photocell collects ambient light and allows a controller 532 (FIG. 11) to detect any changes in the intensity thereof. Filtering of the photocell output is undertaken by the controller 532. If the controller 532 determines that a threshold light condition has been reached, e.g., a predetermined level of change in light intensity, the controller 532 activates the drive unit 40. For example, if the dispenser 10a is placed in a lit bathroom, a person walking past the sensor 524 may block a sufficient amount of ambient light from reaching the sensor 524 to cause the controller 532 to activate the dispenser 10a and discharge a fluid.

Figure 10:
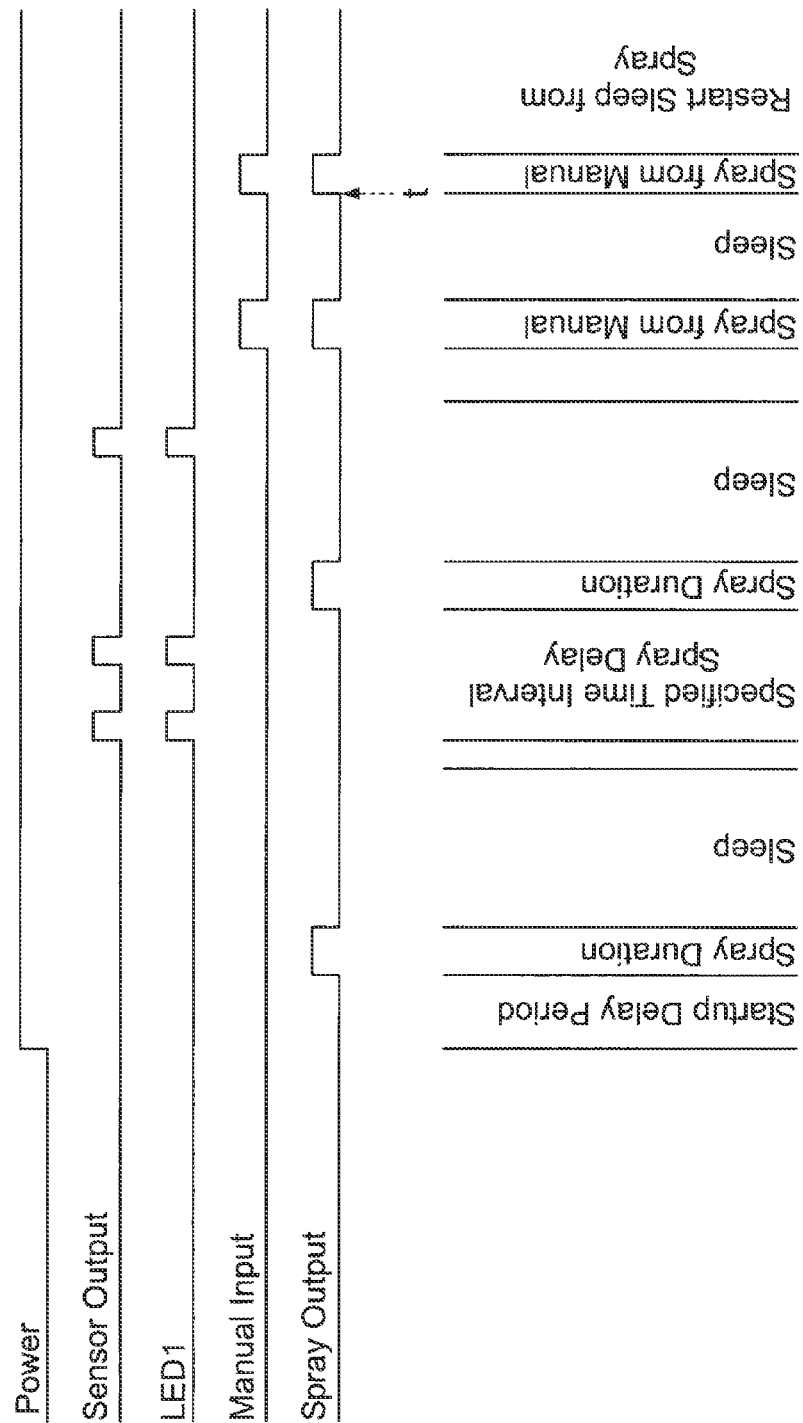
FIG. 10 is another timing diagram illustrating the operation of the dispenser of FIGS. 8 and 9 according to a second operational sequence.

When the switch 500a is moved to the second on position 520, the dispenser 10a preferably operates as shown by the timing diagram of FIG. 10. Moving the switch 500a to the second on position 520 initially causes the dispenser 10a to enter a startup delay period. Upon expiration of the startup delay period, fluid is discharged from the dispenser 10a during a first spraying period. Upon completion of the first spraying period, the dispenser 10a enters a first sleep mode, during which spraying is prevented, even if motion is detected by the sensor 524. Thereafter, if the sensor 524 detects motion after expiration of the first sleep period and sends a sensor output signal to a controller 532, the controller 532 times a specified time interval. The specified time interval is preferably approximately two minutes long. Once the specified time interval has elapsed, the dispenser 10a discharges fluid during a second spraying period. The delay in spraying causes the dispenser 10a to wait the specified time interval following detection of motion to spray the fluid so that the occupant of the room has time to move away from the dispenser 10a and/or leave the room. Upon completion of the second spraying period, the dispenser 10a enters a second sleep period. The dispenser 10a is prevented from automatically activating again in response to detection of motion until the second sleep period has elapsed. The sleep periods prevent over-spraying by numerous automatic activations that may occur in heavily trafficked areas. It is preferred that each sleep period last about one hour.

At any time the user can initiate a manual spraying operation by manually actuating the switch 528 to discharge fluid during a manual spraying period. Upon completion of the manual spraying period, the dispenser 10a undergoes a complete sleep period. Thereafter, the dispenser 10a alternates between sleep periods and spray periods initiated by motion detection following expiration of a sleep period. A full sleep period follows every spray period, regardless of whether the spray period was responsive to motion detection or actuation of the switch 528. For example, the timing diagram of FIG. 10 illustrates another manual actuation at a time t and the dispenser 10a thereafter entering a full sleep period.

In any of the embodiments disclosed herein, the sleep periods may all be of the same duration and a sleep period is automatically undertaken following termination of a spray operation, whether the spray operation is initiated manually or automatically. Also in the preferred embodiments, the lengths of the spray periods are all equal. If desired, one or more of the sleep periods may be longer or shorter than other sleep periods and/or one or more of the spray periods may be longer or shorter than other spray periods. In addition, the startup delay period may be omitted and the first spraying operation can be undertaken immediately upon power-up of the dispenser. Still further, the control methodology can be modified to cause spraying operations to be periodically undertaken at equal or unequal intervals without regard to whether a manual spraying operation has been undertaken.

If desired, the dispenser 10a may be modified to be operable only during particular hours, e.g., during the day or only at night.

In a different embodiment, the sensor 524 is a vibration or tilt sensor known to those skilled in the art. By placing the dispenser 10a on a door or a toilet bowl, the closing or flushing of same, respectively, causes the sensor 524 to develop an output signal that is delivered to the controller 532. Thereafter, the dispenser 10a discharges fluid in a manner similar to that described above.

It is also envisioned that numerous other types of sensors 524 could be used with the presently disclosed dispenser 10a. More specifically, a sound activated sensor could activate the dispenser 10a upon or following detection of a sound, such as a toilet flushing or a door closing. Alternatively, a water level sensor may be particularly useful to activate the dispenser 10a when a toilet is flushed or at a certain time following flushing. In a different embodiment, the sensor 524 is a pressure sensor that activates the drive unit 40 at or following the time that a person steps on a specified area of a floor or sits on a toilet seat. In yet another embodiment, a humidity sensor activates the dispenser 10a at or following the time when a toilet is flushed (thereby causing humidity in the vicinity of the toilet to increase) or when the air is too dry or too moist. Still further, a temperature sensor that registers changes in ambient temperature in the vicinity of a toilet may be provided to activate the dispenser 10a at or following the time when a person is near the toilet and thereby raises the ambient temperature in the vicinity thereof. Such a temperature sensor could instead be disposed in a manner to sense temperature change when the water level of a toilet changes so that the dispenser 10a is activated when the toilet is flushed (or at a particular time following flushing). Finally, an odor sensor could detect certain molecules in areas such as a bathroom or kitchen and activate the dispenser 10a immediately or at a particular time following such detection. While it is preferred that only one of the sensors 524 be utilized, any combination of such sensors could be used, with the varying combinations being selected by an appropriate switch or switches. Further, the present listing of potential sensors 524 is not exhaustive but is merely illustrative of the different types of sensors 524 that can be used with the dispenser 10 described herein. Still further, the placement of the dispenser 10 is not confined to any of the specific examples described above. It is intended that the dispenser 10 be placed in any area where the dispensing of a fluid is required and/or where the sensor 524 is effective.

Figure 11:
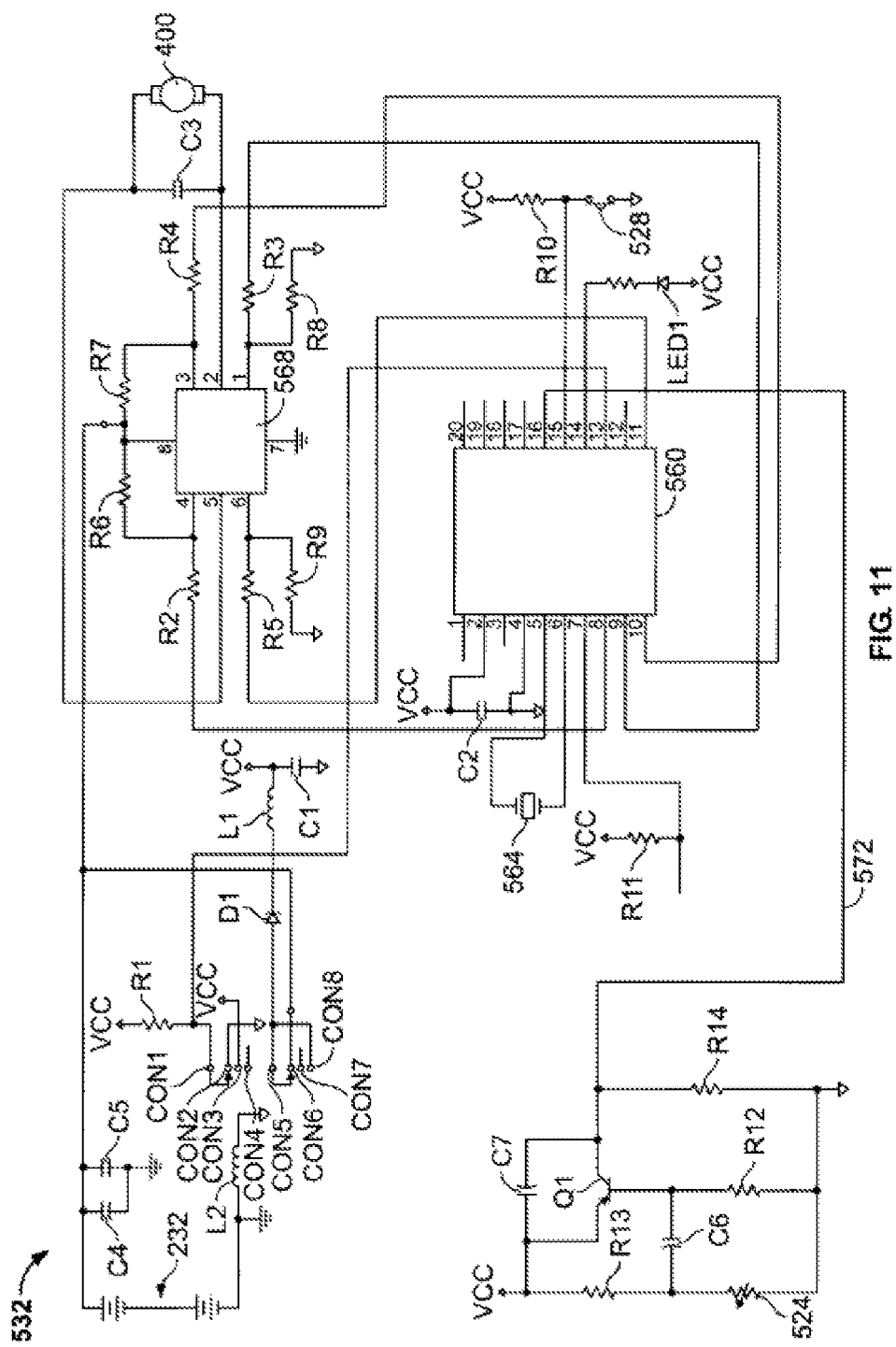
FIG. 11 is a schematic diagram showing an electrical circuit for controlling the motor of any of the dispensers disclosed herein.

Referring next to FIG. 11, a circuit for implementing the controller 532 includes an MSP43OF1121 microprocessor 560 manufactured by Texas Instruments. The integrated circuit 560 is actuable by the switch 500a. More specifically, the switch 500a is of the two-pole, three-throw type and includes contacts CON1-CON8. When the switch 500a is in the middle or off position, contacts CON2 and CON3 are connected to one another as are contacts CON6 and CON7. Accordingly, no power is supplied to the contact CON5 or the contact CON8, and hence, the various components illustrated in FIG. 11, including the integrated circuit 560, are off When the user moves the switch 500a to the first on position, the contacts CON2 and CON4 are connected to one another as are the contacts CON6 and CON8. The contact CON6 is connected to the positive terminal of series-connected batteries 232, and thus is at a potential of approximately three volts above ground. This voltage is delivered through the contact CON8, a diode D1, and an inductor L1 to develop a voltage VCC. A capacitor C1 is connected between the voltage VCC and ground. The LC circuit formed by the inductor L1 and the capacitor C1 smooth voltage variations so that the voltage VCC remains at a substantially constant level. The voltage VCC is applied to a pin 2 of the integrated circuit 560. Further, ground potential is supplied to a pin 4 of the integrated circuit 560. A capacitor C2 is coupled between the pin 2 and the pin 4 of the integrated circuit 560.

A crystal 564 is connected between a pin 5 and a pin 6 of the integrated circuit 560. The crystal 564 establishes a time base for an internal clock of the integrated circuit 560.

A pin 13 of the integrated circuit 560 is connected to the contact CON1 and a first end of a resistor R1 wherein a second end of the resistor R1 receives the voltage VCC. Pins 8-11 of the integrated circuit 560 are coupled through resistors R2-R5 to pins 4, 1, 8, and 3, respectively, of a further integrated circuit 568, comprising a ZHB6718 SM-8 Bipolar Transistor H-Bridge integrated circuit sold by Zetex PLC of the United Kingdom. Resistors R6 and R7 are connected between the pins 4 and 8, respectively, of the integrated circuit 568 and the positive terminal of the series-connected batteries 232. The pins 1 and 3 of the integrated circuit 568 are connected by resistors R8 and R9, respectively, to ground. In addition, the positive terminal of the series-connected batteries 232 and ground are coupled to pins 6 and 2, respectively, of the integrated circuit 568. Pins 5 and 7 of the integrated circuit 568 are coupled to first and second terminals of the drive motor 400. A capacitor C3 is coupled across the drive motor 400.

A pin 15 of the integrated circuit 560 is connected to a junction between a resistor R10 and the second switch 528. The resistor R10 and the switch 528 are connected between the voltage VCC and ground.

In addition to the foregoing, a negative terminal of the series-connected batteries 232 is connected through an inductor L2 to ground. The integrated circuit 560 can be reset by applying a low state signal to a pin 7. A resistor R11 is connected between the pin 7 and the voltage VCC. A pair of capacitors C4 and C5 are connected between positive and negative terminals of the series-connected batteries 232.

When the switch 500a is in the second on position, a high state signal is supplied to the pin 13 of the integrated circuit 560, thereby causing operation in the timed mode as shown in FIG. 7. This high state signal instructs the integrated circuit 560 to begin the startup delay period. Upon expiration of the startup delay period, appropriate signals are developed at the pins 8-11 of the integrated circuit 560 at the beginning of the first spray period to cause the integrated circuit 568 to energize the drive motor 400 in a first direction. The drive motor 400 rotates the motor gear 408, in turn rotating the gears 412, 420, and 428, thereby moving the actuator arm 30 downwardly. This downward movement depresses the valve stem 278 of the container 60, thereby causing a spraying operation. This motor energization continues for a predetermined amount of time, at the end of which the signals developed at the pins 8-11 of the integrated circuit 560 change to opposite states. The integrated circuit 568 then energizes the drive motor 400 in a second direction, thereby reversing the downward force on the actuator arm 30 and the valve stem 278 of the container 60. The actuator arm 30 and the valve stem 278 then move upwardly in response to upward movement of the arm 30 and the upward force provided by the valve stem 278 so that further release of the contents of the container 60 is prevented.

Following the termination of spraying during the first spray period, the integrated circuit 560 enters the first sleep period. During this time low state signals are developed at the pins 8-11 of the integrated circuit 560 so that the drive motor 400 is kept in an off condition. Upon expiration of the first sleep period, the integrated circuit 560 again develops appropriate signals at the pins 8-11, thereby causing the integrated circuit 568 to energize the drive motor 400. As before, the actuator arm 30 and the valve stem 278 move downwardly, thereby discharging a spray of liquid from the container 60. At the end of this second spraying period, the integrated circuit 560 again develops opposite signals at the pins 8-11, thereby moving the arm 30 upwardly until an end-of-travel limit is reached, whereupon the signals at the pins 8-11 of the integrated circuit 560 all revert to a low state. The drive motor 400 is thus deenergized via the integrated circuit 568 and the integrated circuit 560 prevents further spraying until the expiration of the second sleep period. The integrated circuit 560 thereafter alternates between further spraying and sleep periods as noted above.

At any time during any of the sleep periods, a user can command manual spraying of the container 60 by depressing the switch 528. This action causes a signal developed at the pin 15 of the integrated circuit 560 to transition from a high state to a low state. When this transition is detected, the integrated circuit 560 energizes the drive motor 400 via the pins 8-11 and the integrated circuit 568. At the termination of the spraying operation, the integrated circuit 560 begins timing of a further sleep period, following which a spraying operation is again undertaken.

When the switch 500a is moved to the second on position, a high state signal is provided to the pin 13 of the integrated circuit 560, thereby causing the integrated circuit 560 to enter the combined timed/sensor mode of operation. In this mode of operation, the first spraying operation is undertaken following a startup delay period and a sleep period is initiated at the end of the spraying operation, as seen in FIG. 10.

As seen in FIG. 11, a motion detector circuit 570 includes the sensor 524 in the form of a photoresistor coupled between ground and a first end of an AC coupling capacitor C6. A second end of the capacitor C6 is coupled to a base electrode of a PNP bipolar transistor Q1. The base of the transistor Q1 is coupled to a first end of a biasing resistor R12. A second end of the biasing resistor R12 is coupled to ground. A further resistor R13 is coupled between an emitter electrode of the transistor Q1 and the photoresistor 524. A capacitor C7 is coupled across the emitter electrode and a source electrode of the transistor Q1. A resistor R14 is coupled between the source electrode and ground.

The resistor R13 and the photoresistor 524 act as a voltage divider. The changing resistance of the photoresistor 524 in response to changing light conditions causes a varying voltage to be developed at the junction between the resistor R13 and the photoresistor 524. An AC component of this varying voltage is delivered to the base electrode of the transistor Q1. The transistor Q1 is operated in the linear mode and the components C7 and R14 act as a low-pass filter. The component values are selected so that a signal is developed on a line 572 for each transition in light received by the photoresistor 524 occurring over a short interval. Thus, a signal is developed on the line 572 when a person passes in front of the photoresistor and again when the person moves sufficiently to unblock the photoresistor. No signal is developed on the line 572 when the light transition is developed over a long period of time, such as at dusk or dawn. Each time a signal is developed on the line 572, the integrated circuit 560 pulls the pin 14 thereof to a low voltage for a brief period of time, such as 0.25 second, to energize a light emitting diode LED1 (also seen in the embodiment of FIG. 12). The integrated circuit 560 uses either a high-to-low transition or a low-to-high transition in the signal on the line 572 as a trigger to cause a spraying operation, either immediately or after a delay period, provided that the circuit 560 is not in the sleep mode. The controller 532 operates in accordance with the timing diagram of FIG. 10 during this mode of operation.

Figure 12:
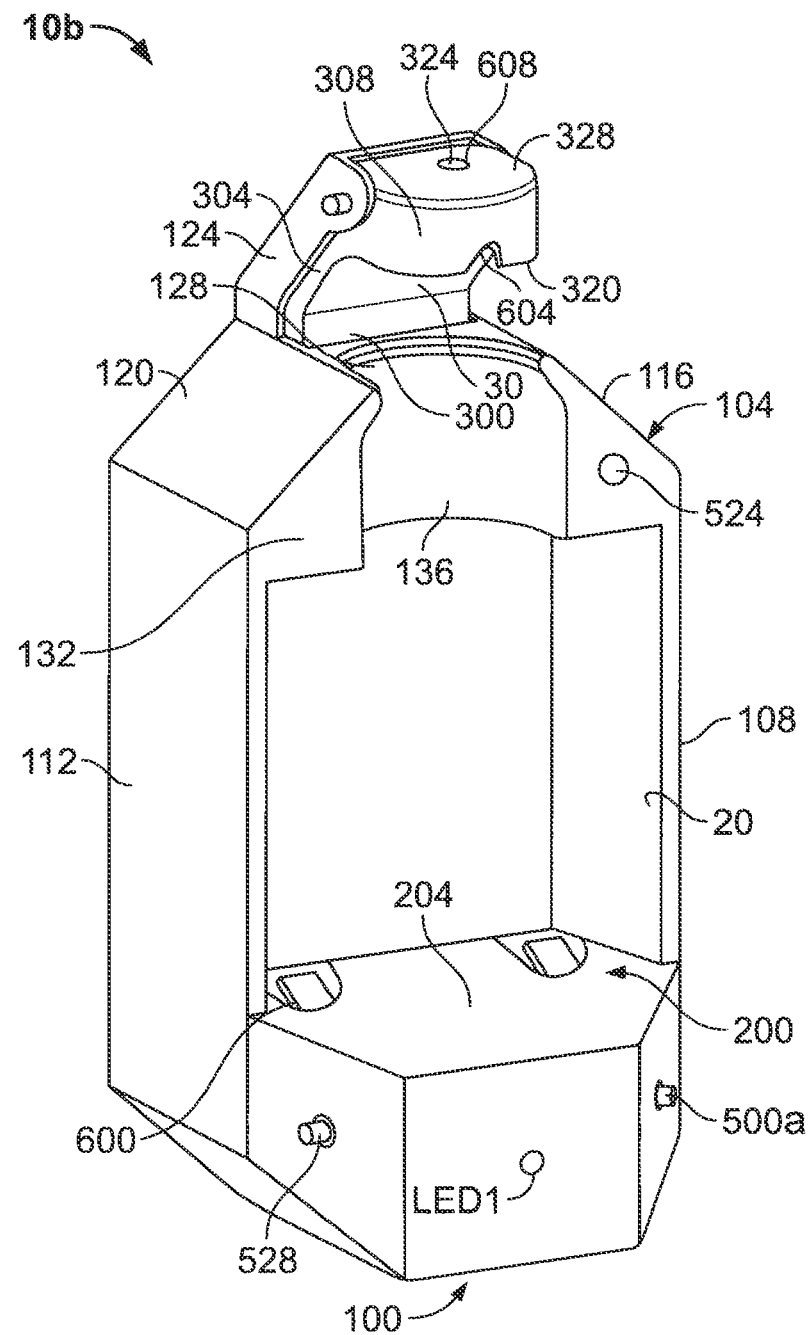
FIG. 12 is an isometric view of yet another dispenser.

FIG. 12 shows another embodiment incorporating the controller 532 and which is identical to the embodiment of FIGS. 8 and 9, except as noted below.

The embodiment of FIG. 12 includes two slots 600 disposed within the bottom surface 204 of the recess 200. The batteries 232 (not shown in FIG. 12) are secured by way of an interference fit between terminals within the two slots 600 and respective terminals on an opposing wall of the recess. The embodiment of FIG. 12 also includes a groove 604 within the overhang portion 308. The groove 604 faces the front side 132 of the housing 20 and is dimensioned to receive the valve stem 278 therein. The present embodiment further includes a recess (not shown) disposed on the lower side 320 of the overhang portion 308. The recess is sufficiently sized to allow entry of a portion of the distal end 282 of the valve stem 278. The recess acts as a centering mechanism to align the valve stem 278 with the second orifice 324 and/or as a directional guide for the discharged contents. A second recess 608 is disposed on the opposite side of the overhang portion 308. The recess 608 may have a cross-sectional size larger than the size of the dispensing bore 324. Further, the cross-sectional size of the recess 608 may vary, e.g., the recess 608 may have a circular shape with a diameter that is smaller adjacent the dispensing bore 324 than the diameter of the recess 608 adjacent the opposite side of the overhang portion 308. When the valve stem 278 is depressed by the downward motion of the overhang portion 308, the fluid dispensed from the container 60 traverses the recess, the dispensing bore 324, and the second recess 608 before being discharged into the atmosphere. The dispensing bore 324 and/or the second recess 608 may discharge the fluid in a direction normal to an axial length of the container 60 or at any angle therefrom.

With regard to the embodiments depicted in FIGS. 1-6, 8, 9, and 12, the dispensers 10, 10a, and 10b may have numerous varying characteristics. For example, the overhang portion 308 or the actuator arm 30 may impart a force onto any area of the valve stem 278 to depress or tilt same.

If desired, the slot 128 may be dimensioned to form an interference fit with the container 60. In yet another alternative, a portion of the container 60, such as the upper portion, is provided with a groove, protrusion, or any other engaging mechanism for interaction with a complementary protrusion, groove, or engaging mechanism, respectively, located on or within the inner wall 136 or any other wall of the dispenser. Further, the inner wall 136 may be angled or tapered inwardly (i.e., toward a center of the slot 128) from bottom to top. The tapering of the inner wall 136 provides for an engagement surface with the neck 228 or any other engagement member of the container 60. Some of the engaging mechanisms assist in keeping the container 60 within the recess 200 and in alignment with the actuator arm 30. Other engaging mechanisms allow for a broader spectrum of container sizes to be used with a single dispenser. For example, a dispenser that has an engaging mechanism for interaction with the neck of a container could hold and align a container having a bottom end thereof in contact with the bottom surface 204 of the recess 200, or a bottom end thereof suspended above the bottom surface 204 of the recess 200.

As a still further alternative, the motor 400 may be driven in two directions to open and close the valve assembly 274. In this case, when spraying is to be terminated, the motor is energized in a second direction to reverse the downward force on the actuator arm 30 and the valve stem 278. The actuator arm 30 and the valve stem 278 then move upwardly to the pre-actuation position in response to upward movement of the actuator arm 30 and the upward force provided by the valve assembly 274, at which time the valve assembly 274 of the container 60 is closed.

In yet another alternative, the axles 418, 426, and 432 are not molded into the inner rear panel 144. Instead, the axles 418, 426, and 432 are mounted into a steel or metal plate, wherein the axles 418, 426, and 432 cantilever from the plate to provide support and alignment.

Figure 45:
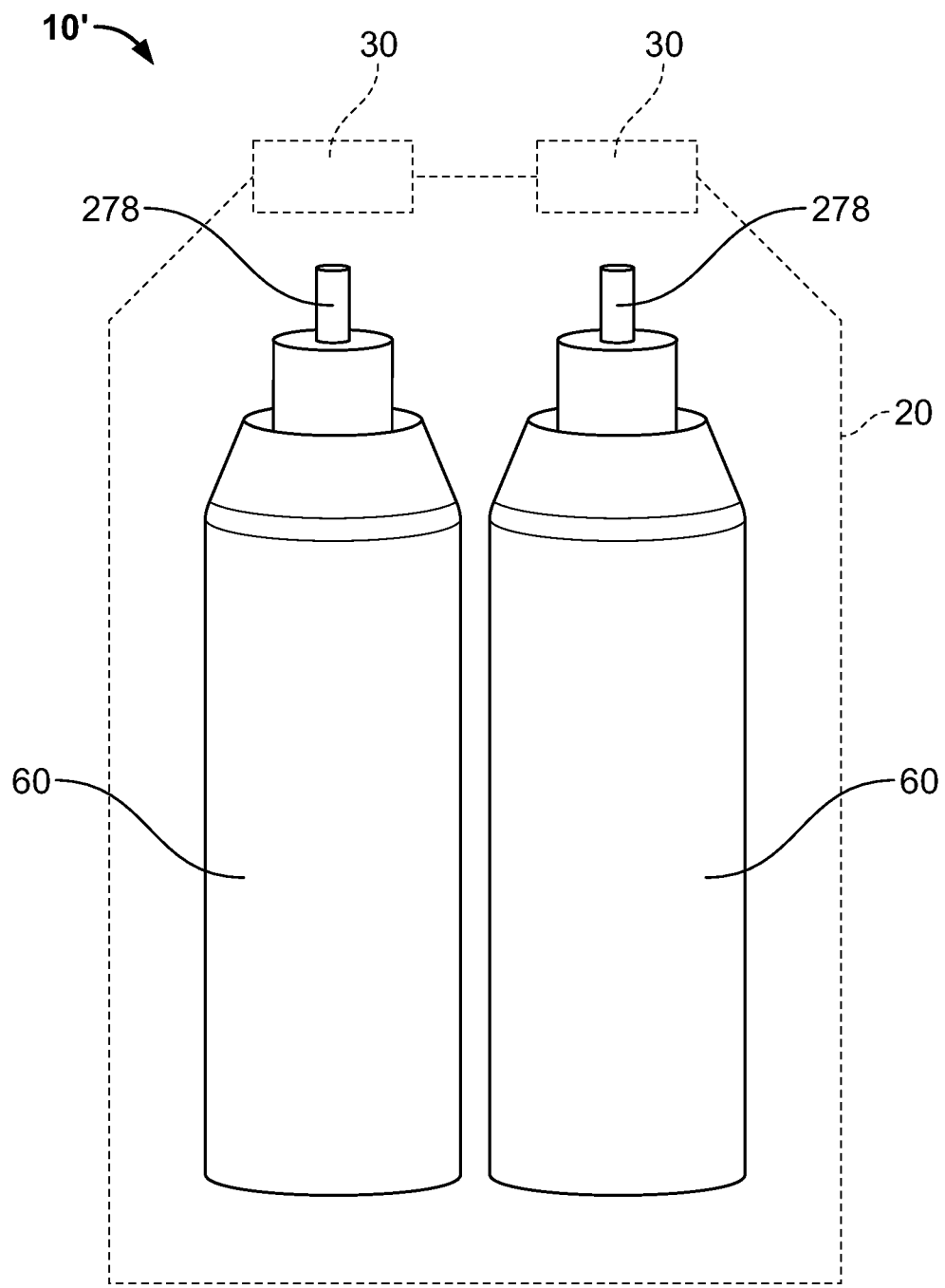
FIG. 45 is a schematic representation of another dispenser.

It is also envisioned that different alternatives of the dispenser may have the ability to hold and spray one or more containers having the same or different products (see FIG. 45). Further, the dispenser could spray the contents of the containers at the same time or at selected intervals and sequences.

Figure 13:
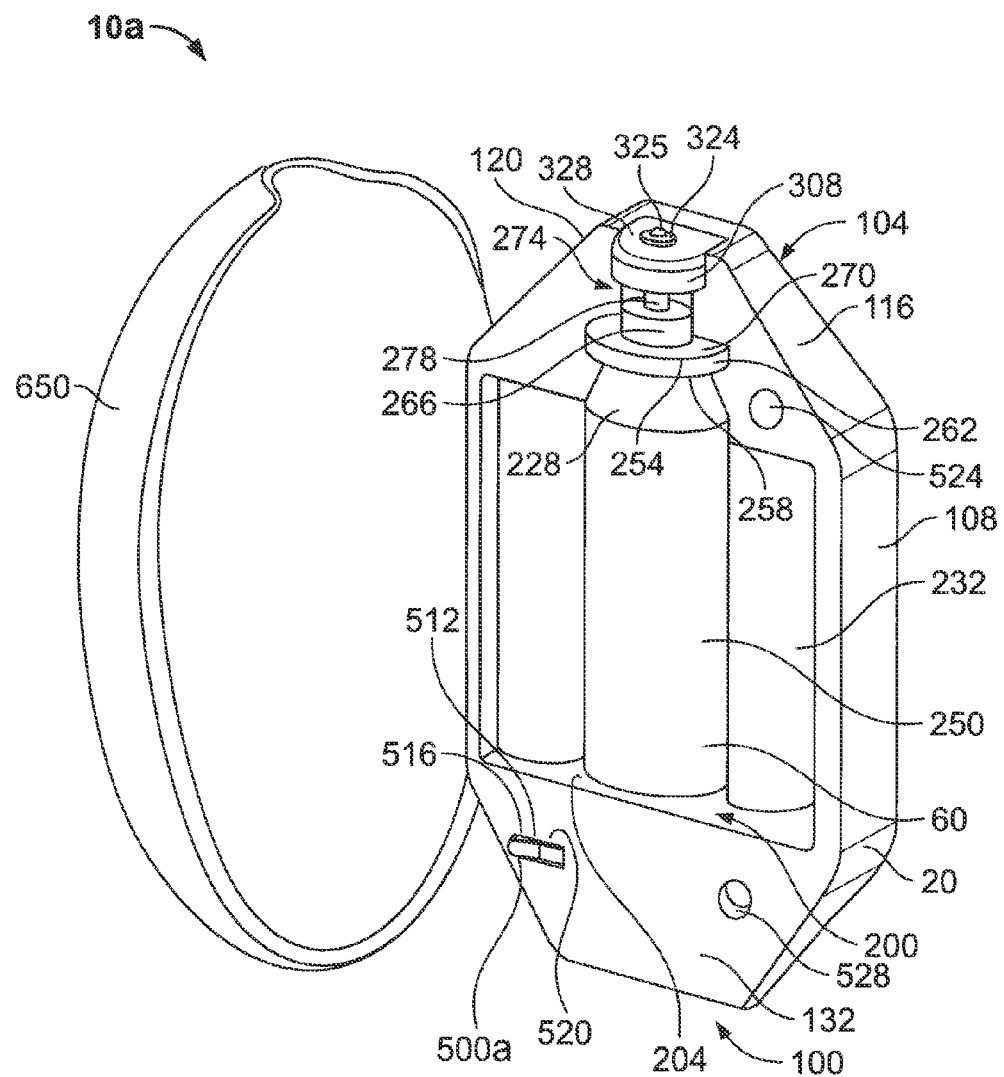
FIG. 13 is an isometric view of another dispenser having an open front cover.
Figure 14:
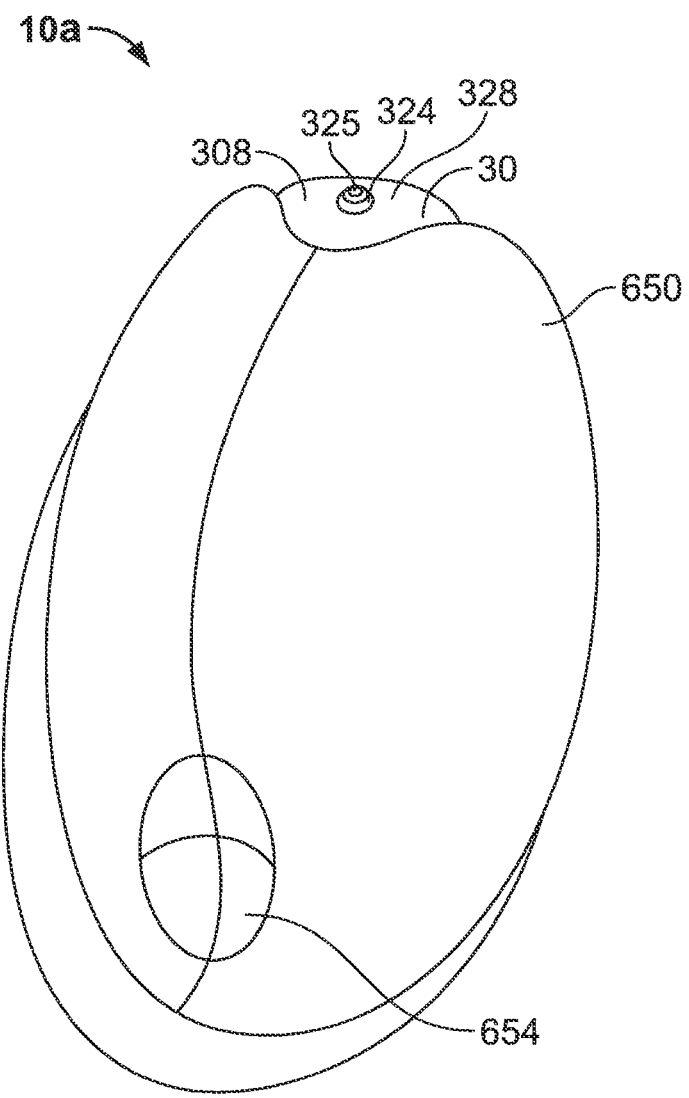
FIG. 14 is an isometric view of the dispenser of FIG. 13 with the front cover closed.

FIGS. 13-16 depict several other embodiments of the present dispensers 10, 10a, and 10b, which are characterized by the inclusion of a front cover 650 disposed adjacent the front side 132 of the housing 20. FIG. 13 shows one specific embodiment of a front cover 650 in an open position. FIG. 14 depicts the embodiment of FIG. 13 in a closed position. Closing the front cover 650 prevents the user from viewing the batteries 232 and the container 60. The front cover 650 is mounted to the first or second sidewall by a hinge (not shown). The front cover 650 is also contoured adjacent the overhang member 308 to ensure that the front cover 650 does not block or obstruct the flow path of the fluid dispensed from the second orifice 324 of the actuator arm 30.

The front cover 650 of FIGS. 13 and 14 is fashioned to allow the second switch 528 to be depressed when the front cover 650 is closed. The user applies pressure to the front cover 650 adjacent an area 654 to actuate the second switch 528. When the user presses the area 654, the front cover 650 is forcibly rotated about the hinge from the closed position a sufficient distance to cause an inside of the front cover 650 to contact and depress the second switch 528. Release of the front cover 650 after actuation of the second switch 528 causes the front cover 650 to flex back into the closed position. In other embodiments, the front cover could be depressible in one or more areas to actuate one or more switches. Still further, some embodiments have buttons or other switches disposed within the front cover 650.

Figure 15:
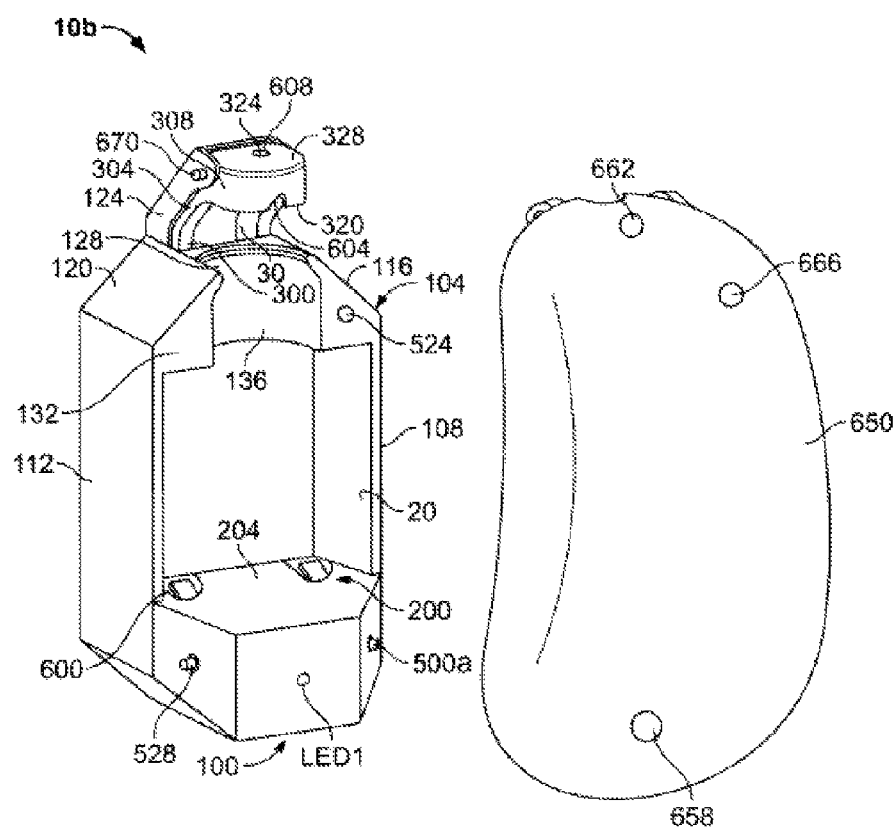
FIGS. 15 and 16 are exploded isometric views of further dispensers with alternate front covers.

In another embodiment shown in FIG. 15, the front cover 650 includes an LED port 658 to view LED1 therethrough. The present embodiment also includes a spray slot 662 to allow fluid dispensed from the dispensing bore 324 to pass therethrough. A sensor port 666 is also provided to allow a sensory access path for the sensor 524. The front cover 650 is opened by pivoting same upwardly around a hinge 670. Further, the front cover 650 of FIG. 15 is also depressible adjacent the base portion 100 of the housing 20, wherein depression of the front cover 650 results in actuation of the second switch 528.

Figure 16:
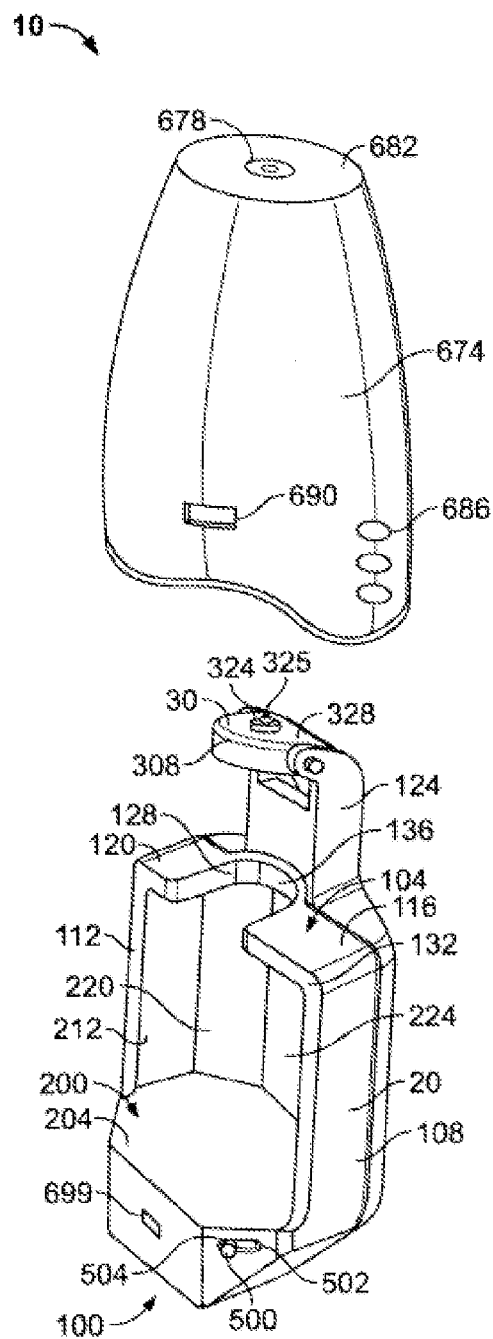

FIG. 16 depicts another dispenser 10 having a wraparound cover 674. The wraparound cover 674 fittingly engages with the housing 20 to cover the front side 132, the outer rear panel 148, and the sidewalls 108, 112. The wraparound cover 674 includes a hole 678 within a top end 682 thereof that is in alignment with the dispensing bore 324. The hole 678 allows fluid sprayed from the dispensing bore 324 to pass therethrough and reach the atmosphere. Preferably, the wraparound cover 674 includes a release mechanism 686 that disengages the wraparound cover 674 from the housing 20. In the present embodiment, the user depresses areas of the wraparound cover 674 adjacent the sidewalls 108, 112 to disengage an inside undercut 690 of the wraparound cover 674 from an undercut 694 on the front side 132 of the base portion 100. Disengaging the undercuts 690, 694 from each other allows the wraparound cover 674 to be removed from the housing 20.

An alternative embodiment of a dispenser 10c is depicted in FIGS. 17-22, which is similar to the embodiment depicted in FIG. 12 in that it generally comprises an octagonal housing 20 with the actuator arm 30 being similarly disposed for depression of the valve stem 278 of the container 60. However, the present embodiment may be altered to fully or partially encompass any of the differing structural and functional aspects described herein.

Figure 17:
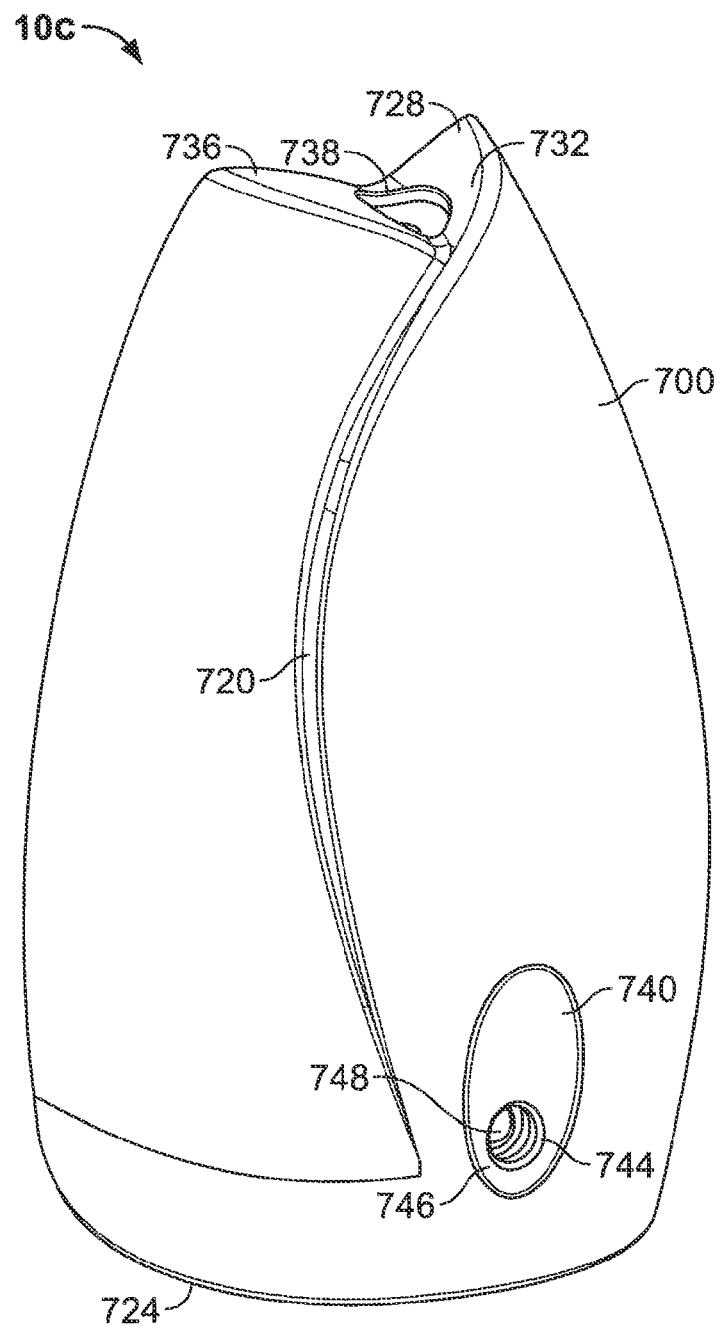
FIG. 17 is an isometric view of a different dispenser.
Figure 18:
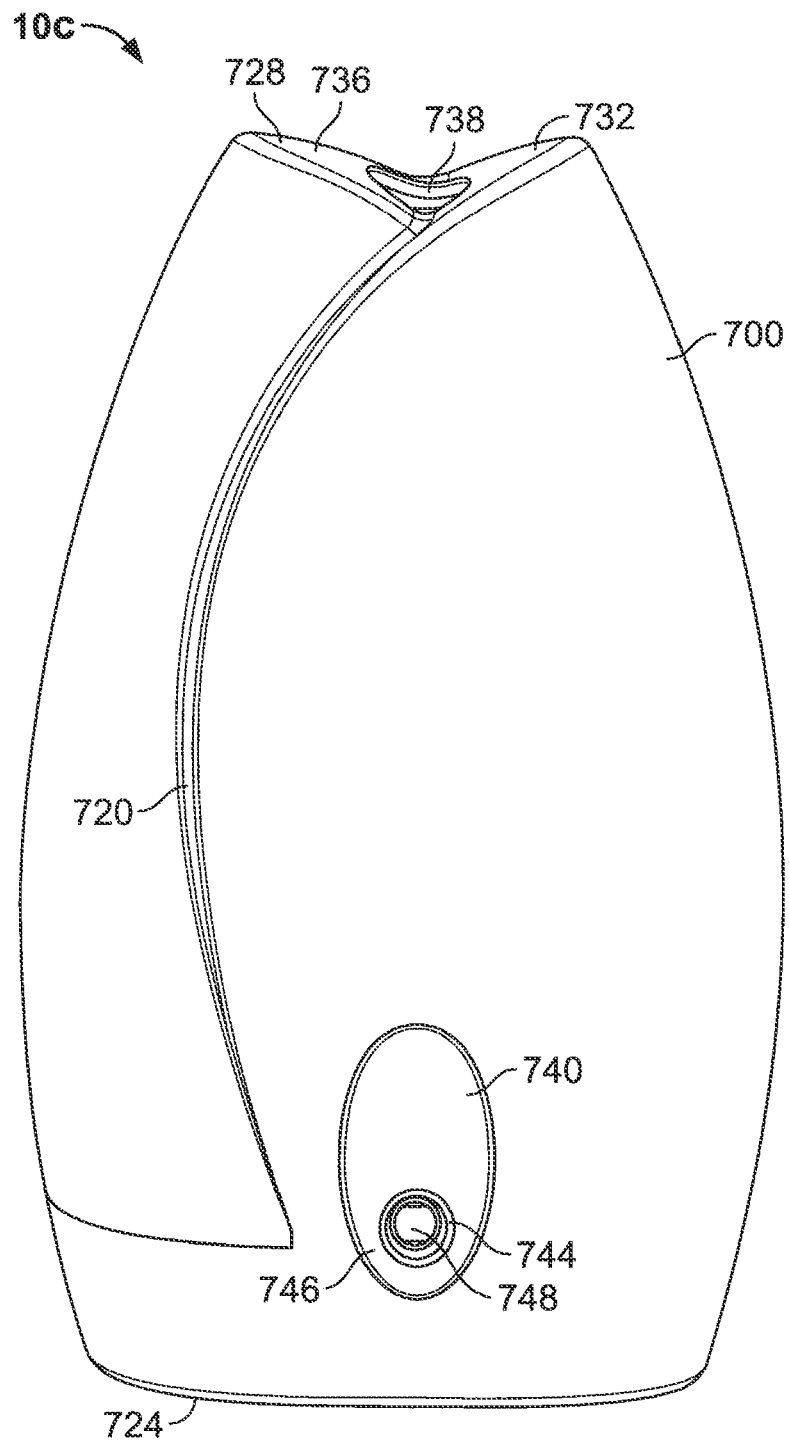
FIG. 18 is a front elevational view of the dispenser of FIG. 17.
Figure 19:
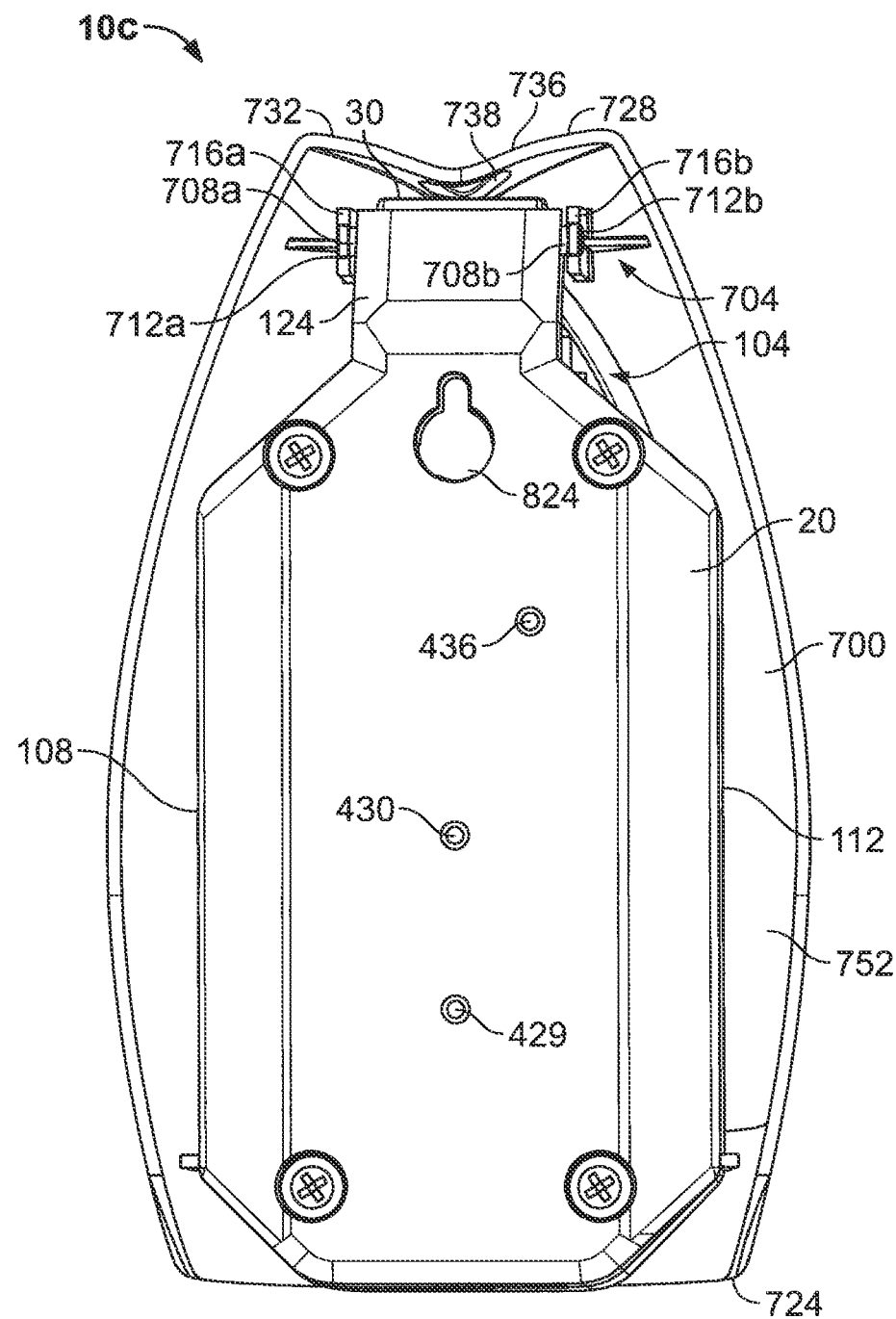
FIG. 19 is a rear elevational view of the dispenser of FIG. 17.

FIGS. 17-19 depict a tulip-shaped dispenser cover 700 secured to the housing 20. The cover 700 wraps around the side walls 108, 112, the top portion 104, the actuator arm 30, and the front side 132 of the housing 20 in a closed condition, thereby leaving a bottom end of the base portion 100 and the rear side of the housing 20 exposed. The cover 700 is pivotally attached to the actuator arm cover 124. The cover 700 is moved into an open position by rotating same about a hinge 704 comprising two cylindrical members 708a, 708b extending outwardly from the actuator arm cover 124. The cover 700 includes corresponding grooves 712a, 712b disposed on inwardly extending bars 716a, 716b that pivotally mate with the two cylindrical members 708a, 708b, respectively.

A curvilinear groove 720 extends from a lower end 724 of the cover 700 to an upper end 728 thereof and partially defines a first portion 732 of the upper end 728. A second portion 736 is disposed adjacent the first portion 732 and, in conjunction with the first portion 732, causes the upper end 728 to have a general V-shape. A circular hole 738 extends through a center of the V-shaped upper end 728. The circular hole 738 is aligned with the dispensing bore 324 of the actuator arm 30 in the closed position. The circular hole 738 is sized to allow uninterrupted or partially interrupted passage of fluid from the dispensing bore 324 therethrough. Further, an oval shaped recess 740 is disposed in the lower end 724 of the cover 700. A second circular hole 744 extends through the cover 700 at a bottom portion 746 of the oval recess 740. The second circular hole 744 is aligned with a sensor 748 within the bottom portion 100 of the housing 20 when the cover 700 is in a closed position. Still further, an inside surface 752 of the cover 700 includes an activation bar (not shown) for engagement with a push button switch 756 disposed on the bottom portion 100 of the housing 20. Pressing the cover 700 adjacent the push button switch 756 causes same to be depressed and for the electrical components of the dispenser 10c to be manually activated.

Figure 20:
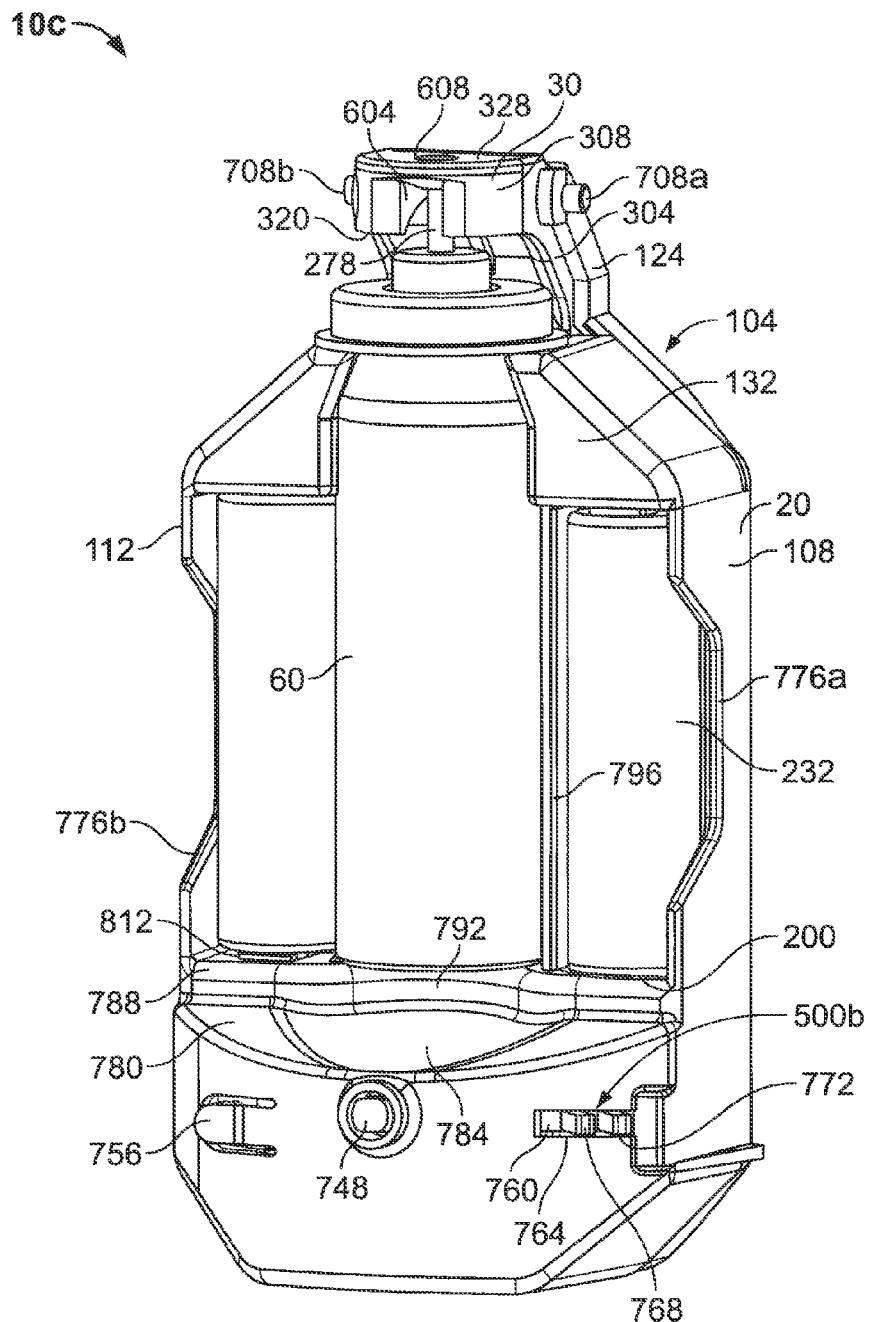
FIG. 20 is view similar to that of FIG. 17, except that a dispensing cover has been removed to show a front side of the dispenser.
Figure 21:
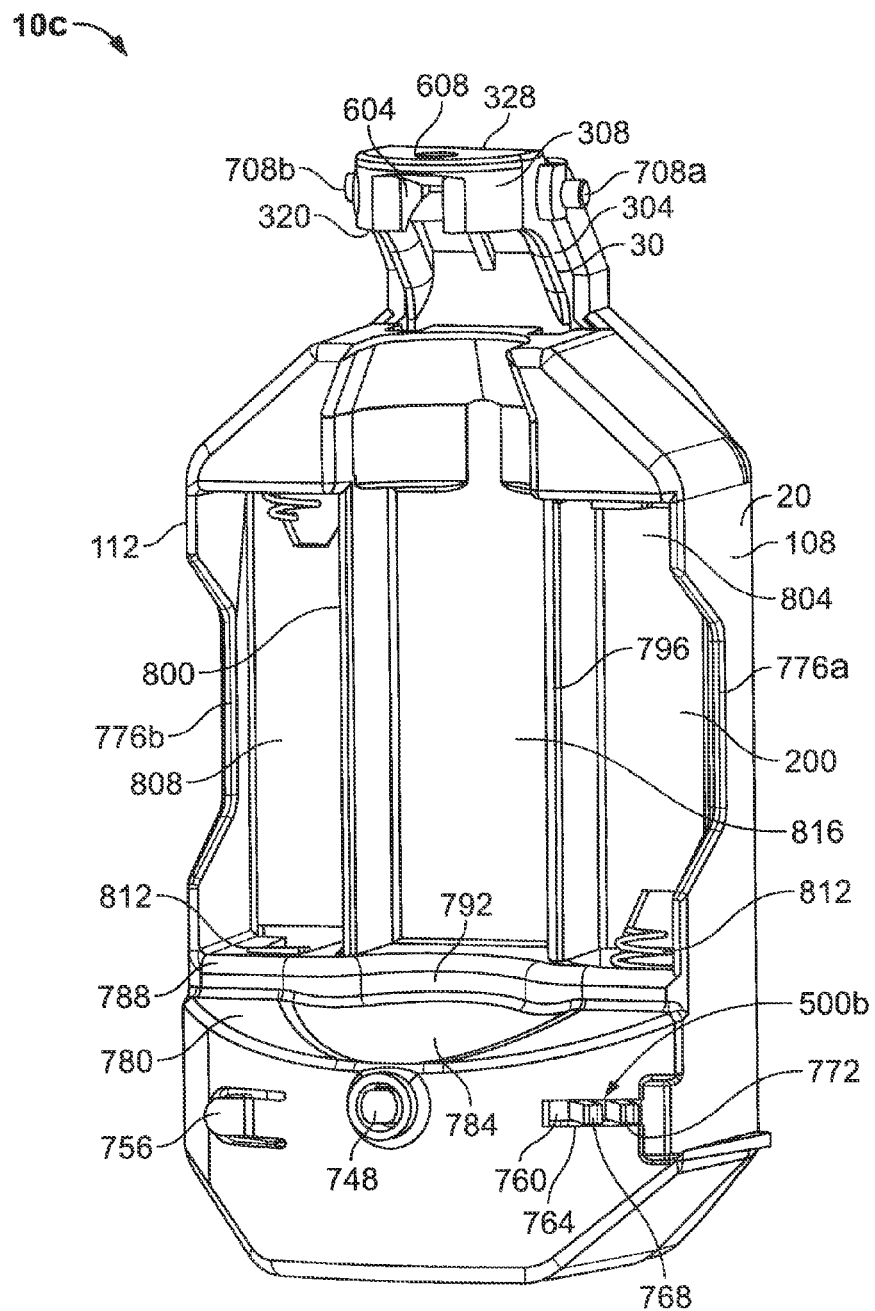
FIG. 21 is a view similar to that of FIG. 20, except that a fluid container and batteries have been removed from the front side of the dispenser.

FIGS. 20 and 21 depict the dispenser 10c without the cover 700. The housing 20 of the dispenser 10c is similar to that of dispenser 10b except that the dispenser 10c includes numerous curved surfaces and shaped edges in contrast to the sharp lines of dispenser 10b depicted in FIG. 12. One skilled in the art will find the aesthetic differences between dispensers 10c and 10b to be apparent from the provided FIGS. 12 and 17-21. However, several differences between the dispensers 10b and 10c are provided below to provide a more complete description of the dispenser 10c.

The base portion 100 of the dispenser 10c adjacent the front side 132 comprises a curved surface having a switch 500b disposed therein. The switch 500b is disposed adjacent the first side wall 108, whereas the push button switch 756 is disposed adjacent the second side wall 112 and the sensor 748 is disposed in a center of the base portion 100. The switch 500b is adapted to be toggled between four positions. A first position 760 deactivates the dispenser 10c. Movement of the switch 500b to any one of a second position 764, third position 768, or fourth position 772 energizes the electrical components of the dispenser 10c and causes the dispenser 10c to operate in a combined timed and sensing mode of operation responsive to the output of the sensor 748. While the sensor 748 is preferably a photocell light sensor capable of detecting changes in light, the sensor 748 may comprise any type of sensor known to those skilled in the art and/or as discussed herein.

Activation of the dispenser 10c may be initiated by manual input, sensory input, and/or the lapsing of a time interval as discussed in the embodiments above. It is preferred, however, that the second position 764 provide for about a twenty minute timed interval between automatic spray periods, the third position 768 provide for about a forty minute timed interval between automatic spray periods, and the fourth position 772 provide for about an eighty minute timed interval between automatic spray periods. In another preferred embodiment, the second position 764 provides an about ten minute timed interval, the third position 768 provides an about twenty minute timed interval, and the fourth position 772 provides an about forty minute timed interval. However, as noted above with respect to the prior embodiments, the time intervals may comprise any period of time desired including, for example, a time interval between about ten minutes to about eighty minutes or more, or about 10 minutes or less. It is also envisioned that different time intervals will be provided on the basis of the fluid to be dispensed and/or varying user preferences and/or inputs.

Figure 22:
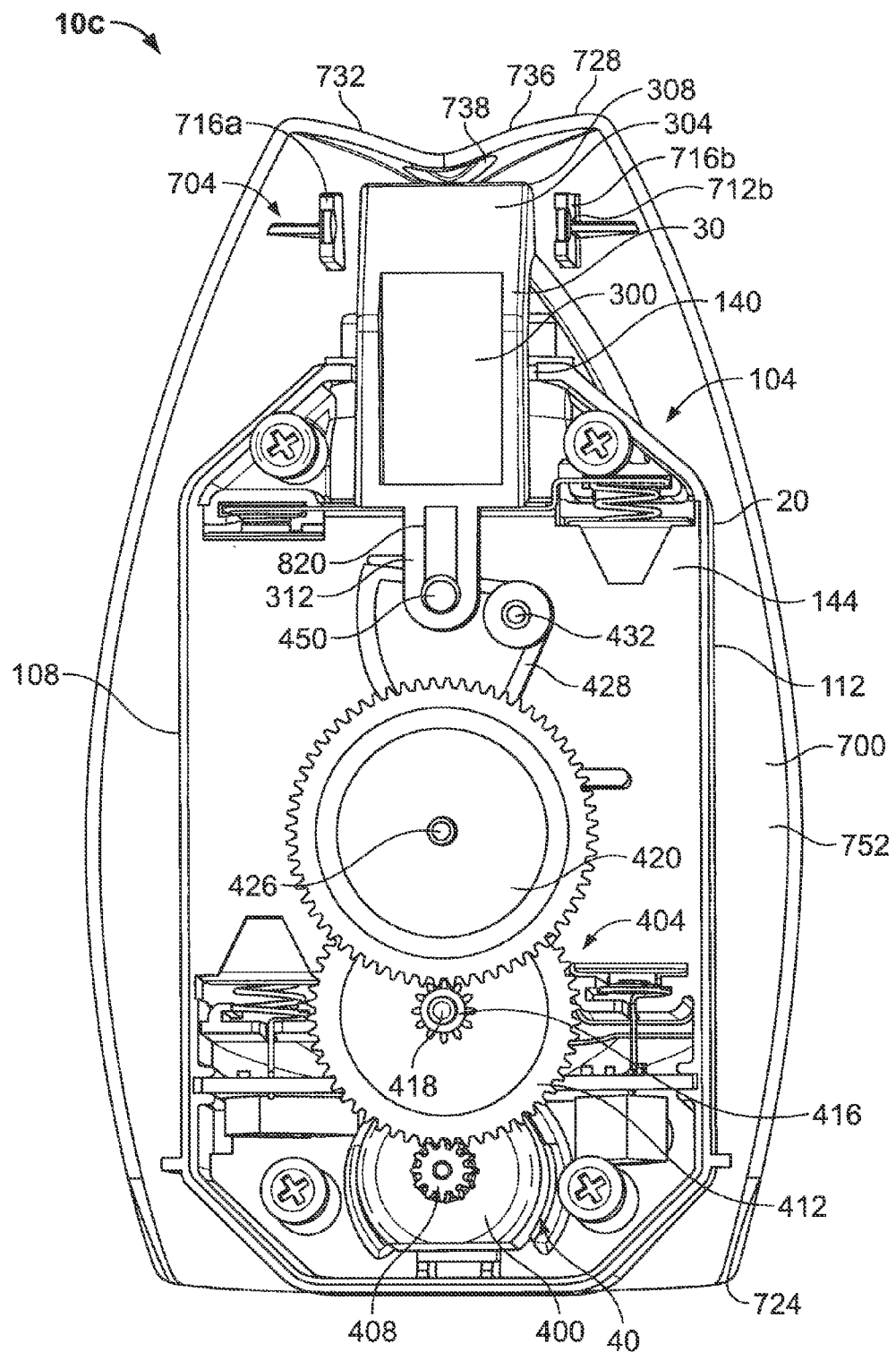
FIG. 22 is a view similar to that of FIG. 19, except that a rear panel has been removed to show a drive unit and an actuator arm.
Figure 23:
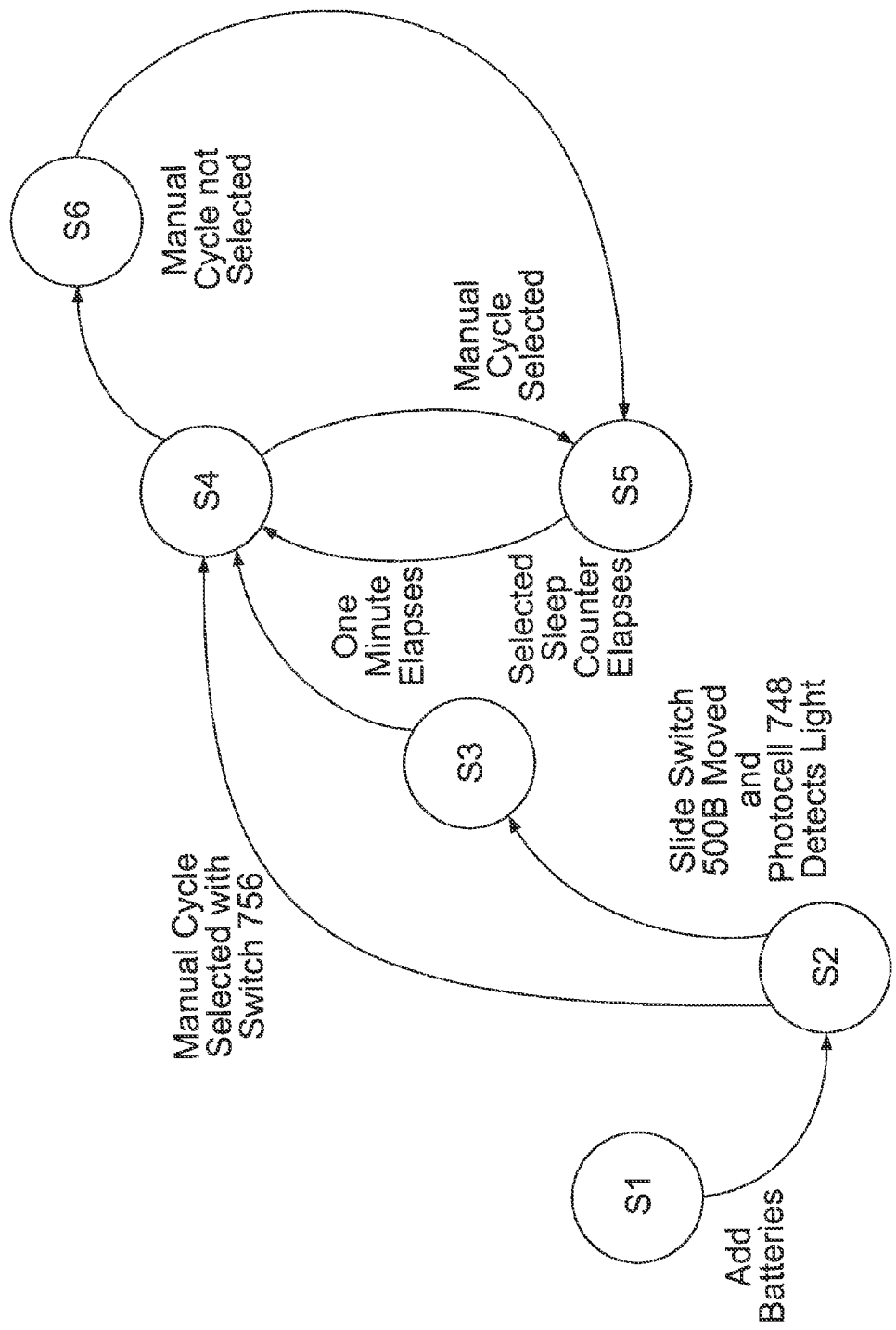
FIG. 23 is a state diagram depicting the operation of the dispenser of FIGS. 17-22 according to a third operational sequence.

Operation of the embodiment of FIGS. 17-22 is illustrated by the state diagram of FIG. 23. A state S1 comprises a condition wherein the dispenser 10c is off and the batteries 232 have not been inserted therein. Once the batteries 232 have been properly inserted into the dispenser 20c, the dispenser 10c assumes a state S2 wherein the unit awaits actuation of either of the switches 500b or 756. If a user moves the slide switch 500b to one of the twenty, forty, or eighty minute positions and the photocell sensor 748 detects light, the dispenser 10c transitions to a state S3 at which a predetermined delay period is timed. In the preferred embodiment, the delay period comprises about one minute. Also while in the state S3, the dispenser 10c initializes three sleep counters that count twenty, forty, and eighty minute sleep periods.

Upon expiration of the predetermined time period (e.g., one minute), the dispenser 10c transitions to a state S4 whereupon the drive motor 400 is energized for about one-half second. As previously noted, this motor 400 energization operates through the gear train 404 to depress the valve stem 278 and causes emission of ingredients stirred within the container 60. The dispenser 10c can also transition from the state S2 directly to the state S4 if the user depresses the manual push button switch 756.

Upon expiration of the one-half second spray period (which, in other embodiments, may have a duration other than one-half second) the dispenser 10c transitions to a state S5 if the manual cycle was previously selected. While in the state S5, the dispenser 10c either starts the sleep counters (if the sleep counters have not already been started) or continues the sleep counters if the sleep counters were previously actuated. The dispenser 10c remains in the state S5 until the sleep counter selected by the user via the slide switch 500b has elapsed, whereupon the dispenser 10c transitions or returns to the state S4 to cause spraying of the contents of the container 60. It should be noted that the transition from the state S5 to the state S4 under these circumstances results also in a resetting of the sleep counters just prior to transitioning of the dispenser 10c to the state S4.

The dispenser 10c transitions from the state S4 to a state S6 upon the end of a spraying period provided that the transitioning into the state S4 did not occur as a result of selection of a manual cycle. While in the state S6, the sleep counters are reset and the dispenser 10c automatically transitions to the state S5.

It should be noted that the dispenser 10c can transition from any of the states S3-S6 to the state S2 if the slide switches 500b move to the off position. Further, the dispenser 10c transitions from any of the states S2-S6 to the state S1 if either or both of the batteries 232 are removed.

The operation depicted in FIG. 23 may be carried out in a similar matter as described above and as known to one skilled in the art. Conventional discrete electronic components, a microprocessor, a microcontroller, and an application specific integrated circuit are contemplated as being useful in carrying out the present operation.

For purposes of further explaining how the dispenser 10c operates, the following example is illustrative of a typical embodiment. The dispenser 10c is placed in a room that is provided with no illumination. The switch 500b is initially in the first position 760 so that the dispenser 10c is inactive. The switch is thereafter toggled to the second position 764 that is utilized to initiate an automatic spray time interval of about twenty minutes. Simultaneously, the toggling of the switch 500b to the second position 764 activates the sensor 748. The sensor 748 comprises a light sensor similar to those described above. The sensor 748 fails to register a sufficient amount of ambient light and prevents controller 532 from activating the dispenser 10c. A person thereafter enters the room and turns on a light. A sufficient amount of ambient light is generated from the light to register with the sensor 748. Upon completion of a startup delay period, the drive unit 40 is directed to discharge fluid from the dispenser 10c during a first spraying period. The startup delay period is preferably about one minute long. Upon completion of the first spraying period, the dispenser 10c enters a first sleep period that lasts the predetermined time interval of about twenty minutes. Upon expiration of the first sleep period the drive unit 40 is actuated to discharge fluid during a second spraying period. Automatic operation thereafter continues with alternating sleep and spraying periods. At any time during a sleep period, the user can manually activate the dispenser 10c for a selectable or fixed period of time by depressing the push button switch 756. Manual activation of the dispenser 10c does not effect the current sleep period or when the next spraying period commences. The user enters the room again after several sleep and spraying periods have elapsed and turns off the light. The sensor 748 no longer registers a sufficient amount of ambient light and deactivates the dispenser 10c.

Further, while the combined timed and sensing mode of operation may operate in a similar manner as described above, in a different embodiment the operation is responsive to a different set of consumer desires. Specifically, activation of the dispenser 10c in response to sensory input may cause a person or animal to become frightened or surprised upon hearing the noise of the dispenser 10c while spraying or by the unexpected nature of the spraying. This may occur if the dispenser 10c automatically sprays when a person or animal moves past the dispenser 10c or at a time thereafter while they are still in the vicinity of the dispenser 10c. Further, some people and animals may not like to be exposed to a strong initial burst of fluid that may accompany a spraying from the dispenser 10c. Therefore, the combined timed and sensing mode of operation preferably prevents the automatic spraying of the dispenser 10c when a person or animal moves past or is in the vicinity of the dispenser 10c.

In a first example, the switch 500b is toggled to the second position 764, thereby providing an about twenty minute timed interval between automatic spray periods. However, other time intervals such as about fifteen minutes or more may be used. After a first sleep period of about twenty minutes the dispenser 10*c* automatically discharges fluid during a first spraying period. Upon completion of the first spraying period the dispenser 10*c* enters a second sleep period for the same twenty minute duration. This alternating pattern of spraying periods and sleep periods continues until the dispenser 10*c* is turned off or the sensor 748 is activated. During the second sleep period a person enters the room the dispenser 10*c* is disposed within and crosses a sensory path of the senor 748. However, the person leaves prior to expiration of the second sleep period. Regardless of whether the sensor 748 is active or asleep, the controller 532 does not alter the timing of the activation of the second spray period if it receives a signal from the sensor 748 during the sleep period. A second person also enters the room prior to the expiration of the second sleep period and remains in the room until the end thereof. The sensor 748 registers movement across a sensory path at the end of the second sleep period and transmits a signal to the controller 532 to prevent activation of the second spraying period. The controller 532 thereafter enters into another sleep period for a delay time interval such as about two minutes. However, other delay time intervals such as about five minutes or less may be used. After the two minute delay time interval ends the sensor 748 repeats the step of determining whether any motion registers across the sensory path. If motion is registered by the sensor 748, a second delay time interval of the same duration is initiated. This step is repeated until no motion is registered at the end of any delay time interval. However, in the present example the sensor 748 does not register any motion and sends a signal to the controller 532 to activate the dispenser 10*c* and spray. A third sleep mode is entered into for a duration of about twenty minutes. Thereafter, the prior steps are carried out in a similar manner.

In a second example, the same scenario as discussed above produces identical results up until the sensor 748 registers movement from the second person after the second sleep period has ended. In this example, the sensor 748 sends a signal to the controller 532 to prevent activation of the second spray period and thereafter continually attempts to register movement across the sensory path to determine if there is movement in the room. In the present example, the second person moves within the sensory path for approximately thirty seconds and thereafter stands still for another thirty seconds before initiating movement across the sensory path again to leave the room. During the thirty second time period the person is moving the sensor 748 registers movement and prevents activation of the second spray period. Thereafter, the sensor 748 does not register movement and sends a signal to the controller 532 to reset the timer for a delay time interval of about two minutes. However, the sensor 748 still attempts to continually register movement across the sensory path during the delay time interval. In the present example, the sensor 748 registers movement after the thirty second interval of no movement. In response, the sensor 748 continually attempts to register movement until none is detected, wherein the sensor 748 then sends a signal to restart the delay time interval. After the two minute delay time interval the dispenser 10*c* is activated. A third sleep period is thereafter entered into for a duration of about twenty minutes. The prior steps are carried out in a similar manner until the dispenser 10*c* is deactivated.

In any of the examples provided above, an initial startup delay period may be provided prior to a first spraying period after the dispenser 10*c* is activated. Further, manual activation of the dispenser 10*c* by way of the push button switch 756 may be carried out in a similar manner as described in the other embodiments herein. Still further, any variation in timing or operation of any aspect of the dispensers 10, 10*a*, 10*b* is applicable to the present embodiments.

FIGS. 20 and 21 also show that the side walls 108, 112 extend between the bottom portion 100 and the top portion 104. The side walls 108, 112 include cut out portions 776*a*, 776*b* to assist in insertion and removal of the batteries 232 from the dispenser 10*c*. The batteries 232 are inserted through the front side 132 of the housing 20 and into the recess 200. The recess 200 comprises a relatively flat bottom side 780 having a curved recess 784 disposed within a center thereof. A stepped portion 788 extends upwardly from the bottom side 780 between the side walls 108, 112. A grooved portion 792 having a width coextensive with a width of the curved recess 784 is provided within the stepped portion 788. A first inner wall 796 and a second inner wall 800 are disposed between and parallel to the side walls 108, 112. The first inner wall 796 and the side wall 108 define a first compartment 804 and the second inner wall 800 and the side wall 112 define a second compartment 808. The first and second compartments 804, 808 are sized to retain the batteries 232 therein and are provided with battery terminals 812 in electrical communication with the circuitry of the dispenser 10*c*. A retention tab (not shown) depends from the top portion 104 within both of the first and second compartments 804, 808 to assist in preventing the batteries 232 from dislodging or accidentally being removed from the dispenser 10*c*.

A third compartment 816 is provided between the first and second compartments 804, 808 for receipt of the container 60. A bottom end of the container rests on the stepped portion 788 adjacent the grooved portion 792. A finger of a user may be inserted within the grooved portion 792 to assist in the removal or insertion of the container 60. The inner walls 796, 800 are adapted to provide a relatively close fit with the container body 250. A top portion of the container 60 extends through the slot 128 disposed between the first and second shoulders 116, 120 of the top portion 104. The slot 128 is contoured to closely fit the top portion and the angled neck 228 of the container 60. The mounting cup 254 is disposed against the top portion 104 between the shoulders 116, 120.

FIGS. 20-22 show that the positioning and shape of the actuator arm 30 and the actuator arm cover 124 with respect to each other and the other functional elements of the dispenser 10*c* are similar to those shown in FIG. 12. Several differences of particular note are the provision of substantially smoother and curved surfaces and a rectangular groove within portions of the main and intermediate portions 300, 304 of the actuator arm 30. Another difference is the contouring of the second recess 608 into an oval shaped recess having a cross-sectional area that narrows non-uniformly from the upper side 328 of the overhang portion 308 toward the dispensing bore 324 in an interior thereof. Further, the dispensing bore 324 is offset from a center of the second recess 608.

The drive motor 400 and the associated gear train 404 used to depress the valve stem 278 operate in substantially the same way as described above. One particular difference is the positioning and orientation of the third pinion 424 and the lever gear 428. Specifically, the third pinion 424 is disposed adjacent the inner rear panel 144 as opposed to the outer rear panel 148. Similarly, the lever gear 428 is on a side of the idler gear 420 that is now closer to the inner rear panel 144. Further, the axle 432 that extends from the inner rear panel 144 to the hole 436 of the outer rear panel 148 is now closer to the side wall 112 than the side wall 108. The molded rib 454 projecting from the inner rear panel 144 is also disposed closer to the side wall 112. In contrast to the previously described embodiments, the lever gear 428 is rotated counter-clockwise to pull the actuator arm 30 downwardly into the discharge position. Still further, the offset pin 450 is disposed in a truncated racetrack shaped groove 820 as opposed to a circular hole.

The dispenser 10c is preferably disposed on a support surface while in an active state. In one embodiment, the bottom end of the bottom portion 100 is adapted to be placed on a relatively flat support surface. Further, the dispenser 10c may be rotated to rest the outer rear panel 148 adjacent the support surface. In a different embodiment, an adhesive is applied to the outer rear panel 148 to adhere the dispenser 10c to a substantially vertical support surface. In yet another embodiment, a hole 824 is provided in the outer rear panel 148 for attaching the dispenser 10c to a corresponding hook or member extending from a substantially vertical support surface.

Yet another embodiment of a dispenser 10d is depicted in FIGS. 24-29, which is similar to the embodiment of the dispenser 10c depicted in FIGS. 17-22. However, the present embodiment may be altered to fully or partially encompass the differing structural and functional aspects of any of the embodiments described herein.

Figure 24:
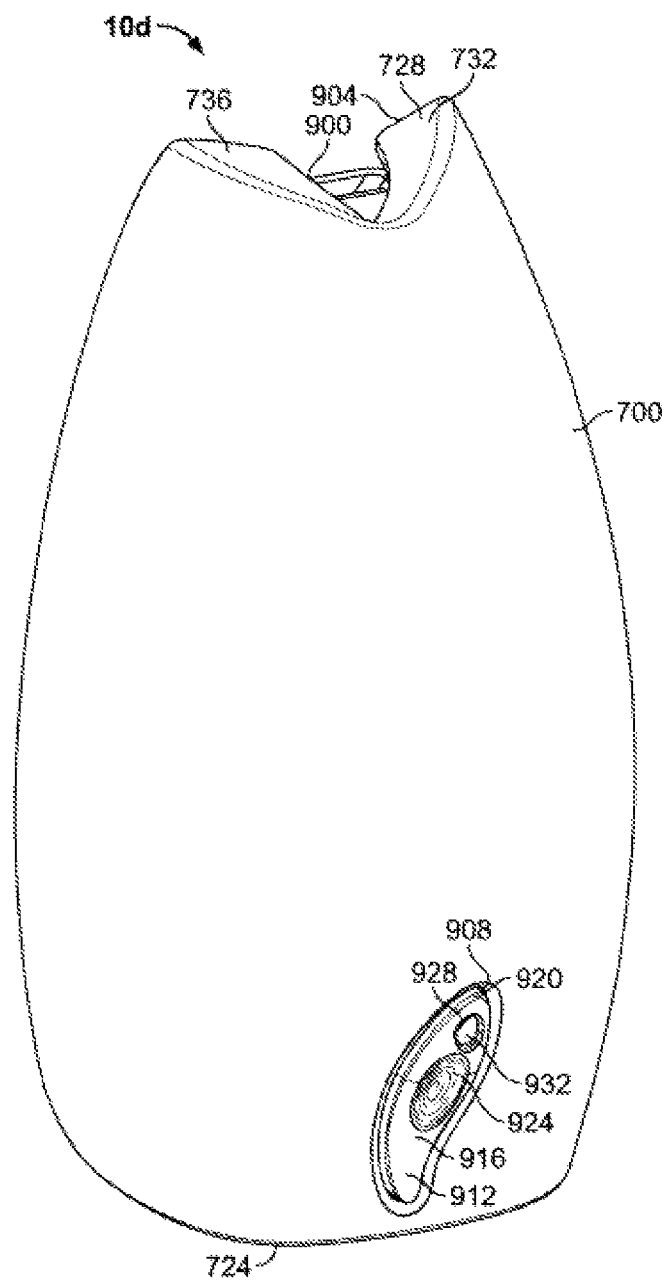
FIG. 24 is an isometric view of another dispenser.
Figure 25:
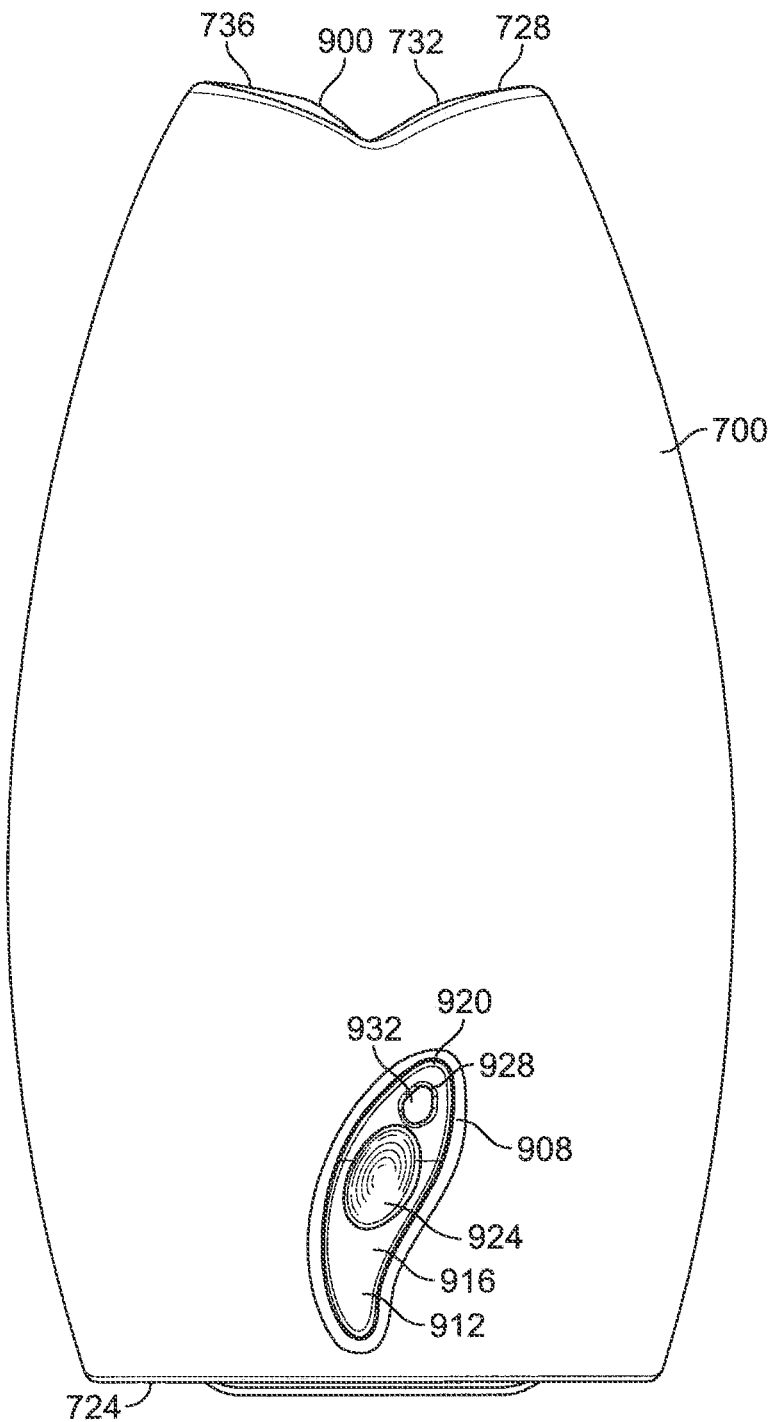
FIG. 25 is a front elevational view of the dispenser of FIG. 24.
Figure 26:
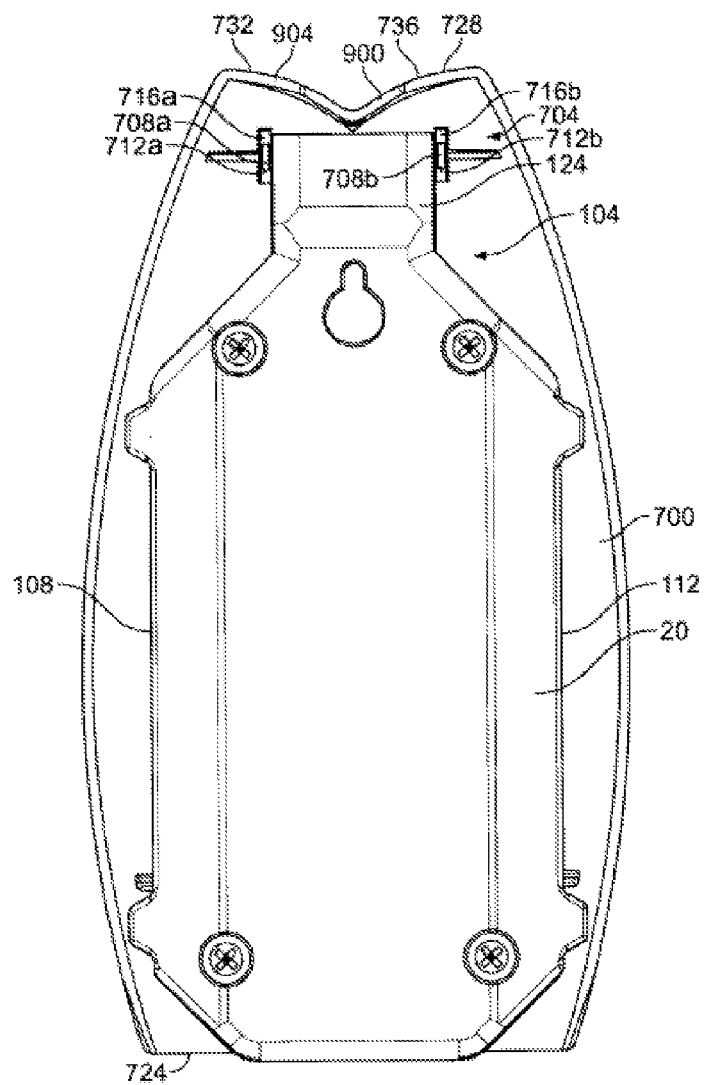
FIG. 26 is a rear elevational view of the dispenser of FIG. 24.

FIGS. 24-26 depict the tulip shaped cover 700 similarly secured to the housing 20 as described in connection with the dispenser 10c. The cover 700 wraps around the side walls 108, 112, the top portion 104, the actuator arm 30, and the front side 132 of the housing 20. The bottom end of the base portion 100 and the rear side of the housing 20 remain exposed. The cover 700 is pivotally attached to the actuator arm cover 124 by the hinge 704 to move the cover 700 between open and closed positions. The hinge 704 includes the opposing cylindrical members 708a, 708b disposed on the actuator arm 30, which are pivotally engaged with the grooves 712a, 712b within the extending bars 716a, 716b of the cover 700. However, it is contemplated that the cover 700 may be modified to be pivotally attached to one of the side walls 108, 112, the base portion 100, or any other portion of the housing 20. Indeed, any of the modifications to the covers described hereinabove with respect to other embodiments may be used with the dispenser 10d. In one embodiment, a boss (not shown) disposed on an interior of the cover 700 is attachable to the front side 132 of the base portion 100 to keep the cover 700 closed during operation of the dispenser 10d. Further, the boss or some other structure on the interior of the cover 700 may be adapted to actuate a switch (not shown), which would allow activation of the dispenser 10d when the cover 700 is closed and prevent activation of the dispenser 10d when the cover 10d is partially or fully open.

The upper end 728 of the cover 700 is defined by the first portion 732 and the second portion 736, which give the upper end 728 a general V-shape. A substantially U-shaped groove 900 is provided within the upper end 728, which is centrally disposed therein and extends from a rear portion 904 of the cover 700 toward a front portion thereof. The groove 900 is aligned with the dispensing bore 324 of the actuator arm 30 so that fluid emitted therefrom may pass through the cover 700 in an uninterrupted or partially interrupted manner.

The cover 700 also includes a generally teardrop shaped orifice 908 provided in the lower end 724 thereof. A similarly shaped button 912 extends through the orifice 908 and projects outwardly from the cover 700. The button 912 includes a top surface 916 for engagement by a user's thumb or finger. The top surface 916 is bounded by a peripheral edge 920 and has a generally concave appearance therebetween. An oval shaped recess 924 is disposed within a medial portion of the top surface 916, which is adapted to assist a user in engaging the button 912 to actuate same. A curved orifice 928 is disposed above the recess 924 on the top surface 916 of the button 912. The orifice 928 is aligned with a sensor 932 within the bottom portion 100 of the housing 20. The button 912 is provided for activating the dispenser 10d, wherein a signal is generated to activate the electrical components of the dispenser 10d to emit fluid upon the depression of the button 912. The button 912 is attached to the front side 132 of the housing 20 by way of a living hinge 934, wherein the depression and/or rotation of the button 912 about the living hinge 934 causes a switch (not shown) beneath an extension 935 to generate a signal and the dispenser 10d to discharge fluid during a manual activation sequence.

Figure 27:
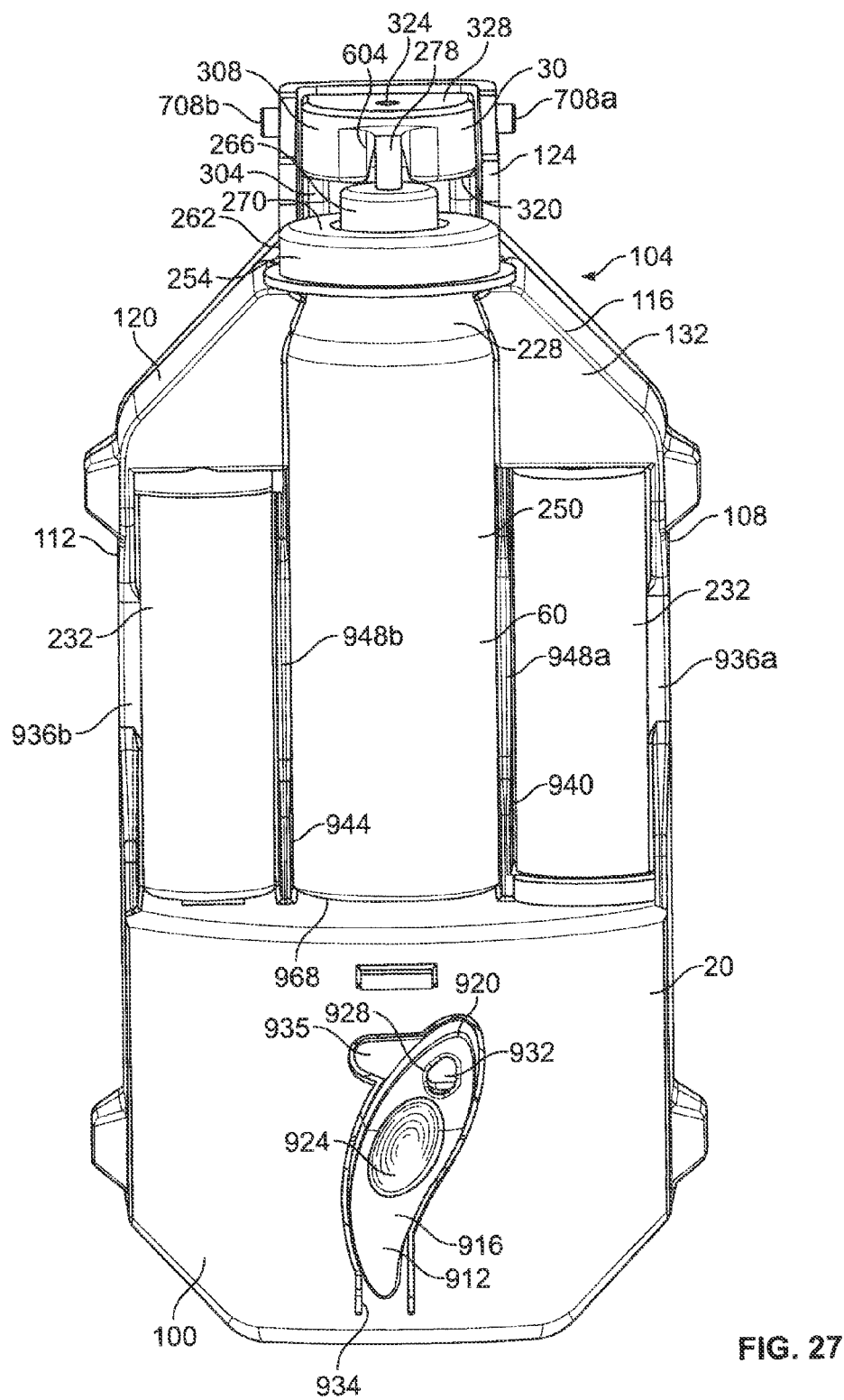
FIG. 27 is a view similar to that of FIG. 25, except that a dispensing cover has been removed to show a front side of the dispenser.
Figure 28:
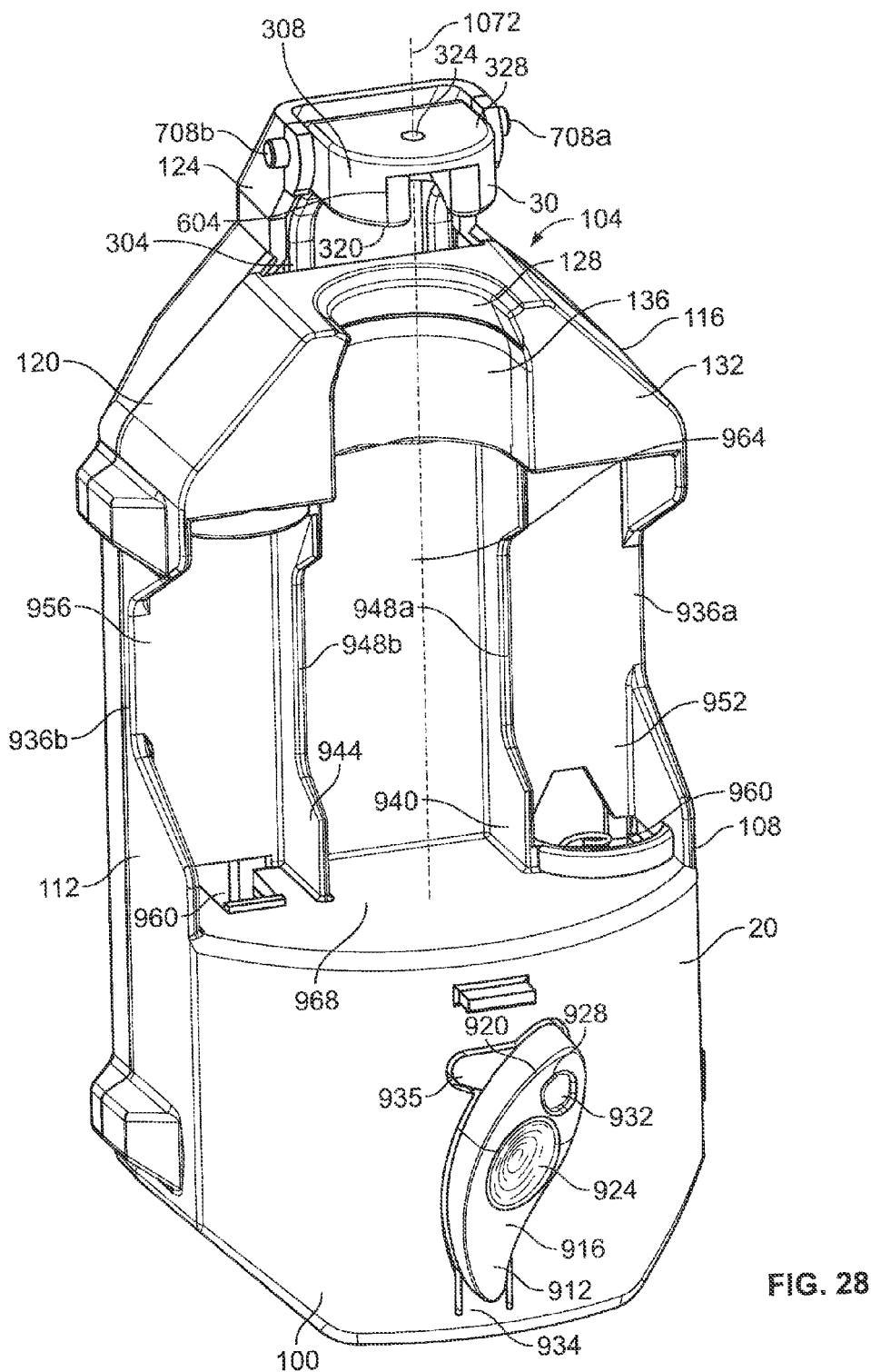
FIG. 28 is an isometric view of the dispenser of FIG. 27, except that a fluid container and batteries have been removed from the front side of the dispenser.

FIGS. 27 and 28 depict the dispenser 10d without the cover 700. The housing 20 of the dispenser 10d is similar to that of dispenser 10c except for variations in some of the curved surfaces and shaped edges depicted in FIGS. 20 and 21. One skilled in the art will find the aesthetic differences between the dispensers 10d and 10c to be apparent from the provided FIGS. 24-29. However, several differences between the dispensers 10d and 10c are provided below to provide a more complete description of the dispenser 10d.

The base portion 100 of the dispenser 10d does not include the four position switch 500b adjacent the first side wall 108 nor the push button switch 756 adjacent the second side wall 112. Rather, the button 912 is substantially centrally disposed within the front side 132 of the base portion 100. Further, the sensor 932 is operatively disposed behind the orifice 928 of the button 912. Still further, the dispenser 10d does not include a slide switch or any other switch for a user to select a timing interval for the dispensing of fluid from the container 60. In the present embodiment, the dispenser 10d is operated in light of pre-selected parameters dependent upon a combined timed and sensing mode. The dispenser 10d is activated upon operatively placing the batteries 232 into the dispenser 10d.

Activation of the dispenser 10d is initiated by manual input or sensory input. In the present embodiment, the sensor 932 is a photocell motion sensor. The photocell collects ambient light and allows a controller to detect any changes in the intensity thereof. Filtering of the photocell output is undertaken by the controller. If the controller determines that a threshold light condition has been reached, i.e., a predetermined level of change in light intensity has been received by the photocell over a short interval, the controller activates the drive unit 40. In the present embodiment, the predetermined level of change in light intensity comprises a high-to-low transition of light intensity and a low-to-high transition in light intensity. For example, if the dispenser 10d is placed in a lit bathroom, a person walking past the sensor 932 and who stands still within the sensory path may block a sufficient amount of ambient light from reaching the sensor 932 over a first time interval to cause a signal to be developed indicating a high-to-low transition in light intensity. In the present scenario, however, the controller will not activate the dispenser 10d because a low-to-high transition in light intensity has not been received by the photocell during a second time interval, i.e., the person has not walked through the sensory path. However, if the person were to continue walking through the sensory path within the second time interval, a low-to-high transition in light intensity would occur and cause the controller to activate the dispenser 10d.

The use of a combined high-to-low and a low-to-high transition in light intensity prevents the undesired discharge of fluid. For example, if a person merely shuts a light off or turns a light on but does not walk through the sensory path, the present embodiment does not trigger a spraying operation, thereby conserving container fluid. It is anticipated that the controller may be triggered irrespective of whether a high-tolow transition occurs before or after a low-to-high transition in light intensity. It is also anticipated that the first and second time intervals of the light intensity transitions may be within any time range. However, it is preferred that the first and second time intervals be of a sufficiently short duration so that light transitions over long periods of time, such as transitions that occur during the daytime and at dusk or dawn, will not cause the controller to activate the dispenser 10d.

In the present embodiment, the dispenser 10d only effects fluid discharge when the high-to-low and low-to-high transitions occur within a specified time interval. It is anticipated that any number of specified time intervals may be utilized to practice the present embodiment. However, in a preferred embodiment the specified interval is short enough to preclude discharge of fluid between events that occur at widely spaced time intervals, e.g., turning a light on in the morning and turning the same light off in the evening.

Figure 30:
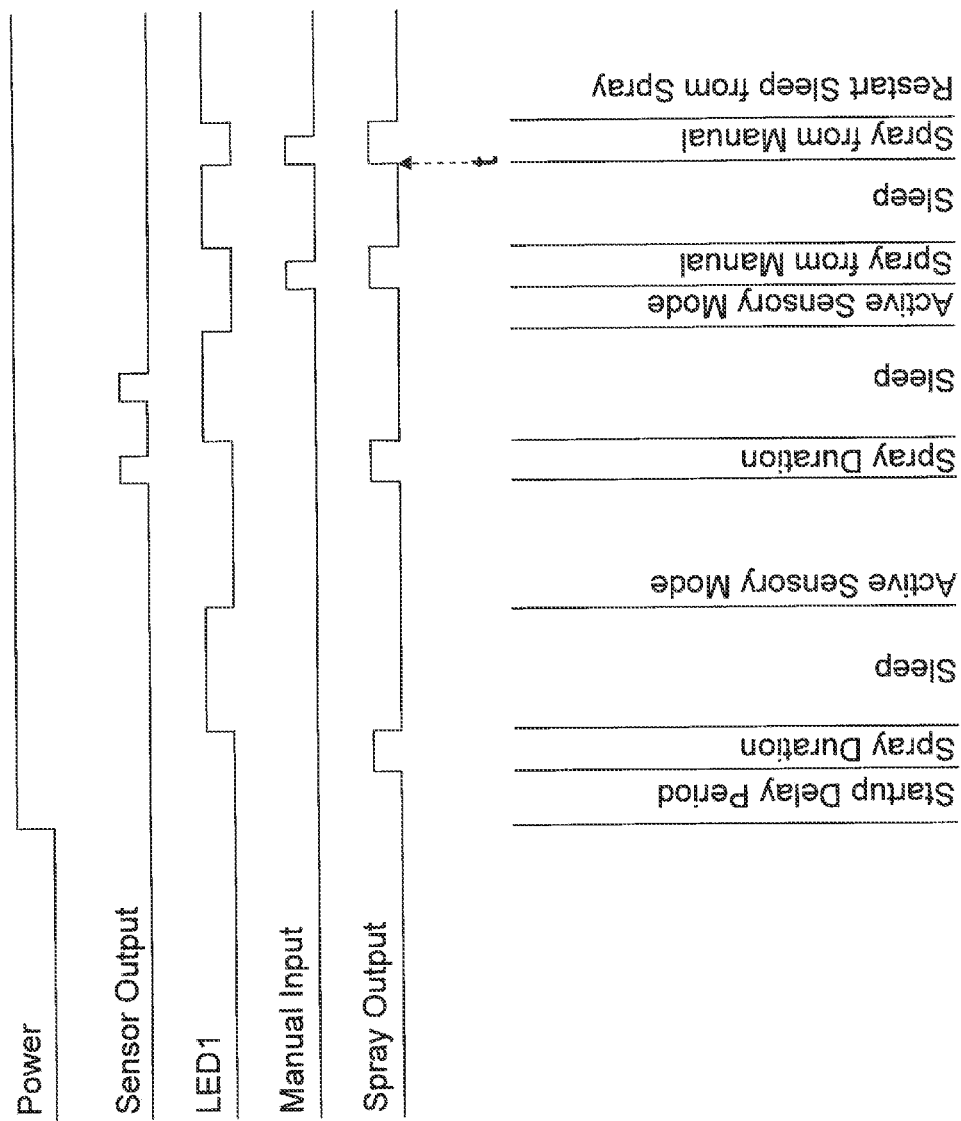
FIG. 30 is a yet another timing diagram illustrating the operation of the dispenser of FIGS. 24-29 according to a fourth operational sequence.

When the batteries 232 are inserted into the housing 20, the dispenser 10d preferably operates as shown by the timing diagram of FIG. 30. Turning now to FIG. 30, it will be seen that upon insertion of the batteries 232 the dispenser 10d enters a startup delay period. Upon expiration of the startup delay period, fluid is discharged from the dispenser 10d during a first spraying period. Upon completion of the first spraying period, the dispenser 10d enters a first sleep mode or lockout period, during which spraying is prevented even if motion is detected by the sensor 932. Thereafter, the dispenser 10d enters an active mode, wherein the sensor 932 continuously monitors for motion within its sensory path in a manner as described above. If the sensor 932 detects motion the controller immediately activates the drive unit 40 to discharge fluid from the dispenser 10d during a second spraying period. Upon completion of the second spraying period, the dispenser 10d enters a second sleep period. The dispenser 10d is prevented from automatically activating again in response to detection of motion until the second sleep period has elapsed. The sleep periods prevent over-spraying by numerous activations that occur in heavily trafficked areas. It is preferred that the sleep period last about 30 minutes.

At any time the user can initiate a manual spraying operation by manually actuating the button 912 to discharge fluid during a manual spraying period. For example, if the user were to depress the button 912 during the startup delay period, or a sleep period, or prior to motion detection during an active mode, the controller would trigger a manual spraying period and cause the discharge of fluid from the dispenser 10d. Upon completion of the manual spraying period, the dispenser 10d undergoes a complete sleep period. Thereafter, the dispenser 10d alternates between sleep periods and spray periods initiated by motion detection following expiration of a sleep period. A full sleep period follows every spray period, regardless of whether the spray period was responsive to motion detection or actuation of the button 912. For example, the timing diagram of FIG. 30 illustrates another manual actuation at a time "t" and the dispenser 10d thereafter entering a full sleep period.

In one embodiment, an LED indicator (not shown) is provided on the housing 20, which may be viewable through an orifice in the cover 700 or only viewable upon rotating the cover 700 into an open position. When the dispenser 10d is in a sleep mode, the LED indicator is illuminated to provide an indication to a user that the dispenser 10d will not automatically spray. Preferably, the LED indicator is turned on and off at a high frequency so that the LED appears continuously illuminated, which provides the user a constant indication of the dispensing status of the dispenser 10d and increases the life of the batteries 232. When the dispenser 10d is in an active sensory mode or an automatic or manual spraying mode, the LED indicator is off In a different embodiment, the LED indicator is similarly de-activated when the dispenser 10d is in the active sensory mode, but is activated prior to the emission of fluid from the dispenser 10d in response to an automatic and/or manual spraying mode. The LED indicator therefore acts as a warning light to allow a user to clear the area from around the dispenser 10d prior to the emission of fluid. In the present embodiment, the LED indicator may be continuously illuminated for a set time interval prior to activation of the dispenser 10d or the LED indicator may be pulsed one or more times, e.g., the LED indicator may be pulsed at five second intervals. It is anticipated that other uses for the LED indicator may be provided for in the present embodiments, e.g., the LED indicator could alternatively be lit only during the sleep mode, the LED indicator could be used to indicate that the batteries 232 are dead, or the LED indicator could be combined with one or more LEDs of the same or varying color to indicate various operating parameters of the dispenser 10d.

As noted above with respect to the prior embodiments, the time intervals may comprise any period of time desired. For example, the sleep period may be modified to be within a range of about 15 min. to about 3 hrs. depending on the anticipated level of room usage, the strength of the fluid to be dispensed, the size of the room, etc. Similarly, the startup delay period may be modified to be within a range of about 5 sec. to about 2 min. depending on the environment the dispenser 10d will be used in. For example, a longer startup delay period may be useful in an environment where people have a disability or slower response time so that a user is not inadvertently sprayed after inserting the batteries 232 into the dispenser 10d. However, any time period outside of the above noted ranges may be utilized to practice any of the embodiments herein.

The present embodiment may also be modified to include a user selectable sleep period. For example, a switch or dial may be provided on the housing 20 with an off position and one or more user selectable positions. In the present example, the dispenser 10d has a first position that coincides with a sleep period of about 20 min. and a second position that coincides with a sleep period of about 40 min. Therefore, when the batteries are operatively inserted into the housing 20 the dispenser 10d does not automatically turn on. Rather, a user must select one of the first or second positions to activate the dispenser 10d and begin the operating sequence as described above and depicted in FIG. 31. However, in the present example the user is able to select the length of the sleep period as opposed to having the duration of the sleep period predefined.

In any of the embodiments disclosed herein, the sleep periods and/or spray periods may all be of the same duration. If desired, one or more of the sleep periods may be longer or shorter than other sleep periods and/or one or more of the spray periods may be longer or shorter than other spray periods. Still further, the startup delay period may be omitted and the first spraying operation can be undertaken immediately upon power-up of the dispenser. In fact, any variation in timing or operation of any aspect of the dispensers 10, 10a, 10b, and 10c is applicable to the present embodiments.

While the sensor 932 is preferably a photocell light sensor capable of detecting changes in the intensity of light, the sensor 932 may comprise any type of sensor known to those skilled in the art and/or as discussed herein.

Figure 31:
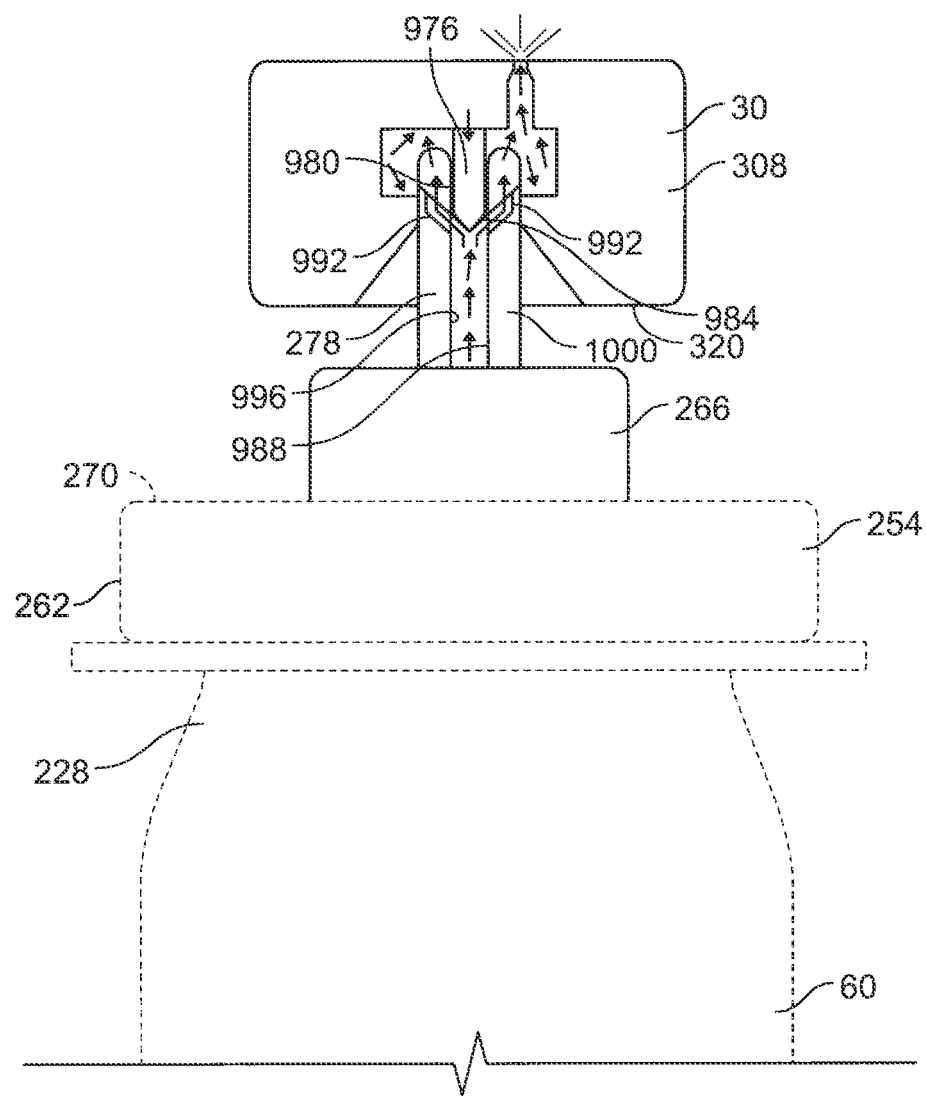
FIG. 31 is a fragmentary diagrammatic partial sectional view of a different embodiment of the actuator arm depicted in FIG. 27 having an actuating element in contact with a valve stem.

The operations described in view of FIG. 31 may be carried out in a similar manner as described above and as known to one skilled in the art. Conventional discrete electronic components, a microprocessor, a microcontroller, and an application specific integrated circuit are contemplated as being useful in carrying out the present operations.

FIGS. 27 and 28 depict the side walls 108, 112 extending between the bottom portion 100 and the top portion 104. The side walls 108, 112 include cut out portions 936*a*, 936*b* that extend between the front side 132 and the inner rear panel 144. A first inner wall 940 and a second inner wall 944 are disposed between and parallel to the side walls 108, 112. The first and second inner walls 940, 944 similarly include cut out portions 948*a*, 948*b*, respectively, that extend inwardly from the front side 132 toward the inner rear panel 144. The first inner wall 940 and the side wall 108 define a first compartment 952 and the second inner wall 944 and the side wall 112 define a second compartment 956. The first and second compartments 952, 956 are sized to retain the batteries 232 therein and are provided with battery terminals 960 in electrical communication with the circuitry of the dispenser 10*d*. The cut out portions 936*a*, 936*b*, 948*a*, 948*b* are provided to assist in the insertion and removal of the batteries 232.

FIGS. 27 and 28 also depict a third compartment 964, which is provided between the first and second compartments 952, 956 within the recess 200 for receipt of the container 60. A bottom end of the container 60 is suspended above a substantially flat bottom wall 968 of the recess 200. The spacing between the bottom end of the container 60 and the bottom wall 968 defines a void that allows a user to insert or otherwise manipulate a finger or nail adjacent the container 60 to remove same for replacement. The first and second inner walls 940, 944 are adapted to provide a relatively close fit with the container body 250. A top portion of the container 60 extends through the slot 128 disposed between the first and second shoulders 116, 120 of the top portion 104. The slot 128 is contoured to closely fit the top portion and the angled neck 228 of the container 60. If desired, the slot 128 may be dimensioned to form an interference fit with the container 60. Further, the container 60 and the inner wall 136 of the slot 128, or any other portion of the dispenser 10*d* in communication with the container 60, may be modified as described herein to provide an engagement mechanism that assists in aligning the container 60 with the actuator arm 30 or that provides means for utilizing containers of varying sizes.

Engagement mechanisms, such as those discussed above, are also helpful in ensuring that an improper container is not inserted into the dispenser 10*d*. For example, if the dispenser 10*d* is placed in a living room of a user's home he or she may inadvertently place a container of an aerosolized insecticide within the dispenser 10*d* if a proper engagement mechanism is not provided. An engagement mechanism can also assist in preventing the mixture of different aerosolized products. For example, if a first aerosol is inadvertently replaced by a different second aerosol, residual components of the first aerosol still within the dispenser 10*d* will mix with the components of the second aerosol. While various engagement mechanisms are known to those skilled in the art, the engagement mechanisms described in U.S. Pat. Nos. 6,830,164 and 6,978,914, which are herein incorporated by reference in their entirety, are of particular interest.

Figure 32:
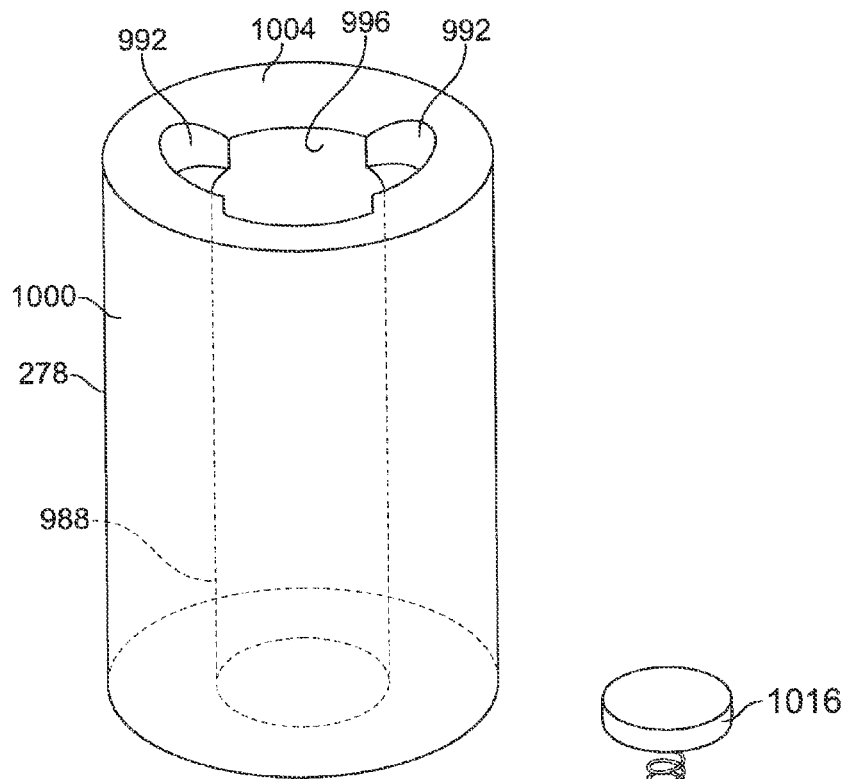
FIG. 32 is an enlarged isometric view of a valve stem.
Figure 33:
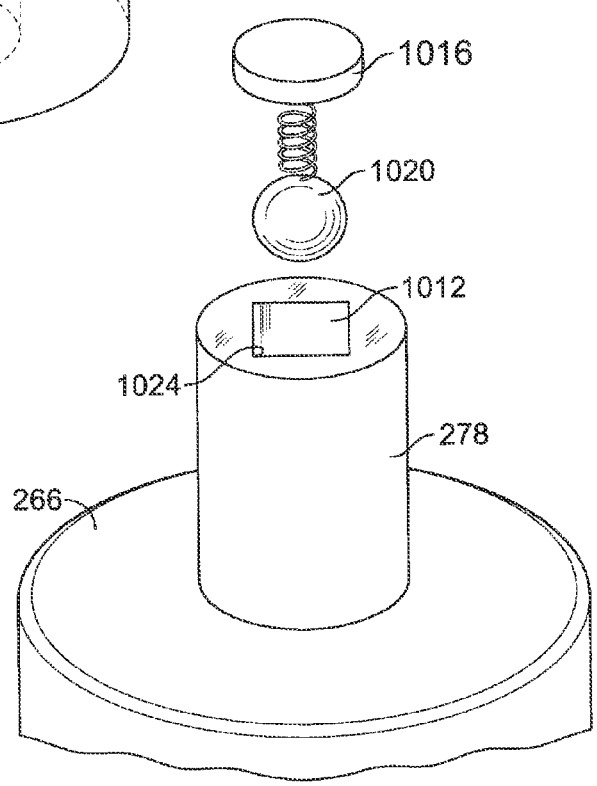
FIG. 33 is a fragmentary diagrammatic isometric view of another embodiment of a valve element disposed adjacent an actuating element.
Figure 34:
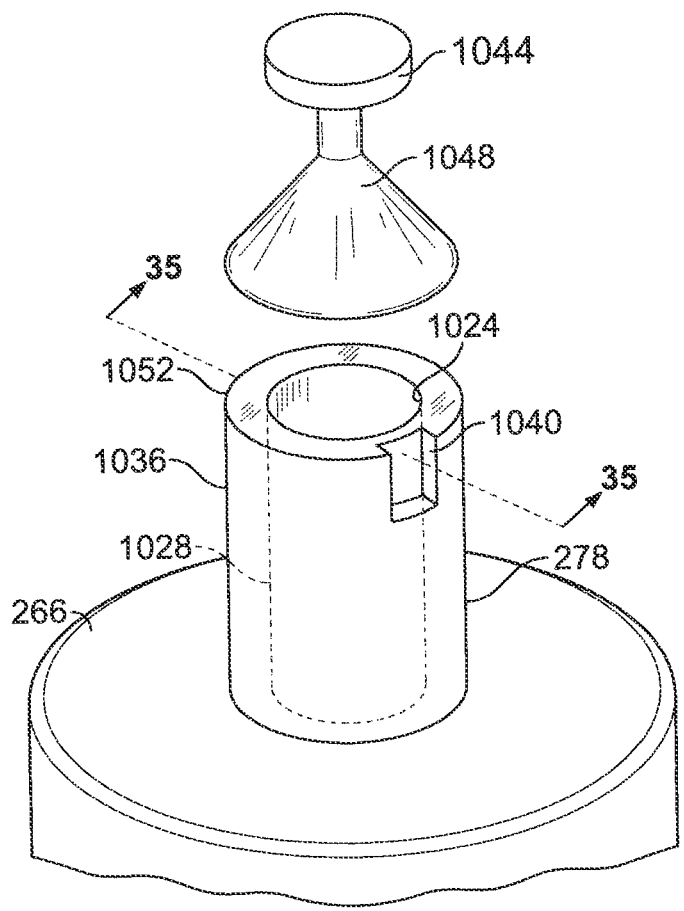
FIG. 34 is a view similar to FIG. 33 of another embodiment of an actuating element adjacent a valve element.
Figure 35:
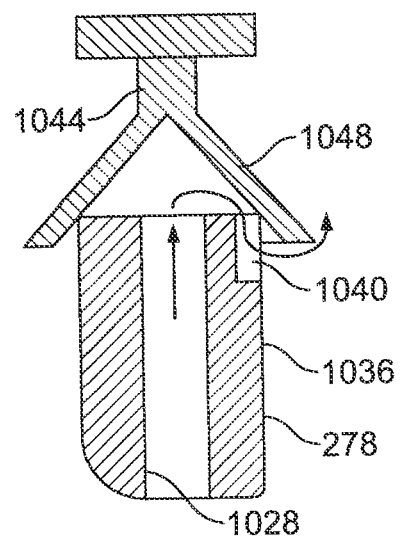
FIG. 35 is a sectional view taken generally along the lines 35-35 of FIG. 34 with the actuating element in engagement with the valve element.
Figure 36:
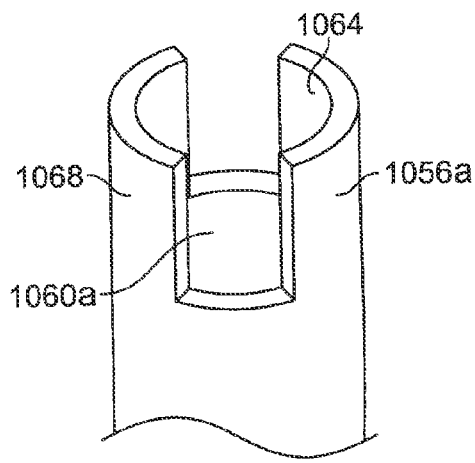
Figure 37:
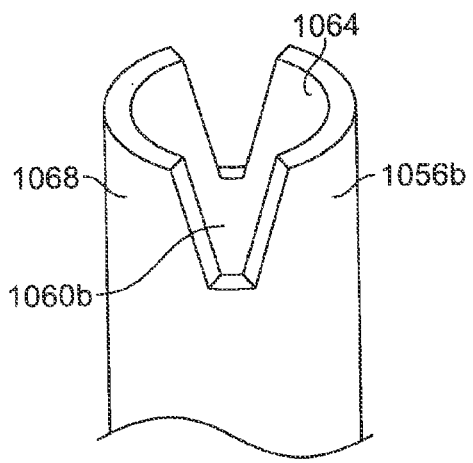
Figure 38:
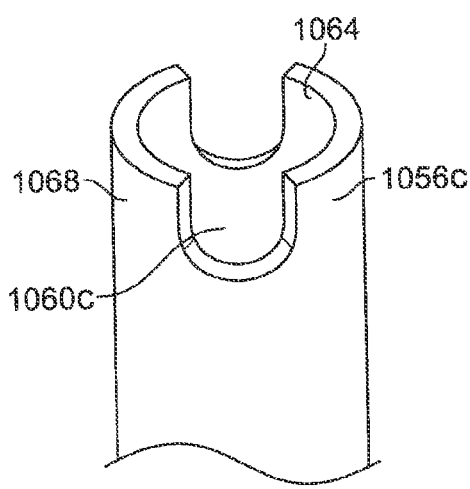
Figure 39:
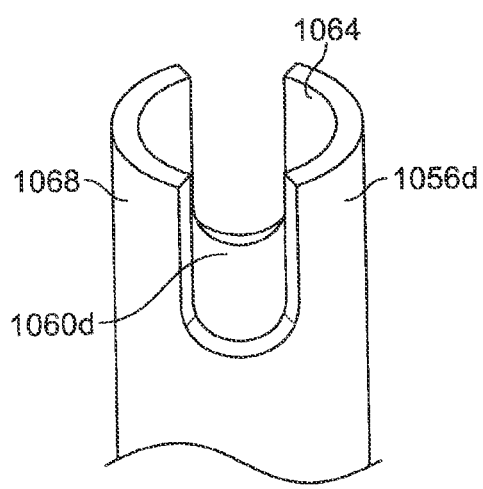

FIGS. 31 and 32 depict one embodiment of an engagement mechanism that may be practiced with the present embodiment by modifying the overhang portion 308 of the actuator arm 30 and the valve stem 278 of the container 60. FIG. 31 shows the overhang portion 308 having a downwardly projecting actuating element 976 within an interior portion thereof. The actuating element 976 includes a cylindrical engagement member 980 having a tapered end with a sealing surface 984. If a conventional aerosol container is placed within the dispenser 10*d*, the sealing surface 984 engages with portions of the valve stem defining a discharge orifice and form a seal therewith. During a dispensing operation, no fluid (or substantially no fluid) will be discharged from the container when the valve stem is depressed by the actuating element 976 because the flow of fluid is obstructed.

FIG. 32 depicts an isometric view of the modified valve stem 278 of the present embodiment. A first channel 988 extends axially through a length of the valve stem 278 and is in fluid communication with one or more secondary channels or grooves 992. When the valve element 278 is depressed by the engagement member 980, such as depicted in FIG. 31, the valve in the container 60 is opened and aerosolized fluid flows around or past the engagement member 980 in the direction of the arrows. After passing the engagement member 980, the fluid traverses the length of the grooves 992 from an inner surface 996 of a circumferential side wall 1000 of the valve stem 278 to a tip surface 1004 of the side wall 1000. In a different embodiment, one or more channels may extend from the inner surface 996 of the side wall 1000 to an exterior surface 1008 thereof. In yet other embodiments, the engagement member 980 is adapted to engage the inner surface 996, the tip surface 1004, and/or the exterior surface 1008 in a manner that allows for fluid communication between the container 60 and a point past the engagement member 980. With reference again to FIG. 31, it may be seen that the overhang portion 308 includes a cylindrical chamber 1008 for receipt of the distal end 282 of the valve stem 278 to align same with the engagement member 980 and to channel discharged fluid through the dispensing bore 324. The dispensing bore 324 extends between the upper side 328 of the overhang portion 308 and the lower side 320 thereof in a manner as described above. However, the dispensing bore 324 of the present embodiment is disposed within the overhang portion 308 in a manner that is offset from an axial length of the valve element 278.

It is anticipated that numerous other engagement mechanisms will be employed with the embodiments described herein. For example, FIG. 33 depicts the valve stem 278 having a square axial passage 1012. An actuating element 1016 is provided that includes a spherical spring-biased ball 1020. When the ball 1020 and the valve stem 278 are engaged during a dispensing sequence, the ball 1020 is at least partially disposed within the axial passage 1012. Fluid ejected through the valve stem 278 may pass through one or more clearances 1024 provided about the periphery of the axial passage 1012. If a conventional cylindrical valve stem were to be engaged with the ball 1020, there would be no (or substantially no) clearance for the emission of the fluid. The square axial passage 1012 may be modified to take on any shape and/or size so long as the corresponding actuating element 1016 has a different shape and/or size to allow for clearance to exist therebetween.

FIGS. 34 and 35 depict yet another embodiment of the valve element 278 that includes an interior surface 1024 defining a first channel 1028 and an exterior surface 1036 that includes a second channel 1040 disposed therein. An actuating element 1044 includes a hollow engagement member 1048, which has a generally inverted frustoconical shape for sealing engagement with a peripheral surface 1052 of the valve stem 278. When the valve element 278 and the engagement member 1048 are engaged during a dispensing sequence, the fluid first flows in the direction of the arrow upwardly through the first channel 1028 and thereafter downwardly through the second channel 1040. If a conventional cylindrical valve stem is utilized with the present embodiment the fluid will be trapped within the engagement member 1048 and no (or substantially no) fluid will be discharged from the dispenser 10*d*.

In a different embodiment, the valve element 278 is modified to include the structure shown in any of FIGS. 36-44. All of the modified valve elements include exterior ends 1056*a-i* having reduced diameters and at least one side opening 1060*a-i*, respectively. The side openings 1060*a-i* extend from an interior axial chamber 1064 of the valve stem 278 through an outer wall 1068 thereof. The presently described valve elements 278 are preferably used in conjunction with a modified version of a dispenser inlet valve that is described in connection with FIGS. 25-34 of U.S. Pat. No. 6,978,914. It is intended that the structure disclosed with respect to the dispenser inlet valve be modified to be incorporated fully or partially into the actuator arm 132 of the various embodiments disclosed herein. The various arrangements described above will prevent emission of the contents of a container, which does not include a valve stem with at least one side opening and a reduced diameter at an upper end thereof.

It should be apparent to one skilled in the art that any of the structural and functional characteristics of the engagement mechanisms described in U.S. Pat. Nos. 6,830,164 and 6,978,914 may be used with any of the embodiments disclosed herein. Further, it is anticipated that the actuator arm 30 and the valve stem 278 may be accordingly modified to carry out any of the disclosed engagement mechanisms.

Figure 29:
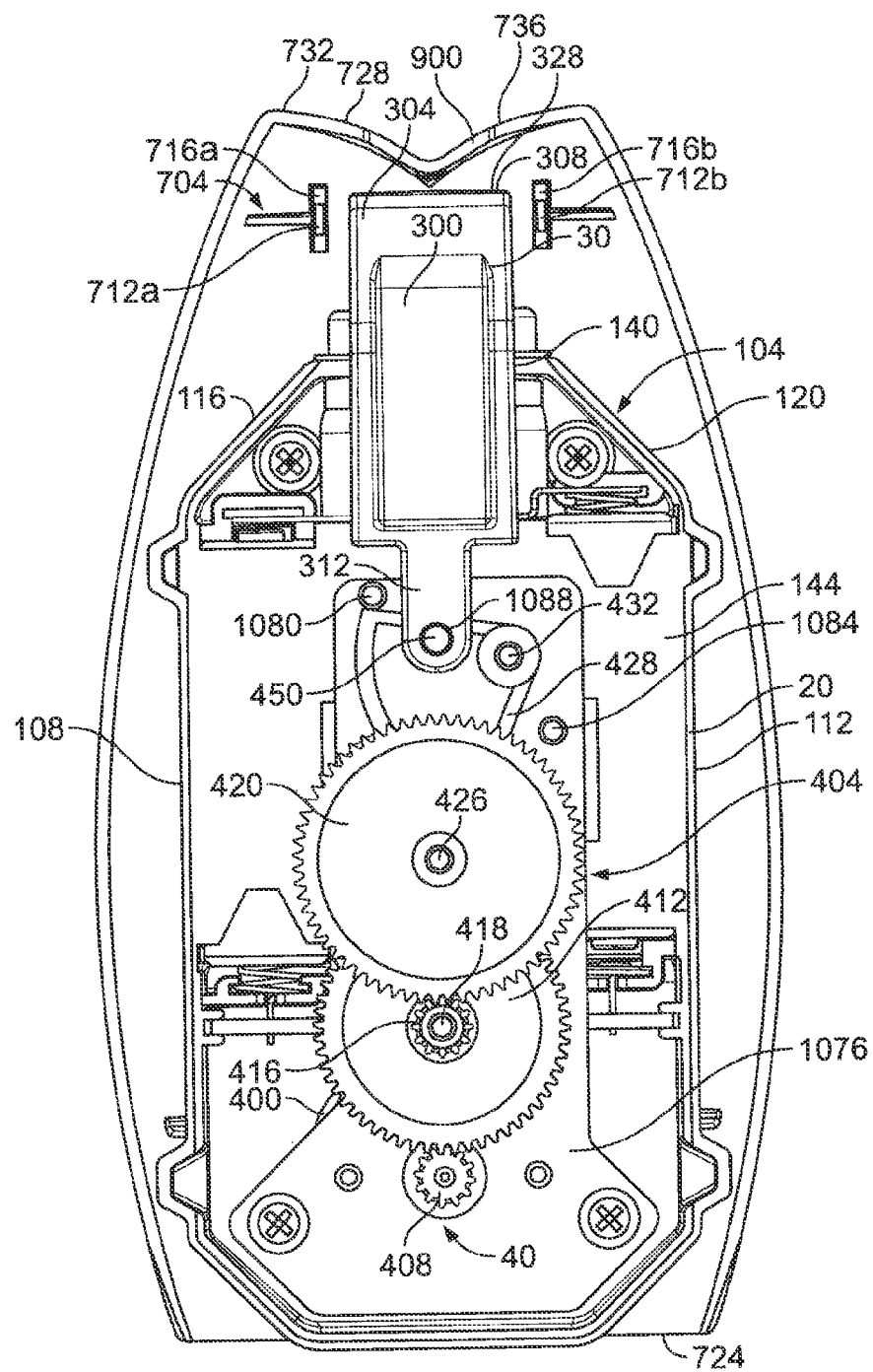
FIG. 29 is a view similar to that of FIG. 26, except that a rear panel has been removed to show a drive unit and an actuator arm.

FIGS. 27-29 show that the positioning and shape of the actuator arm 30 and the actuator arm cover 124 with respect to each other and the dispenser 10*d* are similar to those shown in FIGS. 20-22 in connection with dispenser 10*c*. Further, the functional characteristics of the actuator arm 30 of the present embodiment are also similar to those described in connection with dispenser 10*c*. As noted previously, the actuator arm 30 is driven downwardly along a path during a discharge operation to depress the valve stem 278 and emit fluid from the container 60. The path preferably has a directional component that is parallel to at least one of a longitudinal axis of the container 60, a longitudinal axis of the recess 1072, or a longitudinal axis of the dispensing bore.

Turning to FIG. 30, it may be seen that the drive motor 400 and the associated gear train 404 used to depress the valve stem 278 operate in substantially the same way as described in connection with the dispenser 10*c*. However, several differences between the dispenser 10*d* and the dispenser 10*c* are discussed herein to further clarify the present embodiment. One particular difference is the provision of a metal plate 1076 mounted to the inner rear panel 144. The axles 418, 426, and 432 cantilever from the plate 1076 instead of projecting from the inner rear panel 144. The metal plate 1076 allows for better alignment of the axles 418, 426, and 432 and the attendant gears because of the rigidity of the material. The ability to have greater control over alignment of the transmission allows for closer tolerances between the elements comprising the transmission, thereby providing the benefit of reduced noise during operation of the dispenser 10*d*.

Another difference is that the holes 429, 430, 436, which are adapted to receive distal ends of the axles 418, 426, 432, respectively, are no longer provided in the outer rear panel 148. Instead, annular projections (not shown) are provided on an inner surface of the outer rear panel 148 to receive distal ends of the axles 418, 426, 432. Similarly, annular projections (not shown) are provided on the inner surface of the outer rear panel 148 to receive distal ends of ribs 1080, 1084, which project from the metal plate 1076 and act as limits on the movement of the lever gear 428. Further, the offset pin 450 of the lever gear 428 is provided within a circular hole 1088 as opposed to the truncated racetrack shaped groove 820 provided for in the dispenser 10*c*.

Yet another difference in the present embodiment is that the motor 400 is a two-way motor, i.e., the motor 400 is driven in two directions to open and close the valve assembly 274. In this case, when spraying is to be terminated, the motor 400 is energized in a second direction to reverse the downward force on the actuator arm 30 and the valve stem 278. The actuator arm 30 and the valve stem 278 then move upwardly to the pre-actuation position in response to upward movement of the actuator arm 30 and the upward force provided by the valve assembly 274, at which time the valve assembly 274 of the container 60 is closed. However, it is anticipated that unidirectional motor activation may be utilized in the present embodiment. Further, the motor 400 of the present embodiment may be larger than the motor of the dispenser 10*c*, which reduces noise when the motor 400 is activated.

INDUSTRIAL APPLICABILITY

The dispenser described herein advantageously allows for the contents of an aerosol container to be sprayed into the atmosphere. The dispenser utilizes a compact and lightweight design to afford it a broad spectrum of potential applications throughout numerous areas of a residence, house, or a workplace.

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

We claim:

1. An automatic discharge device, comprising:

a housing retaining first and second containers therein;

first and second actuator arms attached to the housing and movable between first and second positions; and a drive unit including a motor for automatically moving the first and second actuator arms into one of the first and second positions in response to a signal from at least one of a timer, a sensor, and a manual switch, wherein the movement of the first and second actuator arms actuates valve stems of the first and second containers in one of the first and second positions, and wherein the first and second actuator arms are adapted to spray fluid disposed in an interior of the first and second containers.

2. The automatic discharge device of claim 1, wherein the first and second containers are aerosol containers.

3. The automatic discharge device of claim 1, wherein the housing includes surfaces defining a recess for securely holding the first and second containers.

4. The automatic discharge device of claim 3, wherein the drive unit includes at least one gear disposed substantially between the recess and a rear panel of the housing.

5. The automatic discharge device of claim 1, wherein the motor is a two-way drive motor.

6. The automatic discharge device of claim 5, wherein the first and second actuator arms move along a path substantially parallel to an axial length of one of the two containers upon activation of the drive motor.

7. An automatic discharge device, comprising:

a housing having a recess adapted to retain a container therein;

a combination of sensors for detecting an environmental condition;

an actuator arm attached to the housing and movable between first and second positions; and a drive unit for automatically moving the actuator arm into one of the first and second positions in response to a signal from at least one of the combination of sensors, a timer, and a manual switch, wherein the movement of the actuator arm actuates a vertically depressible valve stem of the container allowing a fluid disposed in an interior of the container to be vertically dispensed and exited from the housing through a terminal outlet in an upward direction.

8. The automatic discharge device of claim 7, wherein the actuator arm moves along a path substantially parallel to an axial length of the container upon activation of the drive unit.

9. The automatic discharge device of claim 7, wherein the drive unit includes at least one gear disposed between the recess and a rear panel of the housing.

10. The automatic discharge device of claim 7, wherein the combination of sensors are light sensors.

11. The automatic discharge device of claim 7, wherein the combination of sensors are motion sensors.

12. The automatic discharge device of claim 7, wherein the drive unit includes a two-way drive motor.

* * * * *